US009322045B2

(12) United States Patent
Van Peij et al.

(10) Patent No.: US 9,322,045 B2
(45) Date of Patent: *Apr. 26, 2016

(54) HOST CELL FOR THE PRODUCTION OF A COMPOUND OF INTEREST

(71) Applicant: DSM IP ASSETS B.V., Heerlen (NL)

(72) Inventors: Noël Nicolaas Maria Elisabeth Van Peij, Echt (NL); Herman Jan Pel, Echt (NL); Thibaut José Wenzel, Echt (NL); Adriana Marina Riemens, Echt (NL); Ilse De Lange, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/249,587

(22) Filed: Apr. 10, 2014

(65) Prior Publication Data

US 2014/0248662 A1 Sep. 4, 2014

Related U.S. Application Data

(63) Continuation of application No. 13/386,004, filed as application No. PCT/EP2010/059390 on Jul. 1, 2010, now Pat. No. 8,734,782.

(30) Foreign Application Priority Data

Jul. 22, 2009 (EP) .................................. 09166074

(51) Int. Cl.
| | |
|---|---|
| *C12P 21/00* | (2006.01) |
| *C12N 9/34* | (2006.01) |
| *C12N 15/80* | (2006.01) |
| *C12N 15/85* | (2006.01) |
| *C12N 15/90* | (2006.01) |

(52) U.S. Cl.
CPC ............... *C12P 21/00* (2013.01); *C12N 9/2428* (2013.01); *C12N 15/80* (2013.01); *C12N 15/8509* (2013.01); *C12N 15/902* (2013.01); *A01K 2267/01* (2013.01)

(58) Field of Classification Search
None
See application file for complete search history.

(56) References Cited

U.S. PATENT DOCUMENTS

| 2009/0124014 A1 | 5/2009 | Berg et al. |
| 2009/0170206 A1 | 7/2009 | van de Berg et al. |
| 2010/0112638 A1 | 5/2010 | Sagt et al. |

FOREIGN PATENT DOCUMENTS

| WO | 9846772 | 10/1998 |
| WO | 9846774 | 10/1998 |
| WO | WO2007115886 | 10/2007 |
| WO | 2008098933 | 8/2008 |

OTHER PUBLICATIONS

Huang et al. (2007) "An efficient and targeted gene integration system for high-level antibody expression" Journal of Immunological Methods 322:28-39.

*Primary Examiner* — Tracy Vivlemore
*Assistant Examiner* — Karen S Weiler
(74) *Attorney, Agent, or Firm* — MMWV IP, LLC.

(57) ABSTRACT

The present invention relates to a recombinant host cell for the production of a compound of interest. The invention further relates to a method for the production of such host cell. The invention further relates to the production of a compound of interest. The invention further relates to isolated polynucleotides and vectors and host cells comprising said polynucleotides.

23 Claims, 21 Drawing Sheets

HOST CELL FOR THE PRODUCTION OF A COMPOUND OF INTEREST

CROSS-REFERENCE TO RELATED APPLICATIONS

This is a continuation of U.S. patent application Ser. No. 13/386,004, having a 35 U.S.C. §371(c) date of Apr. 2, 2012, which is a National Stage Entry of PCT/EP2010/59390, filed Jul. 1, 2010, which claims priority to EP 09166074.6, filed Jul. 22, 2009, the contents of each of which are incorporated by reference in their entireties.

BACKGROUND OF THE INVENTION

1. Field of the Invention

The present invention relates to a recombinant host cell for the production of a compound of interest. The invention further relates to a method for the production of such host cell. The invention further relates to the production of a compound of interest. The invention further relates to isolated polynucleotides and vectors and host cells comprising said polynucleotides.

2. Description of Related Art

The present invention relates to a recombinant host cell for the production of a compound of interest.

Such host cells are inter alia known from WO1998/046774 and WO1998/46772, wherein the host cell comprises a polynucleotide of interest in one of at least two substantially homologous DNA domains of the chromosome(s) of said host cell and wherein the copy number of the polynucleotide of interest is increased by means of gene conversion.

However, it has been demonstrated that obtaining a high-copy gene conversion strain, such as those obtained by the method according to WO1998/046774 and WO1998/46772, is often considered to be laborious. It would be therefore be advantageous if the method could be improved in order to enable less laborious construction of a high-copy gene conversion strain.

Figure 16:
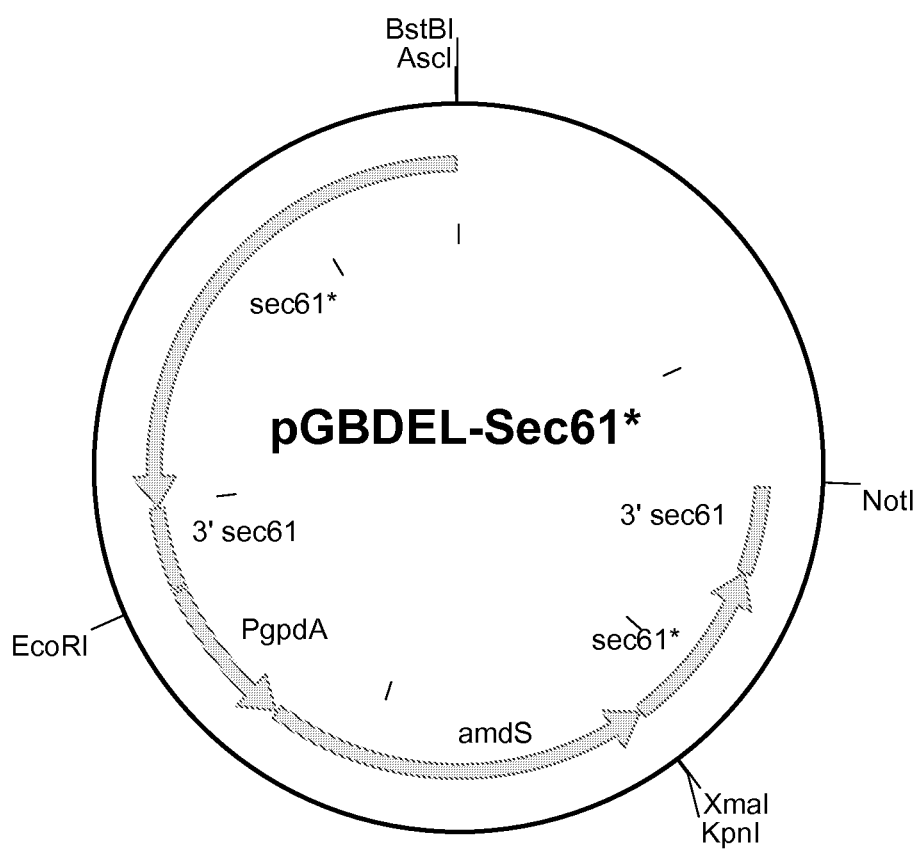

FIG. 16 depicts a physical map of replacement vector pGB-DEL-Sec61*. Indicated are a Sec61* mutant gene and a 3' Sec61* mutant gene fragment relative to the amdS marker. The *E. coli* DNA can be removed by digestion with restriction enzyme AscI and NotI, prior to transformation to the host strain.

Figure 17:
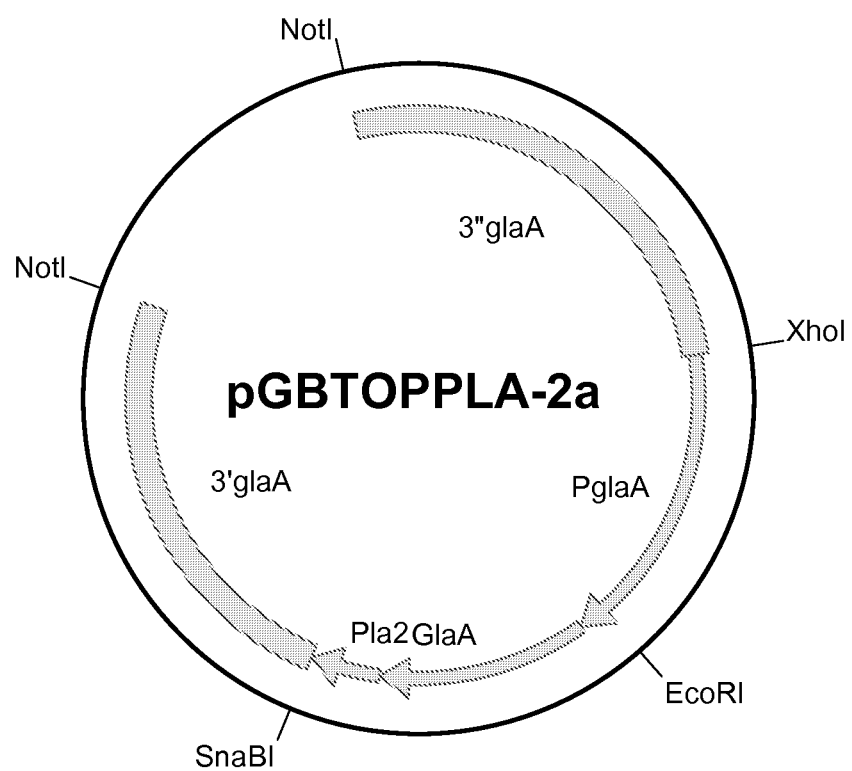

FIG. 17 depicts a physical map of the PLA2 expression vector pGBTOPPLA-2a. Indicated are the glaA flanking regions relative to the glaA promoter, the truncated glaA gene and the pro-pla2 coding sequence. The *E. coli* DNA can be removed by digestion with restriction enzyme NotI, prior to transformation to the host strain.

Figure 18:
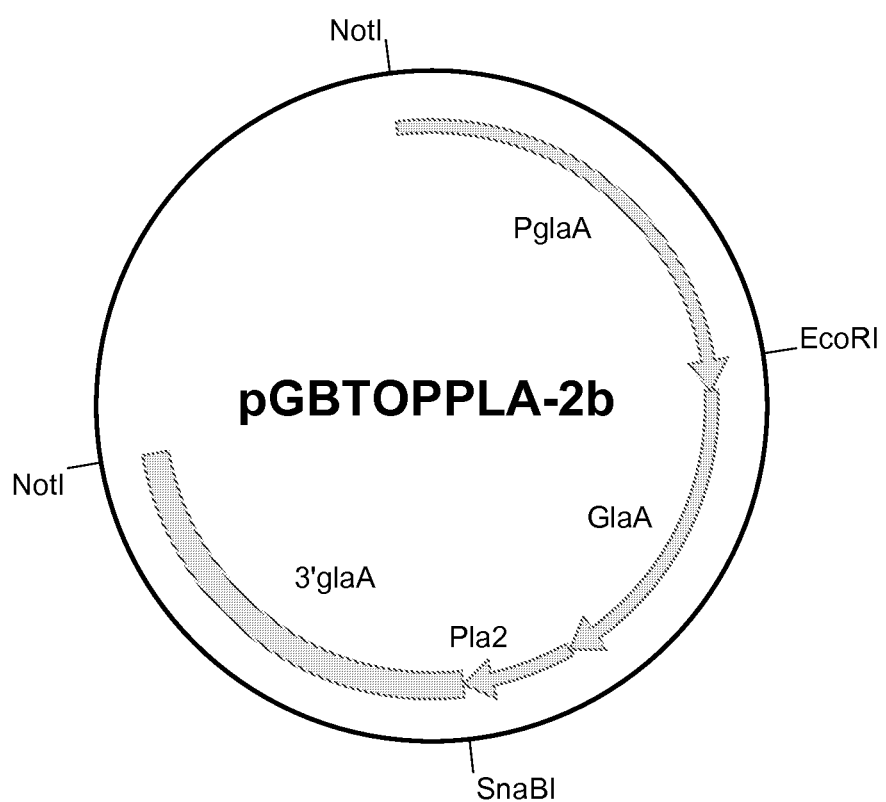

FIG. 18 depicts a physical map of the PLA2 expression vector pGBTOPPLA-2b. Indicated are the glaA promoter, the truncated glaA gene, the pro-pla2 coding sequence and the 3'glaA flanking sequence. The *E. coli* DNA can be removed by digestion with restriction enzyme NotI, prior to transformation to the host strain.

Figure 19:
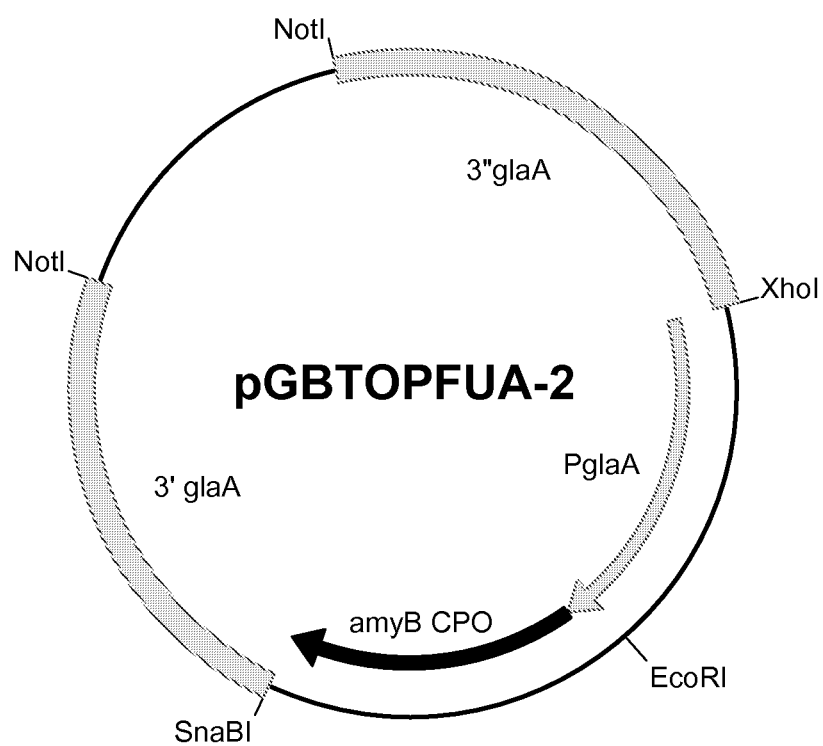

FIG. 19 depicts a physical map of expression vector pGBFINFUA-2. Indicated are the glaA flanking regions relative to the glaA promoter and the *A. niger* amyB codon optimized sequence. The *E. coli* DNA can be removed by digestion with restriction enzyme NotI, prior to transformation of the host strain.

Figure 20:
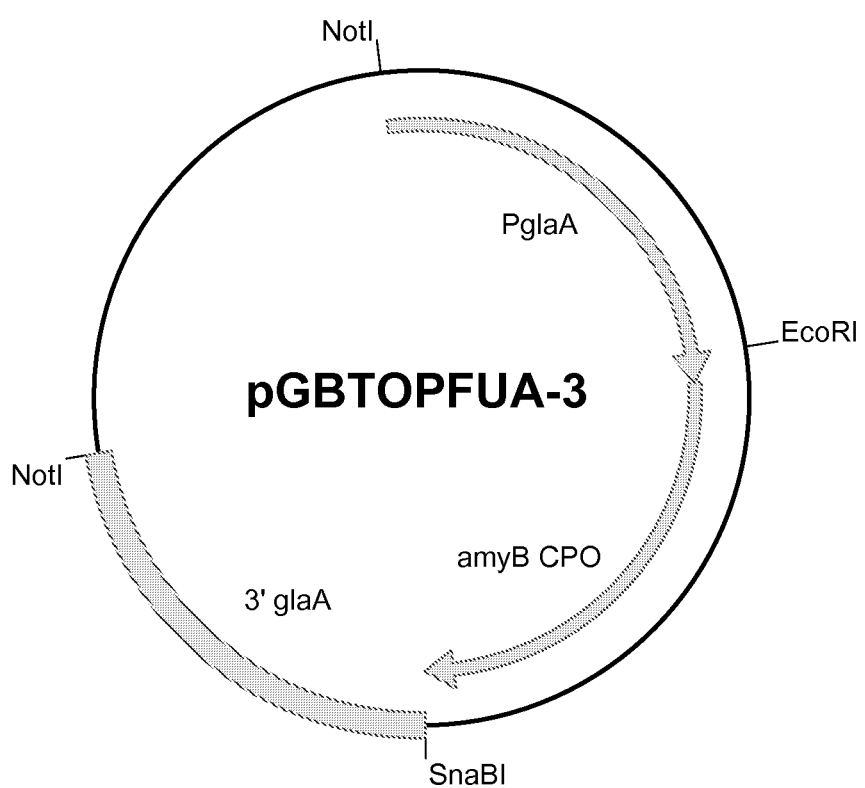

FIG. 20 depicts a physical map of the FUA expression vector pGBTOPFUA-3. Indicated are the glaA promoter, the truncated glaA gene, the *A. niger* amyB codon optimized sequence and the 3'glaA flanking sequence. The *E. coli* DNA can be removed by digestion with restriction enzyme NotI, prior to transformation to the host strain.

Figure 21:
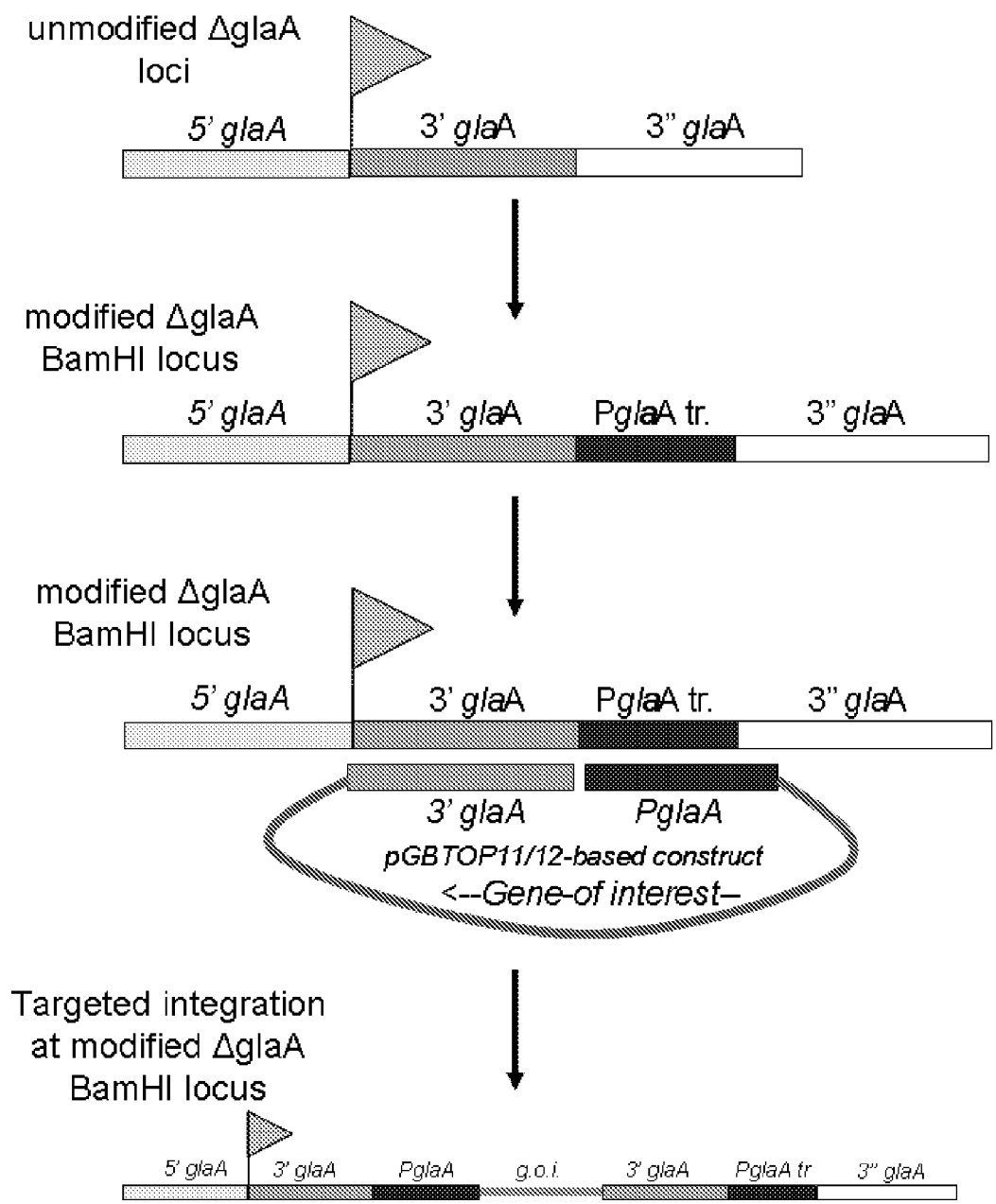

FIG. 21 depicts a schematic representation of integration through single homologous recombination in a strain with an adapted BamHI amplicon (as for example GBA 303-based strains in the examples). The expression vector comprises a selectable amdS marker with specific targeting sequences and a gene of interest. The targeting sequences allow specific genomic targeting to the adapted amplicon with the highest frequency of gene conversion ("Smart integration strategy").

DETAILED DESCRIPTION OF A PREFERRED EMBODIMENT

Analysis revealed surprisingly that where a host cell, such as those described in WO1998/046774 and WO1998/46772, comprises at least two substantially homologous DNA domains, the gene conversion frequencies of the DNA domains are not necessarily equal. Some of these DNA domains revealed to have a gene conversion frequency that is substantially lower than that of other substantially homologous DNA domains. In such case, it is a disadvantage if the polynucleotide of interest is integrated in a DNA domain that has a low gene conversion frequency and not in a DNA domain that has a high gene conversion frequency. The DNA domain with the higher gene conversion frequency will to a large extent out-compete the DNA domain with the lower gene conversion frequency (which comprises the polynucleotide of interest). Consequently, it will be more laborious to obtain a high-copy gene conversion host cell from a cell that has the polynucleotide of interest integrated in a DNA domain with lower gene conversion frequency.

It would be therefore be advantageous if the polynucleotide of interest can be comprised in a substantially homologous DNA domain that has a substantially higher gene conversion frequency since this would enable less laborious construction of a host strain comprising multiple copies of the polynucleotide of interest (high-copy gene conversion strain).

Consequently, there is a need for a host cell wherein the polynucleotide of interest preferentially integrates in a homologous DNA domain that has a substantially higher gene conversion frequency. It is therefore an object of the present invention to provide such host cell.

Accordingly, the present invention provides for a recombinant host cell for the production of a compound of interest, said host cell comprising at least two substantially homologous DNA domains suitable for integration of one or more copies of a polynucleotide of interest wherein at least one of the at least two substantially homologous DNA domains is adapted to have enhanced integration preference for the polynucleotide of interest compared to the substantially homologous DNA domain it originates from. Said recombinant host cell is herein referred to as the recombinant host cell according to the invention.

The present invention also provides for a method for the production of a recombinant host cell for the production of a compound of interest, said host cell comprising at least two substantially homologous DNA domains suitable for integration of one or more copies of a polynucleotide of interest, comprising adapting a substantially homologous DNA domain with higher gene conversion frequency compared to another substantially homologous DNA domain to have enhanced integration preference for the polynucleotide of interest compared to the substantially homologous DNA domain it originates from.

The present invention also provides for a method for the production of a compound of interest, comprising:
  a. cultivating a host cell according to the invention under conditions conducive to the production of said compound; and
  b. recovering the compound of interest from the cultivation medium.

The present invention also provides for a method for the production of a compound of interest comprising
  a. cultivating a recombinant host cell under conditions conducive to the production of said compound, said host cell comprising at least two substantially homologous DNA domains suitable for integration of one or more copies of a polynucleotide of interest, wherein at least one of the at least two substantially homologous DNA domains is adapted to have enhanced integration preference for the polynucleotide of interest compared to the substantially homologous DNA domain it originates from, and wherein at least two of the substantially homologous DNA domains have at least one copy of a polynucleotide of interest integrated; and
  b. recovering the compound of interest from the cultivation medium.

Accordingly, a recombinant host cell according to the invention comprises at least two substantially homologous DNA domains suitable for integration of one or more copies of a polynucleotide of interest wherein at least one of the at least two substantially homologous DNA domains is adapted to have enhanced integration preference for the polynucleotide of interest compared to the substantially homologous DNA domain it originates from. Said substantially homologous DNA domains suitable for integration of one or more copies of said polynucleotide of interest preferably are substantial duplicates of each other; more preferably said DNA domains are amplicons.

In the context of the present invention, the term "recombinant" refers to any genetic modification not exclusively involving naturally occurring processes and/or genetic modifications induced by subjecting the host cell to random mutagenesis but also gene disruptions and/or deletions and/or specific mutagenesis, for example. Consequently, combinations of recombinant and naturally occurring processes and/or genetic modifications induced by subjecting the host cell to random mutagenesis are construed as being recombinant.

The host cells according to the invention comprise in their genome at least two substantially homologous DNA domains suitable for integration of one or more copies of a polynucleotide of interest. In wild-type strains these DNA domains may occur in a single copy or in multiple copies in the genome of said cell. Examples of multiple copy DNA domains occurring naturally are rDNA domains. Accordingly, rDNA domains may preferably be used or not be used in the present invention. Strains containing multiple copies of these substantially homologous DNA domains, as provided by the present invention, can e.g. be obtained from strains comprising a single copy of a DNA domain by classical strain improvement by selecting for strains with improved production of the gene products encoded by the gene(s) in said DNA domains. Frequently, such production improvements are the result of amplification of a DNA domain in the selected strains. Such amplified DNA domains are also referred to as amplicons hereinafter. Examples of host cells comprising such amplicons are e.g. described in van Dijck et al, 2003, Regulatory Toxicology and Pharmacology 28; 27-35: On the safety of a new generation of DSM *Aspergillus niger* enzyme production strains. In van Dijck et al, an *Aspergillus niger* strain is described that comprises 7 amplified glucoamylase gene loci, i.e. amplicons. Although the present invention preferably uses such amplicons as DNA domains for the integration of the recombinant DNA molecules, the invention is by no means limited thereto. In fact, any DNA domain of which two or more substantially homologous versions occur in the genome of a host cell can be used as long as two functional criteria are fulfilled: 1) the DNA domain should be suitable for accepting the integration of a polynucleotide of interest; 2) the DNA domain should be capable of recombination with the other substantially homologous versions of the DNA domain in the fungal genome in order to achieve multiplication of the integrated recombinant DNA molecule through gene conversion.

In order to meet the first criterion, a DNA domain must be of sufficient length in order to allow targeting of the polynucleotide of interest into the DNA domain through homologous recombination. For this purpose a DNA domain should comprise at least 100 bp, preferably at least 500 bp, more preferably at least 1 kb and more preferably at least 2 kb. Preferably, the suitability of a DNA domain for integration therein of a polynucleotide of interest is furthermore determined by the requirement that integration into the DNA domain should not disrupt functions that are essential for the viability of the host cell in question.

The second functional criterion, i.e. the capability of recombination with the other substantially homologous versions of the DNA domain in the genome of the host cell, is required for allowing gene conversions between the different versions of the DNA domain. The minimal requirement for this purpose is that each version of the DNA domain is flanked on either end of the DNA domain by DNA sequences that are sufficiently homologous to the corresponding flanking sequences of the other version of the DNA domains so as to allow homologous recombination between the flanking sequences. The result of this homologous recombination being a gene conversion wherein one of the versions of the DNA domain is replaced by a duplicated version of the other DNA domain containing the integrated recombinant DNA molecule. The minimum requirements regarding length and extend of homology of the flanking sequences still allowing gene conversion may vary depending on the organism in question. Probably, a minimum length of 100 bp with an overall homology at least 60% will still allow gene conversion. Obviously, the frequency of gene conversion will increase with increasing length and homology of the flanking sequences. Preferably the different DNA domains comprise flanking sequences of at least 1 kb which share at least 80% homology. Even more preferably the different DNA domains comprise flanking sequences of at least 5 kb which share at least 95% homology. In a more preferable embodiment the different DNA domains comprise flanking sequences of at least 10 kb which share at least 99% homology. In a most preferable embodiment, the different DNA domains comprise flanking sequences of at least 50 kb which share at least 99% homology. Examples of substantially homologous DNA domains which are not perfect copies of each other, designated herein substantial duplicates, are allelic variants, gene families and/or genes encoding iso-enzymes. Most preferred are substantially homologous DNA domains which are exact copies of each other, differing at most in the presence of the integrated polynucleotide of interest. Examples of such identical DNA domains are amplicons. Alternatively, artificial DNA domains may be created using DNA synthesis and/or recombinant DNA technology, and such artificial DNA domains may then be introduced and amplified in the desired fungus. Accordingly, such artificial DNA domains may preferably be used or not be used in the present invention.

The overall length of the substantially homologous DNA domains, i.e. including the flanking sequences may vary from less than 1 kb to several hundreds of kb's, e.g. previously it has been demonstrated that the length of the DNA domains ranges from few kb's per unit for the three TAKA amylase genes present in the *Aspergillus oryzae* parental strain IF04177 (disclosed in WO9812300 and U.S. Pat. No. 5,766, 912 as A1560), which have been inactivated in *A. oryzae* BECh2 (disclosed in WO0039322) until about 57 kb per unit for the amplified penicillin cluster in *Penicillium chrysogenum* and more than 80 kb per unit for the amplified glaA locus of *Aspergillus niger* (see WO9846772).

Gene conversion can be monitored by identifying host cells in which the DNA domain comprising the polynucleotide of interest is multiplied. Any method known to the person skilled in the art can be used, e.g. simply screening for host cells with higher production levels of the product encoded by polynucleotide of interest. Also quantitative methods for determination of DNA copy numbers such as for example analysis of the genotype of host cells by e.g. the "DNA-flag" test as outlined here below, quantitative PCR, Southern analysis or comparative genome hybridization or for determination of RNA levels, such as for example RT-PCR, Northern analysis or GeneChip or microarray analysis can be used.

According to the invention, each version of a substantially homologous DNA domain is preferably distinguished from the other versions of the DNA domains in the filamentous fungus by means of a unique sequence tag for identification purposes. Such sequence tags allow detection and monitoring gene conversions between the different DNA domains, thus facilitating the screening and/or selection of gene convertants with a desired genotype. Any form of sequence tags can be used as long as they allow detection of the different versions of the DNA domain: e.g. ranging from restriction sites that are detected on Southern blots to complete selectable marker genes providing an easy assayable phenotype. A particularly useful sequence tag method is described in WO9846772, WO9846774 and in van Dijck et al, supra. This method allows detecting each of the DNA domains in a single PCR using a single pair of oligonucleotide PCR primers. The DNA domains are modified in such a way that in the PCR each version of the DNA domains produces a PCR fragment with a unique length. The length and intensity of the obtained PCR fragments are indicative for the presence and copy number of each of the DNA domains, respectively. This form of sequence tag, referred to as "DNA flags", allows for rapid analysis of the genotype of large numbers of convertant colonies, in order to obtain a convertant with the desired genotype.

According to the invention, one of the at least two substantially homologous DNA domains of the host cell according to the invention is adapted to have enhanced integration preference for the polynucleotide of interest compared to the substantially homologous DNA domain it originates from. Preferably, a targeting DNA domain of one of the at least two substantially homologous DNA domains of the host cell is adapted to allow a more specific targeting of the recombinant DNA molecule/polynucleotide of interest into the adapted targeting DNA domain through homologous recombination. If a targeting DNA sequence or DNA domain occurs more than once in a host cell, homologous recombination of a polynucleotide of interest is found with multiple targeting DNA domains of a host cell. It is possible to adapt a targeting DNA domain in one of the substantially homologous DNA domains to support more specific targeting to that adapted targeting DNA domain without affecting the recombination with other substantially homologous versions of the DNA domain in the host. For optimal targeting preference, adaptation of the DNA sequences used for targeting is done in the recombinant DNA molecule/polynucleotide of interest and in the host. As such, a matching set of host and integration vector are obtained.

Preferably, adapting the targeting DNA domain is executed by introduction of a sequence with enhanced integration preference into the substantially homologous DNA domain. Preferably, said sequence with enhanced integration preference is introduced by gene replacement. Accordingly, the present invention also provides for a recombinant host cell for the production of a compound of interest, said host cell comprising at least two substantially homologous DNA domains suitable for integration of one or more copies of a polynucleotide of interest wherein at least one of the at least two substantially homologous DNA domains is adapted to have enhanced integration preference for the polynucleotide of interest compared to the substantially homologous DNA domain it originates from, wherein the adapted substantially homologous DNA domain comprises a targeting DNA domain, wherein said targeting DNA domain comprises a sequence with enhanced integration preference. More preferably, adapting the targeting domain is executed according to the examples herein.

According to the invention, a targeting sequence of the adapted DNA domain used for targeting is preferably adapted to be unique within the genome of the host. Preferably, the targeting sequence adapted to be unique within the genome of the host comprises a sequence selected from the group of: heterologous DNA polynucleotide sequences, DNA polynucleotide sequences previously removed from the host and re-introduced, homologous DNA polynucleotide fragments assembled in a different order compared to the wild-type situation in a host, and artificial DNA polynucleotides.

According to the invention, one or both flanking sequences of the polynucleotide of interest used for targeting to the adapted DNA domain are preferably unique within the genome of the host. Preferably, one or both flanking sequences of the polynucleotide of interest used for targeting to the adapted DNA domain comprises a sequence selected from the group of: heterologous DNA polynucleotide sequences, DNA polynucleotide sequences previously removed from the host and re-introduced, homologous DNA polynucleotide fragments assembled in a different order compared to the wild-type situation in a host and artificial DNA polynucleotides.

Preferably, both a targeting sequence of the adapted DNA domain is adapted to be unique within the genome of the host and one or both flanking sequences of the polynucleotide of interest used for targeting to the adapted DNA domain are unique within the genome of the host.

According to the invention, a sequence used for targeting to the adapted DNA domain preferably is a genetic element used for introduction and/or expression of a polynucleotide of interest. Examples of genetic elements are a gene, a promoter, a terminator, a cDNA, an intron, an intergenic area, or a part and/or a combination thereof. More preferably, a sequence used for targeting to the adapted DNA domain comprises one or more heterologous genetic elements for introduction and/or expression of a polynucleotide of interest. Even more preferably, one or both flanking sequences of the polynucleotide of interest used for targeting to the adapted DNA domain comprises one or more heterologous genetic elements for introduction and/or expression of a polynucleotide of interest. Even more preferably, a sequence used for targeting to the adapted DNA domain comprises one or more *A. niger* genetic elements for introduction and/or expression of a polynucleotide of interest. Even more preferably, one or both flanking sequences of the polynucleotide of interest used for targeting to the adapted DNA domain comprises one or more *A. niger* genetic elements for introduction and/or expression of a polynucleotide of interest. Even more preferably, a sequence used for targeting to the adapted DNA domain comprises *A. niger* glaA glucoamylase genetic elements and/or flanking regions for introduction and/or expression of a polynucleotide of interest. even more preferably, one or both flanking sequences of the polynucleotide of interest used for targeting to the adapted DNA domain comprises *A. niger* glaA glucoamylase genetic elements and/or flanking regions for introduction and/or expression of a polynucleotide of interest. Even more preferably, a sequence used for targeting to the adapted DNA domain comprises the *A. niger* glaA glucoamylase promoter and/or glucoamylase terminator regions for introduction and/or expression of a polynucleotide of interest. Even more preferably, one or both flanking sequences of the polynucleotide of interest used for targeting to the adapted DNA domain comprises the *A. niger* glaA glucoamylase promoter and/or glucoamylase terminator regions for introduction and/or expression of a polynucleotide of interest. Even more preferably, a sequence used for targeting to the adapted DNA domain comprises the *A. niger* glaA glucoamylase terminator region and glaA glucoamylase promoter in a reverse order compared to the wild-type situation for introduction and/or expression of a polynucleotide of interest. Even more preferably, one or both flanking sequences of the polynucleotide of interest used for targeting to the adapted DNA domain comprises the *A. niger* glaA glucoamylase terminator region and glaA glucoamylase promoter in a reverse order compared to the wild-type situation for introduction and/or expression of a polynucleotide of interest. Even more preferably, a sequence used for targeting to the adapted DNA domain comprises the *A. niger* glaA glucoamylase terminator region and glaA glucoamylase promoter as identified in SEQ ID NO: 2 for introduction and expression of a polynucleotide of interest. Even more preferably, one or both flanking sequences of the polynucleotide of interest used for targeting to the adapted DNA domain comprises the *A. niger* glaA glucoamylase terminator region and glaA glucoamylase promoter as identified in SEQ ID NO: 2 for introduction and expression of a polynucleotide of interest. Most preferably, the sequences used for targeting to the adapted DNA domain and both flanking sequences of the polynucleotide of interest used for targeting to the adapted DNA domain are the same and comprise the *A. niger* glaA glucoamylase terminator region and glaA glucoamylase promoter as identified in SEQ ID NO: 2 for introduction and expression of a polynucleotide of interest.

Accordingly, the present invention provides for a polynucleotide comprising a polynucleotide according to SEQ ID NO: 2 or a functional fragment thereof and vectors and host cells comprising a polynucleotide comprising a polynucleotide according to SEQ ID NO: 2 or a functional fragment thereof. Functional is here to be construed as having promoter activity and a being a targeting sequence with enhanced integration preference. Preferably, a functional fragment of a polynucleotide according to SEQ ID NO: 2 comprises at least 100 bp, more preferably at least 200 bp, more preferably at least 300 bp, more preferably at least 500 bp, more preferably at least 600 bp, more preferably at least 700 bp, more preferably at least 800 bp, more preferably at least 900 bp, more preferably at least 1000 bp, more preferably at least 1200 bp, more preferably at least 1500 bp, more preferably at least 2000 bp, more preferably at least 3000 bp, and even more preferably at least 4000 bp. Preferably, the functional fragment has a match percentage, i.e. positional identity of at least about 50%, more preferably of at least about 60%, even more preferably of at least about 70%, even more preferably of at least about 80%, even more preferably of at least about 85%, even more preferably of at least about 90%, even more preferably of at least about 95%, even more preferably of at least about 97%, even more preferably of at least about 98%, even more preferably of at least about 99% identity, and even preferably, the match percentage i.e. identity is equal to 100%.

Most preferably, the polynucleotide comprising a polynucleotide according to SEQ ID NO: 2 comprises SEQ ID NO: 3 or a functional fragment thereof. Functional is here to be construed as having promoter activity and a being a targeting sequence with enhanced integration preference.

Accordingly, the present invention provides for a polynucleotide comprising a polynucleotide according to SEQ ID NO: 3 or a functional fragments thereof and vectors and host cells comprising a polynucleotide comprising a polynucleotide according to SEQ ID NO: 3 or functional fragments thereof. Preferably, a functional fragment of SEQ ID NO: 3 comprises at least 100 bp, more preferably at least 200 bp, more preferably at least 300 bp, more preferably at least 500 bp, more preferably at least 600 bp, more preferably at least 700 bp, more preferably at least 800 bp, more preferably at least 900 bp, more preferably at least 1000 bp, more preferably at least 1200 bp, more preferably at least 1300 bp and even more preferably at least 1400 bp. Preferably, the functional fragment has a match percentage, i.e. positional identity of at least about 50%, more preferably of at least about 60%, even more preferably of at least about 70%, even more preferably of at least about 80%, even more preferably of at least about 85%, even more preferably of at least about 90%, even more preferably of at least about 95%, even more preferably of at least about 97%, even more preferably of at least about 98%, even more preferably of at least about 99% identity, and most preferably, the match percentage i.e. identity is equal to 100%.

Examples of polynucleotides are, but are not limited to, ribonucleic acid (RNA) and deoxyribonucleic acid (DNA) molecules, either single stranded or double stranded. The person skilled in the art will comprehend that the complementary and reverse-complementary of the polynucleotides claimed herein are intended to fall within the scope of the present invention.

According to an embodiment of the invention, a sequence used for targeting to the adapted DNA domain is preferably a genetic element for introduction and/or expression of a polynucleotide of interest, wherein the functionality of the genetic element in the adapted DNA domain is disrupted upon integration of a construct. According to another embodiment of the invention, a sequence used for targeting to the adapted DNA domain is preferably a genetic element for introduction and/or expression of a polynucleotide of interest, wherein the functionality of the genetic element in the adapted DNA domain is restored upon integration of a construct.

It has previously been demonstrated that substantially homologous DNA domains can multiply through gene conversion and/or through gene amplification. Although being different, for use herein both terms gene conversion and gene amplification are used interchangeably. Different substantially homologous DNA domains revealed to have different frequencies of multiplication, i.e. gene conversion frequencies. The advantage of adapting a targeting DNA domain of a substantially homologous DNA domain with the highest gene conversion frequency is inter alia that screening and selection of a host with increased copy numbers of a polynucleotide of interest through gene conversion and/or amplification is much more efficient.

Accordingly, the substantially homologous DNA domain where the adapted substantially homologous DNA domain originates from has a gene conversion frequency that is preferably at least 10% higher than one of the other of the at least two substantially homologous DNA domains. More preferably, the gene conversion frequency is at least 15% higher, even more preferably at least 20% higher, even more preferably at least 30% higher, even more preferably at least 40% higher, even more preferably at least 50% higher, even more preferably at least 60% higher, even more preferably at least 70% higher, even more preferably at least 80% higher, even more preferably at least 90% higher, even more preferably at least 100% higher, even more preferably at least 150% higher, even more preferably at least 200% higher, even more preferably at least 300% higher, even more preferably at least 400% higher, even more preferably at least 500% higher, and even more preferably at least 1000% higher.

According to the invention a substantially homologous DNA domain having a higher gene conversion frequency can be identified by determining the gene conversion frequency of the substantially homologous DNA domains of a host cell. The gene conversion frequency can be determined by any means known to the person skilled in the art. A preferred method is the method described herein in example 3.1. In this method, a host cell comprising three substantially homologous DNA domains is transformed with a polynucleotide of interest. Three transformants are selected, each comprising a single copy of the polynucleotide of interest in a single substantially homologous DNA domain, each transformant having the polynucleotide integrated in a different substantially homologous DNA domain. After propagation of the transformants into offspring clones, the genotype of the offspring clones is determined by means of the unique sequence tag for identification purposes, i.e. using the "flag DNA" analysis described here above. The gene conversion frequency of a substantially homologous DNA domain is now calculated by dividing the amount of gene convertants of a transformant comprising said substantially homologous DNA domain by the total number of clones of said specific transformant.

Preferably, the host cell according to the invention is a cell wherein at least two of the substantially homologous DNA domains each have at least one copy of a polynucleotide of interest integrated. More preferably, each of said domains has at least two copies of the polynucleotide of interest integrated, even more preferably at least three copies, even more preferably four copies, even more preferably four to six copies. Preferably, each substantially homologous DNA domain of the host cell according to the invention has the same number of the polynucleotide of interest integrated.

The copy number of the polynucleotide of interest can be determined by any method available to the person skilled in the art, e.g. analysis of the genotype by Southern analysis or (semi) quantitative PCR, expression analysis by Northern analysis, GeneChip or microarray analysis or (semi) quantitative RT-PCR, analysis of the product encoded by the polynucleotide of interest by Western blot, ELISA, enzyme activity assay. Methods to determine copy numbers of the polynucleotide of interest are extensively described in WO9846772 and are according to the invention preferred methods to determine the copy number of the polynucleotide of interest.

Preferably, the host cell according to the invention comprises at least two substantially homologous DNA domains that are adapted to have enhanced integration preference for the polynucleotide of interest compared to the substantially homologous DNA domain it originates from, more preferably three adapted DNA domains, even more preferably four adapted DNA domains, even more preferably five adapted DNA domains, even more preferably six adapted DNA domains. Most preferably, each substantially homologous DNA domain of said host cell according to the invention is an adapted DNA domain. Preferably, an adapted DNA domain has at least two copies of the polynucleotide of interest integrated, even more preferably at least three copies, even more preferably at least four copies, even more preferably an adapted DNA domain has at least five copies, even more preferably at least six copies, at least seven copies, at least eight copies, at least nine copies, at least ten copies of the polynucleotide of interest integrated. Most preferably, an adapted DNA domains has five or six copies of the polynucleotide of interest integrated. Preferably, each of said adapted DNA domains has the same number of the polynucleotide of interest integrated.

Preferably, said host cell comprising multiple substantially homologous DNA domains that are adapted to have enhanced integration preference for the polynucleotide of interest compared to the substantially homologous DNA domain it originates from, wherein preferably each adapted DNA domain has multiple copies of the polynucleotide of interest integrated, is derived from a host cell comprising a single adapted DNA domain which has multiple copies of the polynucleotide of interest integrated; i.e. the additional copies of the adapted DNA domain which has multiple copies of the polynucleotide of interest integrated are generated by gene conversion.

Preferably, the efficiency of targeted integration of a polynucleotide to a pre-determined site into the genome of the host cell according to the invention is increased by steering an integration pathway towards HR. Such steering can be achieved either by elevating the efficiency of the HR pathway, and/or by lowering (meaning reducing) the efficiency of the NHR pathway and/or by decreasing the NHR/HR ratio.

Eukaryotic cells have at least two separate pathways (one via homologous (HR) and one via non-homologous recombination (NHR)) through which polynucleotides can be integrated into the host genome. In the context of the invention, the HR pathway is defined as all genes and elements being involved in the control of the targeted integration of polynucleotides into the genome of a host, said polynucleotides having a certain homology with a certain pre-determined site of the genome of a host wherein the integration is targeted. The NHR pathway is defined as all genes and elements being involved in the control of the integration of polynucleotides into the genome of a host, irrespective of the degree of homology of the said polynucleotides with the genome sequence of the host.

The ratio of non-homologous to homologous recombination (NHR/HR) determines the efficiency of targeted integration of a polynucleotide to a pre-determined site in the genome of the host cell. When the ratio NHR/HR is high, the efficiency of targeted integration will be relatively low. When the ratio NHR/HR is low, the efficiency of targeted integration will be relatively high. The ratio of NHR/HR can be determined by methods known by the person skilled in the art by means of assessing the frequencies of NHR and HR and subsequently dividing the respective frequencies, an example of a method is the method described in WO 02/052026. Preferably, the host cell according to the invention comprises a polynucleotide encoding an NHR component comprising a modification, wherein said host cell is deficient in the production of said NHR component compared to the parent cell it originates from when cultivated under comparable conditions. Said modification results in a decrease of the NHR/HR ratio, therewith increasing the efficiency of targeted integration of a polynucleotide to a pre-determined site in the genome of the host cell. By modification of a polynucleotide encoding an NHR component, resulting in a deficiency of said NHR component, the ratio NHR/HR of the host cell is steered towards HR and consequently, the efficiency of targeted integration will increase.

Preferably, the host cell according to the invention demonstrates at least 5% deficiency of said NHR component, more preferably at least 10% deficiency, more preferably at least 20% deficiency, more preferably at least 30% deficiency, more preferably at least 40% deficiency, more preferably at least 50% deficiency, more preferably at least 60% deficiency, more preferably at least 70% deficiency, more preferably at least 80% deficiency, more preferably at least 90% deficiency, more preferably at least 95% deficiency, more preferably at least 97% deficiency, more preferably at least 99% deficiency. Most preferably, the host cell demonstrates 100% deficiency of said NHR component.

The NHR component to be modified can be any NHR component known to the person skilled in the art. Preferred NHR components to be modified are selected from the group of: KU70, KU80, MRE11, RAD50, RAD51, RAD52, XRS2, SIR4, LIG4, or homologues thereof. More preferred NHR components to be modified are KU70 and KU80, hdfA and hdfB or homologues thereof. The most preferred NHR component to be modified is KU70 or hdfA, or a homologue thereof. Preferably, the host cell according to the invention comprises a polynucleotide encoding an NHR component comprising a disruption or deletion as described in WO2005/095624. Methods to obtain such host cell are known to the skilled person and are extensively described in WO2005/095624. Preferably, the ratio NHR/HR in the NHR deficient host cell according to the invention is decreased by at least 10%, more preferably at least 20%, more preferably at least 30%, more preferably at least 40%, more preferably at least 50%, more preferably at least 100%, more preferably at least 200%, and even more preferably at least 1000%, as compared to the non-deficient parent host cell, when assayed under identical conditions.

Alternatively, or in combination with a deficiency of an NHR component, the host cell according to the invention has the expression level of at least one gene involved in HR up regulated compared to the expression level of the same gene in the cell where the host cell originates from. This can be achieved by increasing the expression level of a gene encoding a component involved in HR and/or by increasing the expression level of a component involved in HR and/or by (temporarily) increasing the activity of the component involved in HR.

Alternatively, or in combination with modulation of the NHR/HR ratio as described here above, the methods described in WO2007/115886 and WO2007/115887 may be used to positively select host cells wherein the polynucleotide of interest is integrated by homologous recombination and/or to de-select cells wherein integration has occurred by non-homologous recombination. WO2007/115886 and WO2007/115887 describe the use of (additional) selection markers for such selection or de-selection. An example of such selection is the selective killing by diphtheria toxin A of cells where integration has taken place by non-homologous recombination (WO2007/115887).

Modification of a polynucleotide is herein defined as any event resulting in a change in the sequence of the polynucleotide. A modification is construed as one or more modifications. Modification may be accomplished by the introduction (insertion), substitution or removal (deletion) of one or more nucleotides in the nucleotide sequence or a regulatory element required for the transcription or translation of the polynucleotide. For example, nucleotides may be inserted or removed so as to result in the introduction of a stop codon, the removal of a start codon or a change or a frame-shift of the open reading frame of the polynucleotide. The modification of a sequence or a regulatory element thereof may be accomplished by site-directed or random mutagenesis, DNA shuffling methods, DNA reassembly methods, gene synthesis (see for example Young and Dong, (2004), Nucleic Acids Research 32, (7) electronic access nar.oupjournals.org/cgi/reprinU32/7/e59 or Gupta et al. (1968), Proc. Natl. Acad. Sci USA, 60: 1338-1344; Scarpulla et al. (1982), Anal. Biochem. 121: 356-365; Stemmer et al. (1995), Gene 164: 49-53), or PCR generated mutagenesis in accordance with methods known in the art.

Examples of random mutagenesis procedures are well known in the art, such as for example chemical (NTG for example) mutagenesis or physical (UV for example) mutagenesis. Examples of directed mutagenesis procedures are the QuickChange™ site-directed mutagenesis kit (Stratagene Cloning Systems, La Jolla, CA), the 'The Altered Sites® II in vitro Mutagenesis Systems' (Promega Corporation) or by overlap extension using PCR as described in Gene. 1989 Apr 15;77(1):51-9. (Ho SN, Hunt HD, Horton RM, Pullen JK, Pease LR "Site-directed mutagenesis by overlap extension using the polymerase chain reaction") or using PCR as described in Molecular Biology: Current Innovations and Future Trends. (Eds. A.M. Griffin and H.G.Griffin. ISBN 1-898486-01-8;1995 Horizon Scientific Press, PO Box 1, Wymondham, Norfolk, U.K.).

Preferred methods of modification are based on techniques of gene replacement, gene deletion, or gene disruption. For example, in the gene disruption method, a polynucleotide corresponding to the endogenous polynucleotide is mutagenized in vitro to produce a defective polynucleotide which is then transformed into the parent cell to produce a defective polynucleotide. By homologous recombination, the defective polynucleotide replaces the endogenous polynucleotide. It may be desirable that the defective polynucleotide also encodes a marker, which may be used for selection of transformants in which the nucleic acid sequence has been modified. In cases of deletion or replacement of the endogenous polynucleotide, an appropriate DNA sequence has to be introduced at the target locus to be deleted or replaced. The appropriate DNA sequence is preferably present on a cloning vector. Preferred integrative cloning vector comprises a DNA fragment, which is homologous to the polynucleotide to be deleted or replaced for targeting the integration of the cloning vector to this pre-determined locus. In order to promote targeted integration, the cloning vector is preferably linearized prior to transformation of the host cell. Preferably, linearization is performed such that at least one but preferably either end of the cloning vector is flanked by sequences homologous to the DNA sequence to be deleted or replaced.

Alternatively or in combination with other mentioned techniques, a technique based on in vivo recombination of cosmids in *E. coli* can be used, as described in: A rapid method for efficient gene replacement in the filamentous fungus *Aspergillus nidulans* (2000) Chaveroche, M-K., Ghico, J-M. and d'Enfert C; Nucleic acids Research, vol 28, no 22.

Alternatively, modification, wherein said host cell is deficient in the production of a polynucleotide may be performed by established anti-sense techniques using a nucleotide sequence complementary to the nucleic acid sequence of the polynucleotide. More specifically, expression of the polynucleotide by a host cell may be reduced or eliminated by introducing a nucleotide sequence complementary to the nucleic acid sequence of the polynucleotide, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. An example of expressing an antisense-RNA is shown in Appl Environ Microbiol. 2000 February; 66(2):775-82. (Characterization of a foldase, protein disulfide isomerase A, in the protein secretory pathway of *Aspergillus niger*. Ngiam C, Jeenes D J, Punt P J, Van Den Hondel C A, Archer D B) or (Zrenner R, Willmitzer L, Sonnewald U. Analysis of the expression of potato uridinediphosphate-glucose pyrophosphorylase and its inhibition by antisense RNA. Planta. (1993); 190(2):247-52).

Furthermore, modification, downregulation or inactivation of the gene may be obtained via the RNA interference (RNAi) technique (FEMS Microb. Lett. 237 (2004): 317-324). In this method identical sense and antisense parts of the nucleotide sequence, which expression is to be affected, are cloned behind each other with a nucleotide spacer in between, and inserted into an expression vector. After such a molecule is transcribed, formation of small nucleotide fragments will lead to a targeted degradation of the mRNA, which is to be affected. The elimination of the specific mRNA can be to various extends. The RNA interference techniques described in WO2008/053019, WO2005/05672A1, WO2005/026356A1, Oliveira et al., "Efficient cloning system for construction of gene silencing vectors in *Aspergillus niger*" (2008) Appl Microbiol and Biotechnol 80 (5): 917-924 and/or Barnes et al., "siRNA as a molecular tool for use in *Aspergillus niger*" (2008) Biotechnology Letters 30 (5): 885-890 may be used for downregulation, modification or inactivation of the gene.

Following modification of a polynucleotide, the obtained strains are screened for deficiency of the product encoded by the polynucleotide. The down and/or up regulation of the expression level of a polynucleotide can be monitored by quantifying the amount of corresponding mRNA present in a cell by Northern analysis (Sambrook and Russell (2001) "Molecular Cloning: A Laboratory Manual ($3^{rd}$ edition), Cold Spring Harbor Laboratory, Cold Spring Harbor Laboratory Press, New York.) for example and/or by quantifying the amount of corresponding protein present in a cell by western blotting or ELISA, for example. The difference in mRNA amount may also be quantified by DNA array analysis (Eisen, M. B. and Brown, P. O. DNA arrays for analysis of gene expression. Methods Enzymol. 1999:303:179-205).

Deficiency of a host cell is herein defined as a phenotypic feature wherein the cell produces less of the product encoded by the modified polynucleotide and/or has a reduced expression level of a modified polynucleotide (i.e. reduced mRNA level) and/or has a decreased specific (protein) activity of the product encoded by the modified polynucleotide and combinations of these possibilities as compared to the parent cell comprising the un-modified polynucleotide.

According to the invention, the substantially homologous DNA domain is a DNA domain or locus (terms used interchangeably herein) which in its native state comprises an endogenous gene capable of high level expression. The term "endogenous" gene is herein defined as a naturally occurring copy of a gene in the genome of the organism in question.

It is generally known that the expression level of an integrated recombinant gene can vary greatly depending on the genomic locus where that gene is integrated. The advantage of using highly expressed DNA domains for integration of recombinant genes to be expressed is that these DNA domains are at least capable of supporting high level expression of the endogenous gene. It is therefore likely that such DNA domains will also support high level expression of an integrated recombinant gene. Previously, it was determined that integration in the glaA locus of *A. niger* and integration in the penicillin cluster of *P. chrysogenum* provides higher expression levels per gene copy as compared to integration in some other genomic loci (see WO9846772). In this context it will be understood that a gene capable of high level expression is defined as a gene which, when expressed at maximum level, produces an mRNA that constitutes at least 0.1% of the total mRNA population, preferably at least 0.5% of the total mRNA and most preferably at least 1% of the total mRNA. Examples of such highly expressible endogenous genes of which the DNA domains in which they are contained are particularly suitable as substantially homologous DNA domains according to the invention are genes encoding glycolytic enzymes, amylolytic enzymes, cellulolytic enzymes and/or antibiotic biosynthetic enzymes. Even more preferred are loci comprising genes involved in industrial processes and known to be expressed at high level such as glucoamylase genes, TAKA amylase genes, cellobiohydrolase genes and penicillin biosynthetic genes.

Preferably, the at least two substantially homologous DNA domains of the host cell according to the invention are loci of glaA or are loci of amyA or are loci of amyB or are fragments or homologues of these loci. More preferred loci are the glaA, amyA and amyB loci of *Aspergillus*. Even more preferred loci are the glaA, and amyB loci of *Aspergillus niger*. Even more preferred loci are the glaA, amyBI and amyBII loci of *Aspergillus niger* CBS 513.88 (gene naming as in WO2005/095624). Even more preferred loci are the glaA, amyBI and amyBII loci (nucleotide sequence of glaA gene (An03g06550) and its genomic context a.o. can be derived from www.ncbi.nlm.nih.gov/; idem for amyBI gene sequence (An12g06930) and amyBII gene sequence (An05g021 00) or are fragments or homologues of these loci.

For purposes of the invention, the terms "homology" and "identity" are used interchangeably. The degree of homology (identity) between two nucleic acid sequences is herein preferably determined by the BLAST program. Software for performing BLAST analyses is publicly available through the National Center for Biotechnology Information www.ncbi.nlm.nih.gov/).The BLAST algorithm parameters W, T, and X determine the sensitivity and speed of the alignment. The BLAST program uses as defaults a wordlength (W) of 11, the BLOSUM62 scoring matrix (see Henikoff & Henikoff, Proc. Natl. Acad. Sci. USA 89: 10915 (1989)) alignments (B) of 50, expectation (E) of 10, M=5, N=−4, and a comparison of both strands.

According to the invention, the highly expressed endogenous gene is preferably inactivated in each copy of the DNA domain in the host cell according to the invention in cases where the expression of the endogenous gene is not required. In such cases the inactivation of the high level expression of the endogenous gene releases energy and resources which can further be utilized for the expression of the polynucleotide of interest. Moreover, in case both a desired compound to be produced by integration of the polynucleotide of interest and the enzyme encoded by the endogenous gene are secreted enzymes, inactivation of the endogenous enzyme will result in more pure preparations of the desired enzyme. Preferably the endogenous gene is inactivated by means of an irreversible deletion of at least part of the endogenous gene in order to exclude reversion of the inactivation. More preferably the inactivation of the endogenous gene is effected by an irreversible deletion which comprises at least part of the promoter and upstream activating sequences. This is particularly advantageous in cases where the expression of a desired gene encoding an enzyme to be produced by integration of the recombinant DNA molecule is driven from a promoter derived from the endogenous gene because it will eliminate competition for potentially limiting transcription factors required for expression of the desired gene.

The polynucleotide of interest may be any polynucleotide. The polynucleotide of interest may be obtained from any prokaryotic, eukaryotic, or other source. Preferably, the polynucleotide of interest and promoter associated with it are homologous to the host cell, resulting in a recombinant host cell being a self-clone.

According to the invention, the polynucleotide of interest may be a variant, optimized polynucleotide comprising an optimized terminator sequence, such as for example described in WO2006 077258. The polynucleotide of interest may be a partly synthetic polynucleotide or an entirely synthetic nucleic acid sequence. The polynucleotide of interest may be optimized in its codon use, preferably according to the methods described in WO2006/077258 and/or WO2008/000632, which are herein incorporated by reference. WO2008/000632 addresses codon-pair optimization. Codon-pair optimisation is a method wherein the nucleotide sequences encoding a polypeptide have been modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

Accordingly, according to the invention, the polynucleotide of interest is preferably a codon optimized polynucleotide.

The polynucleotide preferably comprises a coding sequence and may be comprised in a nucleic acid construct and/or in a vector, further comprising a promoter and control sequences to facilitate, cloning, transformation, expression and/or production of the compound encoded by the polynucleotide of interest.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence. The term "coding sequence" as defined herein is a sequence, which is transcribed into mRNA and translated into a polypeptide. The boundaries of the coding sequence are generally determined by the ATG start codon at the 5' end of the mRNA and a translation stop codon sequence terminating the open reading frame at the 3'end of the mRNA. A coding sequence can include, but is not limited to, DNA, cDNA, and recombinant nucleic acid sequences.

The term "control sequences" is defined herein to include all components, which are necessary or advantageous for the expression of a polypeptide. Each control sequence may be native or foreign to the nucleic acid sequence encoding the polypeptide. Such control sequences include, but are not limited to, a leader, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription terminator. At a minimum, the control sequences include a promoter, and transcriptional and translational stop signals.

The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the production of a polypeptide.

The control sequence may be an appropriate promoter sequence, a nucleic acid sequence, which is recognized by a host cell for expression of the nucleic acid sequence. The promoter sequence contains transcriptional control sequences, which mediate the expression of the polypeptide. The promoter may be any nucleic acid sequence, which shows transcriptional activity in the cell including mutant, truncated, and hybrid promoters, and may be obtained from genes encoding extracellular or intracellular polypeptides either homologous or heterologous to the host cell.

As promoter will also be understood the 5' non-coding region (between promoter and translation start) for translation after transcription into mRNA, cis-acting transcription control elements such as enhancers, and other nucleotide sequences capable of interacting with transcription factors.

The promoter may be the promoter natively associated with the coding sequence to be expressed. The promoter may also be a constitutive or inducible promoter foreign to the coding sequence to be expressed. Examples of suitable promoters for use in mammalian cells are e.g. described in Sambrook and Russell, supra. Examples of suitable promoters for use in yeasts include e.g. glycolytic promoters.

Examples of preferred inducible promoters that can be used are a starch-, copper-, oleic acid-inducible promoters.

Preferably, the promoter is selected from the group, which includes but is not limited to promoters obtained from the genes encoding *A. oryzae* TAKA amylase, *Rhizomucor miehei* aspartic proteinase, *A. niger* neutral alpha-amylase, *A. niger* acid stable alpha-amylase, *A. niger* or *A. awamori* glucoamylase (glaA), *R. miehei* lipase, *A. oryzae* alkaline protease, *A. oryzae* triose phosphate isomerase, *A. nidulans* acetamidase, the NA2-tpi promoter (a hybrid of the promoters from the genes encoding *A. niger* neutral alpha-amylase and *A. oryzae* triose phosphate isomerase, WO03/008575), and mutant, truncated, and hybrid promoters thereof. Particularly preferred promoters for use in filamentous fungal cells are a promoter, or a functional part thereof, from a protease gene; e.g., from the *F. oxysporum* trypsin-like protease gene (U.S. Pat. No. 4,288,627), *A. oryzae* alkaline protease gene (alp), *A. niger* pacA gene, *A. oryzae* alkaline protease gene, *A. oryzae* neutral metalloprotease gene, *A. niger* aspergillopepsin protease pepA gene, or *F. venenatum* trypsin gene, *A. niger* aspartic protease pepB gene.

A single appropriate promoter sequence may be used as control sequence for expression of the polynucleotide of interest, or multiple distinct promoter sequences may be used as control sequences for expression of the polynucleotide of interest. If multiple distinct promoter sequences are used, preferably at least two distinct promoter sequences are each operably linked to a polynucleotide of interest, according to WO2008/098933.

The control sequence may also be a suitable transcription terminator sequence, a sequence recognized by a filamentous fungal cell to terminate transcription. The terminator sequence is operably linked to the 3' terminus of the nucleic acid sequence encoding the polypeptide. Any terminator, which is functional in the cell, may be used in the present invention.

Preferred terminators for filamentous fungal cells are obtained from the genes encoding *A. oryzae* TAKA amylase, *A. niger* glucoamylase (glaA), *A. nidulans* anthranilate synthase, *A. niger* alpha-glucosidase, trpC gene and *Fusarium oxysporum* trypsin-like protease.

The control sequence may also be a suitable leader sequence, a non-translated region of a mRNA which is important for translation by the filamentous fungal cell. The leader sequence is operably linked to the 5' terminus of the nucleic acid sequence encoding the polypeptide. Any leader sequence, which is functional in the cell, may be used in the present invention.

Preferred leaders for filamentous fungal cells are obtained from the genes encoding *A. oryzae* TAKA amylase and *A. nidulans* triose phosphate isomerase and *A. niger* glaA.

Other control sequences may be isolated from the *Penicillium* IPNS gene, or pcbC gene, the beta tubulin gene. All the control sequences cited in WO 01/21779 are contemplated to be envisioned for use in the present invention.

The control sequence may also be a polyadenylation sequence, a sequence which is operably linked to the 3' terminus of the nucleic acid sequence and which, when transcribed, is recognized by the filamentous fungal cell as a signal to add polyadenosine residues to transcribed mRNA. Any polyadenylation sequence, which is functional in the cell, may be used in the present invention.

Preferred polyadenylation sequences for filamentous fungal cells are obtained from the genes encoding *A. oryzae* TAKA amylase, *A. niger* glucoamylase, *A. nidulans* anthranilate synthase, *Fusarium oxysporum* trypsin-like protease and *A. niger* alpha-glucosidase.

Preferably, the DNA construct comprises the polynucleotide of interest encoding a compound of interest, a promoter DNA sequence as described here above, and preferred control sequences such as:
- one translational termination sequence orientated in 5' towards 3' direction selected from the following list of sequences: TAAG, TAGA and TAAA, preferably TAAA, and/or
- one translational initiator coding sequence orientated in 5' towards 3' direction selected from the following list of sequences: GCTACCCCC; GCTACCTCC; GCTACCCTC; GCTACCTTC; GCTCCCCCC; GCTCCCTCC; GCTCCCCTC; GCTCCCTTC; GCTGCCCCC; GCTGCCTCC; GCTGCCCTC; GCTGCCTTC; GCTTCCCCC; GCTTCCTCC; GCTTCCCTC; and GCTTCCTTC, preferably GCT TCC TTC, and/or
- one translational initiator sequence selected from the following list of sequences: 5'-mwChkyCAAA-3'; 5'-mwChkyCACA-3' or 5'-mwChkyCAAG-3', using ambiguity codes for nucleotides: m (A/C); w (A/T); y (C/T); k (G/T); h (A/C/T), preferably 5'-CACCGTCAAA-3' or 5'-CGCAGTCAAG-3'.

In the context of this invention, the term "translational initiator coding sequence" is defined as the nine nucleotides immediately downstream of the initiator or start codon of the open reading frame of a DNA coding sequence. The initiator or start codon encodes for the AA methionine. The initiator codon is typically ATG, but may also be any functional start codon such as GTG.

In the context of this invention, the term "translational termination sequence" is defined as the four nucleotides starting from the translational stop codon at the 3' end of the open reading frame or nucleotide coding sequence and oriented in 5' towards 3' direction.

In the context of this invention, the term "translational initiator sequence" is defined as the ten nucleotides immediately upstream of the initiator or start codon of the open reading frame of a DNA sequence coding for a polypeptide. The initiator or start codon encodes for the AA methionine. The initiator codon is typically ATG, but may also be any functional start codon such as GTG. It is well known in the art that uracil, U, replaces the deoxynucleotide thymine, T, in RNA.

The polynucleotide of interest encoding a compound of interest, or DNA construct comprising the polynucleotide of interest and control sequences described above may be joined together to produce a recombinant expression vector which may include one or more convenient restriction sites to allow for insertion or substitution of optional polynucleotide sequences.

Alternatively, the polynucleotide of interest may be expressed by inserting the sequence or a nucleic acid construct comprising polynucleotide of interest into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus), which can be conveniently subjected to recombinant DNA procedures and can bring about the expression of the polynucleotide of interest. The choice of the vector will typically depend on the compatibility of the vector with host cell into which the vector is to be introduced. The vectors may be linear or closed circular plasmids. The vector may be an autonomously replicating vector, i.e., a vector, which exists as an extrachromosomal entity, the replication of which is independent of chromosomal replication, e.g., a plasmid, an extrachromosomal element, a minichromosome, or an artificial chromosome. An autonomously maintained cloning vector may comprise the AMA1-sequence (see e.g. Aleksenko and Clutterbuck (1997), Fungal Genet. Biol. 21: 373-397).

Alternatively, the vector may be one which, when introduced into the host cell, is integrated into the genome and replicated together with the chromosome(s) into which it has been integrated. Preferably, the integrative cloning vector comprises a DNA fragment, which is homologous to a DNA sequence in a predetermined target locus in the genome of the host cell for targeting the integration of the cloning vector to this predetermined locus. In order to promote targeted integration, the cloning vector is preferably linearized prior to transformation of the host cell. Linearization is preferably performed such that at least one but preferably either end of the cloning vector is flanked by sequences homologous to the target locus. The length of the homologous sequences flanking the target locus is preferably at least 30 bp, preferably at least 50 bp, preferably at least 0.1 kb, even preferably at least 0.2 kb, more preferably at least 0.5 kb, even more preferably at least 1 kb, most preferably at least 2 kb.

The vector system may be a single vector or plasmid or two or more vectors or plasmids, which together contain the total DNA to be introduced into the genome of the filamentous fungal cell, or a transposon.

The vectors preferably contain one or more selectable markers, which permit easy selection of transformed cells. Using the method of co-transformation, one vector may contain the selectable marker whereas another vector may contain the polynucleotide of interest or the nucleic acid construct of interest; the vectors are simultaneously used for transformation of the host cell. The host cell according to the invention has the ability that co-transformation efficiency can be very high, up to 100% (see example 12.2).

A selectable marker is a gene the product of which provides for biocide or viral resistance, resistance to heavy metals, prototrophy to auxotrophs, and the like. A selectable marker for use in a filamentous fungal host cell may be selected from the group including, but not limited to, amdS (acetamidase), argB (ornithine carbamoyltransferase), bar (phosphinothricinacetyltransferase), bleA (phleomycin binding), hygB (hygromycinphosphotransferase), niaD (nitrate reductase), pyrG (orotidine-5'-phosphate decarboxylase), sC (sulfate adenyltransferase), and trpC (anthranilate synthase), as well as equivalents from other species. Preferred for use in an *Aspergillus* and *Penicillium* cell are the amdS (EP 635574 B1, WO 97/06261) and pyrG genes of *A. nidulans* or *A. oryzae* and the bar gene of *Streptomyces hygroscopicus*. More preferably an amdS gene is used, even more preferably an amdS gene from *A. nidulans* or *A. niger*. A most preferred selection marker gene is the *A. nidulans* amdS coding sequence fused to the *A. nidulans* gpdA promoter (see EP 635574 B1). AmdS genes from other filamentous fungi may also be used (WO 97/06261).

The procedures used to ligate the elements described above to construct the recombinant expression vectors of the present invention are well known to one skilled in the art (see, e.g., Sambrook and Russell, supra; and Ausubel et al., *Current Protocols in Molecular Biology*, Wiley InterScience, NY, 1995).

Preferably, the host cell according to the invention comprises, in addition to adapted DNA domains and optionally increased efficiency of targeted integration, a polynucleotide selected from the group of: glaA, amyA, amyBI, amyBII, oahA, toxin associated polynucleotide and prtT, said polynucleotide comprising a modification, wherein the host cell is deficient in the product encoded by the polynucleotide comprising the modification, compared to the parent cell it originates from when cultivated under comparable conditions. Modification is defined as earlier herein.

Preferably, the host cell according to the invention additionally comprises a modification of Sec61. Deficiency of a host cell is herein defined, as previously herein, as a phenotypic feature wherein the cell produces less of the product encoded by the modified polynucleotide and/or has reduced expression level of the modified polynucleotide (i.e. reduced mRNA level) and/or has decreased specific (protein) activity of the product encoded by the modified polynucleotide or combinations of these features as compared to the parent cell comprising the un-modified polynucleotide.

Preferably, the host cell according to the invention demonstrates at least 5% deficiency of at least one of glaA, amyA, amyBI, amyBII, oahA, toxin associated polynucleotide or prtT, more preferably at least 10% deficiency, more preferably at least 20% deficiency, more preferably at least 30% deficiency, more preferably at least 40% deficiency, more preferably at least 50% deficiency, more preferably at least 60% deficiency, more preferably at least 70% deficiency, more preferably at least 80% deficiency, more preferably at least 90% deficiency, more preferably at least 95% deficiency, more preferably at least 97% deficiency, more preferably at least 99% deficiency. Most preferably, the host cell demonstrates 100% deficiency of at least one of glaA, amyA, amyBI, amyBII, oahA, toxin associated polynucleotide or prtT.

The advantage of the deficiency of one or more polypeptides selected from the group of glucoamylase (glaA), acid stable alpha-amylase (amyA), neutral alpha-amylase (amyBI and amyBII) and oxalic acid hydrolase (oahA) in the production of a compound of interest is that energy and resources are not utilized for these by-products. This energy and resources can be used for the production of a compound encoded by the polynucleotide of interest. Furthermore, downstream processing of a compound of interest is simplified since there are fewer by-products present.

Oxalic acid hydrolase (oahA) is a component of the synthesis pathway of oxalic acid in many host cells. A host cell deficient in oahA will be deficient in oxalic acid. Oxalic acid is an unwanted by-product in many applications such as food-applications. Furthermore, oxalic acid lowers the pH of the medium cultivations of host cell producing this component, resulting in lowered yields; i.e. yield is increased in oxalic acid deficient host cells. It is therefore advantageous if the host cell according to the invention is deficient in oahA. OahA deficient host cells and preferred methods of producing said host cells are extensively described in WO 2000/50576 and WO2004/070022. A preferred method to produce an oahA deficient host cell is the recombinant method of disruption described in WO 2000/50576. Preferably, the host cell according to the invention is deficient in oahA. Preferably, the oahA is a fungal oahA. More preferably, the oahA is the oahA from *Aspergillus*. Even more preferably the oahA is the oahA from *Aspergillus niger*. Even more preferably the oahA is the oahA from *Aspergillus niger* CBS 513.88. Most preferably, the oahA comprises the sequence of An10g00820.

prtT is a transcriptional activator of proteases in eukaryotic cells. Several fungal transcriptional activators of proteases have been recently described in WO 00/20596, WO 01/68864, WO 2006/040312 and WO 2007/062936. These transcriptional activators were isolated from *Aspergillus niger* (*A. niger*), *Aspergillus fumigatus* (*A. fumigatus*), *Penicillium chrysogenum* (*P. chrysogenum*) and *Aspergillus oryzae* (*A. oryzae*). These transcriptional activators of protease genes can be used to improve a method for producing a polypeptide in a fungal cell, wherein the polypeptide is sensitive for protease degradation. When the host cell is deficient in prtT, the host cell will produce less proteases that are under transcriptional control of prtT. It is therefore advantageous when the host cell according to the invention is deficient in prtT. prtT deficient hosts and preferred methods to produce these hosts are extensively described in WO 01/68864, WO 2006/040312. WO 01/68864 and WO 2006/040312 describe recombinant and classic methods to disrupt the prtT coding sequence. WO 2007/062936 describes disruption of the prtT binding site in a protease promoter. Disruption of the binding site impedes binding of prtT to the binding site. Consequently, the transcription of the protease is not activated by prtT and less protease is produced.

Preferably, the host cell according to the invention comprises a polynucleotide encoding prtT, said polynucleotide comprising a modification, wherein the host cell is deficient in the production of prtT compared to the parent cell it originates from when cultivated under comparable conditions. Preferably, the prtT is a fungal prtT. More preferably, the prtT is the prtT from *Aspergillus*. Even more preferably the prtT is the prtT from *Aspergillus niger*. Even more preferably the prtT is the prtT from *Aspergillus niger* CBS 513.88. Most preferably, the prtT comprises the sequence of An04g06940.

The term "glucoamylase" (glaA) is identical to the term "amyloglucosidase" and is defined herein as an enzyme having dextrin 6-alpha-D-glucanohydrolase activity which catalyses the endo hydrolysis of 1,6-alpha-D-glucoside linkages at points of branching in chains of 1,4-linked alpha-D-glucose residues and terminal 1,4-linked alpha-D-glucose residues. Glucoamylase activity can be measured as AGIU/ml by determining the liberation of paranitrofenol from the substrate p-nitrophenyl-a-D-glucopyranoside (Sigma). This results in a yellow colour, whose absorbance can be measured at 405 nm using a spectrophotometer. 1 AGIU is the quantity of enzyme, which produces 1 μmole of glucose per minute at pH 4.3 and 60° C. from a soluble starch substrate. In WO98/46772 additional details of the assay can be found.

Preferably, the host cell according to the invention comprises a polynucleotide encoding glaA, said polynucleotide comprising a modification, wherein the host cell is deficient in the production of glaA compared to the parent cell it originates from when cultivated under comparable conditions. Preferably, the glaA is a fungal glaA. More preferably, the glaA is the glaA from *Aspergillus*. Even more preferably the glaA is the glaA from *Aspergillus niger*. Even more preferably the glaA is the glaA from *Aspergillus niger* CBS 513.88. Most preferably, the glaA comprises the sequence of An03g06550.

The term "alpha-amylase" is defined herein as 1,4-alpha-D-glucan glucanohydrolase activity which catalyzes the endohydrolysis of polysaccharides with three or more alpha-1,4-linked glucose units in the presence of water to malto-oligosaccharides. To determine the (neutral) alpha-amylase activity, the Megazyme cereal alpha-amylase kit is used (Megazyme, CERALPHA alpha amylase assay kit, catalogus. ref. K-CERA, year 2000-2001), according a protocol of the supplier. The measured activity is based on hydrolysis of non-reducing-endblocked ρ-nitrophenyl maltoheptaoside in the presence of excess glucoamylase and α-glucosidase at a pH of 7.0. The amount of formed ρ-nitrophenol is a measure for alpha-amylase activity present in a sample.

The term "acid stable alpha-amylase" (amyA) is defined herein as an enzyme having alpha-amylase activity with optimal activity in the acid pH range. To determine the acid stable alpha-amylase activity, also the Megazyme cereal alpha-amylase kit is used (Megazyme, CERALPHA alpha amylase assay kit, catalogus. ref. K-CERA, year 2000-2001), according a protocol of the supplier but at an acid pH. The measured activity is based on hydrolysis of non-reducing-endblocked ρ-nitrophenyl maltoheptaoside in the presence of excess glucoamylase and α-glucosidase at a pH of 4.5. The amount of formed ρ-nitrophenol is a measure for acid stable alpha-amylase activity present in a sample.

Preferably, the host cell according to the invention comprises a polynucleotide encoding AmyA, said polynucleotide comprising a modification, wherein the host cell is deficient in amyA compared to the parent cell it originates from when cultivated under comparable conditions. Preferably, the amyA is a fungal amyA. More preferably, the amyA is the amyA from *Aspergillus*. Even more preferably the amyA is the amyA from *Aspergillus niger*. Even more preferably the amyA is the amyA from *Aspergillus niger* CBS 513.88. Most preferably, the amyA comprises the sequence of An11g03340.

The term "neutral alpha-amylase activity" (amy) is defined herein as an enzyme having alpha-amylase activity with optimal activity in the neutral pH range.

Preferably, the host cell according to the invention comprises a polynucleotide encoding AmyB, said polynucleotide comprising a modification, wherein the host cell is deficient in amyBI and/or amyBII compared to the parent cell it originates from when cultivated under comparable conditions. More preferably, the host cell is deficient in amyBI and amyBII. Preferably, the amyB a is a fungal amyB. More preferably, the amyB is the amyB from *Aspergillus*. Even more preferably the amyB is the amyBI from *Aspergillus niger*. Even more preferably the amyB is the amyBI from *Aspergillus niger* CBS 513.88. Most preferably, the amyBI comprises the sequence of An12g06930. Even more preferably the amyB is the amyBII from *Aspergillus niger*. Even more preferably the amyB is the amyBII from *Aspergillus niger* CBS 513.88. Most preferably, the amyBII comprises the sequence of An05g02100.

The term toxin associated polynucleotide is defined herein as a gene cluster, a multitude of genes, a gene or part thereof encoding a compound, or biochemical pathway responsible for the biosynthesis or secretion of at least one toxin or toxin intermediate compound. Said compound may e.g. be a polypeptide, which may be an enzyme.

A number of host cells, especially fungi, which are used as host cells in the production of polypeptides of interest possesses genes encoding enzymes involved in the biosynthesis of various toxins. For example, cyclopiazonic acid, kojic acid, 3-nitropropionic acid and aflatoxins are known toxins, which are formed in, e.g., *Aspergillus flavus*. Similarly, trichothecenes are formed in a number of fungi, e.g., in *Fusarium* sp. such as *Fusarium venenatum* and in *Trichoderma* and ochratoxin may be produced by *Aspergillus*. Recently, sequencing of the genome of an industrial *Aspergillus niger* host strain revealed a fumonisin gene cluster (Pel et al., "Genome sequencing and analysis of the versatile cell factory *Aspergillus niger* CBS 513.88". Nat Biotechnol. 2007 February; 25 (2):221-231). The formation of such toxins during the fermentation of compounds of interest is highly undesirable as these toxins may present a health hazard to operators, customers and the environment. Consequently, a toxin deficient host cell enables toxin-free production of a compound of interest. The toxin-free compound is easier to produce since no toxin has to be removed from the product. Furthermore, the regulatory approval procedure for the compound is easier.

Preferably, the host cell according to the invention comprises a toxin associated polynucleotide encoding a compound (which may e.g. be a polypeptide which may be an enzyme) or biochemical pathway, said toxin associated polynucleotide comprising a modification, wherein the host cell is deficient in the production of said toxin or a toxin intermediate compound compared to the parent cell it originates from when cultivated under comparable conditions. Preferably, the toxin or toxin intermediate compound is a fungal toxin or toxin intermediate compound. More preferably, the toxin or toxin intermediate compound is a toxin or toxin intermediate compound from *Aspergillus*. Even more preferably the toxin or the toxin intermediate compound is a toxin or toxin intermediate compound from *Aspergillus niger*. Even more preferably the toxin or toxin intermediate compound is a toxin or toxin intermediate compound from *Aspergillus niger* CBS 513.88. Even more preferably, the toxin or the toxin intermediate compound is fumonisin or a fumonisin intermediate compound. Even more preferably, the toxin or the toxin intermediate compound is ochratoxin or an ochratoxin intermediate compound. Most preferably, the toxin or the toxin intermediate compound is ochratoxin or fumonisin or an ochratoxin or a fumonisin intermediate compound.

Preferably, the toxin associated polynucleotide encodes a compound (which may e.g. be a polypeptide which may be an enzyme) or a biochemical pathway which is involved in the production of a fungal toxin or toxin intermediate compound. More preferably, a toxin or toxin intermediate compound from *Aspergillus*. Even more preferably, a toxin or toxin intermediate compound from *Aspergillus niger*. Even more preferably, a toxin or toxin intermediate compound from *Aspergillus niger* CBS 513.88. Even more preferably, a fumonisin or a fumonisin intermediate compound. Even more preferably, a fumonisin-B or a fumonisin-B intermediate compound. Even more preferably, a fumonisin-B2 or a fumonisin-B2 intermediate compound. Even more preferably, the toxin associated polynucleotide comprises the sequence of the fumonisin cluster from An01g06820 until An01g06930. Most preferably, the toxin associated polynucleotide comprises the sequence of An01g06930.

In another preferred embodiment, the toxin associated polynucleotide encodes a compound (which may e.g. be a polypeptide which may be an enzyme) or a biochemical pathway which is involved in ochratoxin or an ochratoxin intermediate compound. More preferably, an ochratoxin A or an ochratoxin A intermediate compound. More preferably, the toxin associated polynucleotide comprises the sequence of the cluster from An15g07880 until An15g07930. Most preferably, the toxin associated polynucleotide comprises the sequence of An15g07910 and/or the sequence of An15g07920.

Preferably, the host cell according to the invention comprises at least one toxin associated polynucleotide encoding a compound (which may e.g. be a polypeptide which may be an enzyme) or biochemical pathway, said toxin associated polynucleotide comprising at least one modification, wherein the host cell is deficient in the production of a toxin or, toxin intermediate compound compared to the parent cell it originates from when cultivated under comparable conditions.

More preferably, the host cell according to the invention comprises two toxin associated polynucleotides, said two toxin associated polynucleotides each comprising at least one modification, wherein the host cell is preferably deficient in the production of fumonisin and ochratoxin compared to the parent cell it originates from when cultivated under comparable conditions.

Even more preferably, the host cell according to the invention comprises three or more toxin associated polynucleotides said three or more toxin associated polynucleotides each comprising at least one modification, wherein the host cell is preferably deficient in the production of fumonisin, ochratoxin and at least one additional toxin or toxin intermediate compound compared to the parent cell it originates from when cultivated under comparable conditions.

Preferably, the host cell according to the invention is deficient in glaA and at least one of the components selected from the group of amyA, amyBI, amyBII, oahA, toxin associated compound and prtT, by virtue of having a modification in the polynucleotide encoding glaA and said components. More preferably, the host cell according to the invention is deficient in glaA, oahA and at least one of the components selected from the group of amyA, amyBI, amyBII, toxin associated compound and prtT Even more preferably, the host cell according to the invention is deficient in glaA, oahA, toxin associated compound and at least one of the components selected from the group of amyA, amyBI, amyBII, and prtT. Even more preferably the host cell according to the invention is deficient in glaA, oahA, amyA, amyBI, amyBII and at least one of the components selected from the group of toxin associated compound and prtT. Even more preferably the host cell according to the invention is deficient in glaA, oahA, amyA, amyBI, amyBII, prtT and toxin associated compound. Most preferably, the host cell according to the invention comprising at least two substantially homologous DNA domains suitable for integration of one or more copies of a polynucleotide of interest wherein at least one of the at least two substantially homologous DNA domains is adapted to have enhanced integration preference for the polynucleotide of interest compared to the substantially homologous DNA domain it originates from, is deficient in glaA, oahA, amyA, amyBI, amyBII, prtT and toxin associated compound and is furthermore deficient in an NHR component, preferably ku70 or a homologue thereof.

In addition to deficiency or modification of the components described here above, the host cell according to the invention may be deficient in other components, such as major proteases like pepA. Preferably, the pepA is a fungal pepA. More preferably, the pepA is the pepA from *Aspergillus*. Even more preferably the pepA is the pepA from *Aspergillus niger*. Even more preferably the pepA is the pepA from *Aspergillus niger* CBS 513.88. Most preferably, the pepA comprises the sequence of An14g04710. Preferably, the host cell according to the invention demonstrates at least 5% deficiency of pepA, more preferably at least 10% deficiency, more preferably at least 20% deficiency, more preferably at least 30% deficiency, more preferably at least 40% deficiency, more preferably at least 50% deficiency, more preferably at least 60% deficiency, more preferably at least 70% deficiency, more preferably at least 80% deficiency, more preferably at least 90% deficiency, more preferably at least 95% deficiency, more preferably at least 97% deficiency, more preferably at least 99% deficiency. Most preferably, the host cell demonstrates 100% deficiency of pepA.

Alternatively, or in combination with the deficiencies described here above, the host cell comprises an elevated unfolded protein response (UPR) compared to the wild type cell to enhance production abilities of a polypeptide of interest. UPR may be increased by techniques described in US2004/0186070A1 and/or US2001/0034045A1 and/or WO01/72783A2 and/or WO2005/123763. More specifically, the protein level of HAC1 and/or IRE1 and/or PTC2 has been modulated, and/or the SEC61 protein has been engineered in order to obtain a host cell having an elevated UPR. A preferred SEC61 modification is a modification which results in a one-way mutant of SEC61; i.e. a mutant wherein the de novo synthesized protein can enter the ER via SEC61, but the protein cannot leave the ER via SEC61. Such modifications are extensively described in WO2005/123763. Most preferably, the SEC 61 modification is the S376W mutation in which Serine 376 is replaced by Tryptophan.

A preferred host cell according to the invention is a recombinant *Aspergillus niger* recombinant host cell for the production of a compound of interest, said host cell comprising at least two substantially homologous DNA domains suitable for integration of one or more copies of a polynucleotide of interest wherein at least one of the at least two substantially homologous DNA domains is adapted to have enhanced integration preference for the polynucleotide of interest compared to the substantially homologous DNA domain it originates from, and wherein the substantially homologous DNA domain where the adapted substantially homologous DNA domain originates from has a gene conversion frequency that is at least 10% higher than one of the other of the at least two substantially homologous DNA domains, wherein the adapted substantially homologous DNA domain is distinguished from the other versions of the substantially homologous DNA domains by means of a unique sequence tag and wherein the adapted substantially homologous DNA domain comprises a targeting DNA domain, wherein said targeting DNA domain comprises a sequence with enhanced integration preference and said host cell being deficient in glaA, pepA, hdfA, amyBII, amyBI, amyA, oahA, fumB, och. Preferably, said host cell has a sec61 S376W mutation, i.e. wherein the S376W mutation in which Serine 376 is replaced by Tryptophan. More preferably, said host cell additionally is deficient in prtT. Such host cell are described in examples 9, 10 and 11.

Preferably, the host cell according to the invention is a selection marker free host cell.

This situation may be obtained by counter-selection for a bidirectional dominant selection marker, such as the acetamidase gene (amdS) from *Aspergillus nidulans*. This marker can be used to select for transformants having the gene by selecting with acetamide as sole carbon and/or nitrogen source, whereas counter-selection (a term reserved hereinafter for selection for the absence of the marker gene) can be done with, for example fluoracetamide. Other bidirectional dominant selection markers which work in specific host cells can be used in an analogous fashion. The out-recombination of the bidirectional marker gene is facilitated by inserting the gene flanked by direct repeats on the incoming plasmid.

As disclosed in European patent EP0635574B1, the amdS bidirectional marker is dominant in both directions, meaning that transformed cells of any genetic background can be selected for the presence of the marker (using acetamide as sole carbon and/or sole nitrogen source). Other bidirectional markers are URA3, LYS2, pyrG, facA and the like.

The use of cells which are marker-free is more easily accepted by the regulatory authorities, and at the same time pose less burden to the energy balance of the yeast under industrial fermentation conditions.

The host cell according to the invention may be any host cell. For specific uses of a compound produced in a host cell according to the invention, the selection of the host cell may be made according to such use. Where e.g. the compound produced in a host cell according to the invention is to be used in food applications, a host cell may be selected from a food-grade organism such as *Saccharomyces cerevisiae*. Specific uses include, but are not limited to, food, (animal) feed, pharmaceutical, agricultural such as crop-protection, and/or personal care applications.

According to an embodiment, the host cell according to the invention is a eukaryotic host cell. Preferably, the eukaryotic cell is a mammalian, insect, plant, fungal, or algal cell. Preferred mammalian cells include e.g. Chinese hamster ovary (CHO) cells, COS cells, 293 cells, PerC6 cells, and hybridomas. Preferred insect cells include e.g. Sf9 and Sf21 cells and derivatives thereof. More preferably, the eukaryotic cell is a fungal cell, i.e. a yeast cell, such as *Candida, Hansenula, Kluyveromyces, Pichia, Saccharomyces, Schizosaccharomyces*, or *Yarrowia* strain. More preferably from *Kluyveromyces lactis, S. cerevisiae, Hansenula polymorpha, Yarrowia lipolytica* and *Pichia pastoris*, or a filamentous fungal cell. Most preferably, the eukaryotic cell is a filamentous fungal cell.

"Filamentous fungi" include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Thermoascus, Thielavia, Tolypocladium,* and *Trichoderma*.

Preferred filamentous fungal cells belong to a species of an *Aspergillus, Chrysosporium, Penicillium, Talaromyces, Fusarium* or *Trichoderma* genus, and most preferably a species of *Aspergillus niger, Aspergillus awamori, Aspergillus foetidus, Aspergillus sojae, Aspergillus fumigatus, Talaromyces emersonii, Aspergillus oryzae, Chrysosporium lucknowense, Fusarium oxysporum, Trichoderma reesei* or *Penicillium chrysogenum*. A more preferred host cell is *Aspergillus niger*. When the host cell according to the invention is an *Aspergillus niger* host cell, the host cell preferably is CBS 513.88, CBS124.903 or a derivative thereof. Most preferably, the recombinant host cell according to the invention is a host cell as described in the examples herein, preferably a host cell as in examples 4-11.

Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL) *Aspergillus niger* CBS 513.88, CBS124.903, *Aspergillus oryzae* ATCC 20423, IFO 4177, ATCC 1011, CBS205.89, ATCC 9576, ATCC14488-14491, ATCC 11601, ATCC12892, *P. chrysogenum* CBS 455.95, *Penicillium citrinum* ATCC 38065, *Penicillium chrysogenum* P2, *Talaromyces emersonii* CBS 124.902, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* ATCC44006 and derivatives thereof.

According to another embodiment, the host cell according to the invention is a prokaryotic cell. Preferably, the prokaryotic host cell is bacterial cell. The term "bacterial cell" includes both Gram-negative and Gram-positive microorganisms. Suitable bacteria may be selected from e.g. *Escherichia, Anabaena, Caulobactert, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus* or *Streptomyces*. Preferably, the bacterial cell is selected from the group consisting of *B. subtilis, B. amyloliquefaciens, B. licheniformis, B. puntis, B. megaterium, B. halodurans, B. pumilus, G. oxydans, Caulobactert crescentus* CB 15, *Methylobacterium extorquens, Rhodobacter sphaeroides, Pseudomonas zeaxanthinifaciens, Paracoccus denitrificans, E. coli, C. glutamicum, Staphylococcus carnosus, Streptomyces lividans, Sinorhizobium melioti* and *Rhizobium radiobacter.*

The host cell according to the invention can conveniently be used for various purposes, e.g. the production of a compound of interest and for expression cloning such as described in WO1999/032617 and WO2008/138835. These patent applications describe the convenience of expression cloning using filamentous fungal cells as host cells.

The present invention also provides for a method for the production of a recombinant host cell for the production of a compound of interest, said host cell comprising at least two substantially homologous DNA domains suitable for integration of one or more copies of a polynucleotide of interest, comprising adapting a substantially homologous DNA domain with higher gene conversion ratio compared to another substantially homologous DNA domain to have enhanced integration preference for the polynucleotide of interest compared to the substantially homologous DNA domain it originates from, preferably by providing the substantially homologous DNA domain with higher gene conversion frequency with a targeting DNA domain, wherein said targeting DNA domain comprises a sequence with enhanced integration preference.

Adapting a substantially homologous DNA domain with higher gene conversion ratio compared to another substantially homologous DNA domain to have enhanced integration preference for the polynucleotide of interest compared to the substantially homologous DNA domain it originates from, may be performed by any means known to the person skilled in the art. Preferably, the adapted substantially homologous DNA domain is partly or completely unique within the genome of the host. As is shown in example 3, an amplicon in *A. niger* is adapted using the glucoamylase promoter sequence, which was previously removed from the genome. This resulted in a substantially homologous DNA domain with a unique targeting sequence. The promoter and terminator parts of a polynucleotide of interest function as DNA sequences suitable for integration in the adapted substantially homologous DNA domain after transformation as is shown in example 11. All means for performing these experiments for the person skilled in the art are described herein and in Sambrook and Russel, supra.

Preferably, the method for the production of a recombinant host cell for the production of a compound of interest further comprises the steps of:

a. transforming the cell obtained with adapted substantially homologous DNA domain with higher gene conversion ratio with a polynucleotide of interest, b. selecting or screening for cells having at least one copy of the polynucleotide of interest integrated into at least one of the substantially homologous DNA domains, c. propagating the cells obtained in (b) and selecting or screening for cells having at least one copy of said polynucleotide of interest integrated in an additional copy of a substantially homologous DNA domain.

More preferably, the method for the production of the recombinant host cell for the production of a compound of interest is a method as described in the examples herein.

Methods for transformation of cells are well-known to the person skilled in the art. Any such method may be used for the purpose of the present invention. Transformation may involve a process consisting of protoplast formation, transformation of the protoplasts, and regeneration of the cell wall in a manner known per se. Suitable procedures for transformation of *Aspergillus* cells are described in EP 238 023 and Yelton et al., 1984, Proceedings of the National Academy of Sciences USA 81: 1470-1474. Suitable procedures for transformation of *Aspergillus* and other filamentous fungal host cells using *Agrobacterium tumefaciens* are described in e.g. Nat Biotechnol. 1998 September; 16(9):839-42. Erratum in: Nat Biotechnol 1998 November; 16(11):1074. *Agrobacterium tumefaciens*-mediated transformation of filamentous fungi. de Groot M J, Bundock P, Hooykaas P J, Beijersbergen A G. Unilever Research Laboratory Vlaardingen, The Netherlands. A suitable method of transforming *Fusarium* species is described by Malardier et al., 1989, Gene 78: 147156 or in WO 96/00787. Other method can be applied such as a method using biolistic transformation as described in: Biolistic transformation of the obligate plant pathogenic fungus, *Erysiphe graminis* f. sp. *hordei*. Christiansen S K, Knudsen S, Giese H. Curr Genet. 1995 December; 29(1):100-2. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

A number of routine techniques are available to the skilled person for determining which of the obtained transformants has an integration of a recombinant DNA molecule in one of its DNA domains.

In a further step a selected transformant is propagated and from its progeny a strain is selected in which at least two of the DNA domains comprise the integrated polynucleotide of interest. This means that strains are selected in which the DNA domain comprising the integrated polynucleotide of interest is multiplied, either through gene conversion with an "empty" DNA domain or through amplification. Such gene conversion and/or amplification events occur spontaneously at low frequency. The exact frequency at which these events occur may depend on a number of variables including the host cell in question and the number, the length and the extent of homology of the DNA domains. These frequencies are however sufficiently high to enable one to screen and select for strains in which these events have occurred using analysis techniques known to the person skilled in the art. Strains in which the DNA domain comprising the integrated polynucleotide of interest is multiplied can e.g. be identified by simply screening for strains with higher production levels of the product encoded by the polynucleotide of interest, or alternatively by analysing their genotype by e.g. the "DNA-flag" test as outlined above.

The method for the production of a recombinant host cell according to the invention may comprise additional steps in which one of the strains in which multiplication of the DNA domain comprising the integrated polynucleotide of interest has occurred is propagated and wherein form its progeny strains are selected in which additional copies of the DNA domains comprise the integrated polynucleotide of interest. These strains may then again be subjected to this procedure until a strain is obtained in which each of the DNA domains comprises the integrated polynucleotide of interest.

Preferably, step (c) of the method here above is repeated until at least three of the substantially homologous DNA domains have at least one copy of the polynucleotide of interest integrated. More preferably, step (c) is repeated until at least four of the substantially homologous DNA domains have at least one copy of the polynucleotide of interest integrated. Even more preferably, step (c) is repeated until at least five of the substantially homologous DNA domains have at least one copy of the polynucleotide of interest integrated. Even more preferably, step (c) is repeated until at least six of the substantially homologous DNA domains have at least one copy of the polynucleotide of interest integrated. Most preferably, step (c) is repeated until each of the substantially homologous DNA domains has at least one copy of the polynucleotide of interest integrated.

The present invention also provides for a method for the production of a compound of interest, comprising:
  a. cultivating a host cell according to the invention under conditions conducive to the production of said compound; and
  b. recovering the compound of interest from the cultivation medium.

The present invention also provides for a method for the production of a compound of interest comprising:
  a. cultivating a recombinant host cell under conditions conducive to the production of said compound, said host cell comprising at least two substantially homologous DNA domains suitable for integration of one or more copies of a polynucleotide of interest, wherein at least one of the at least two substantially homologous DNA domains is adapted to have enhanced integration preference for the polynucleotide of interest compared to the substantially homologous DNA domain it originates from, and wherein at least two of the substantially homologous DNA domains have at least one copy of a polynucleotide of interest integrated; and
  b. recovering the compound of interest from the cultivation medium.

In the production methods according to the present invention, the host cells are cultivated in a nutrient medium suitable for production of the compound of interest, e.g. polypeptide or metabolite using methods known in the art. Examples of cultivation methods which are not construed to be limitations of the invention are submerged fermentation, surface fermentation on solid state and surface fermentation on liquid substrate. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the coding sequence to be expressed and/or the polypeptide to be isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide or metabolite is secreted into the nutrient medium, the polypeptide or metabolite can be recovered directly from the medium. If the polypeptide or metabolite is not secreted, it can be recovered from cell lysates.

Polypeptides may be detected using methods known in the art that are specific for the polypeptides. These detection methods may include use of specific antibodies, formation of an enzyme product, or disappearance of an enzyme substrate.

The resulting compound of interest e.g. polypeptide or metabolite may be recovered by the methods known in the art. For example, the polypeptide or metabolite may be recovered from the nutrient medium by conventional procedures including, but not limited to, centrifugation, filtration, extraction, spray-drying, evaporation, or precipitation.

Polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulphate precipitation), SDS-PAGE, or extraction (see, e.g., Protein Purification, J.-C. Janson and Lars Ryden, editors, VCH Publishers, New York, 1989).

Preferably, the host cell in the methods according to the invention is a selection marker free host cell as described earlier herein.

Preferably, the host cell in the methods according to the invention is a fungal host cell as described earlier herein.

Preferably, the host cell in the methods according to the invention is a filamentous fungal host cell as described earlier herein.

The compound of interest of the present invention can be any biological compound. The biological compound may be any biopolymer or metabolite. The biological compound may be encoded by a single polynucleotide or a series of polynucleotides composing a biosynthetic or metabolic pathway or may be the direct result of the product of a single polynucleotide or products of a series of polynucleotides. The biological compound may be native to the host cell or heterologous.

The term "heterologous biological compound" is defined herein as a biological compound which is not native to the cell; or a native biological compound in which structural modifications have been made to alter the native biological compound.

The term "biopolymer" is defined herein as a chain (or polymer) of identical, similar, or dissimilar subunits (monomers). The biopolymer may be any biopolymer. The biopolymer may for example be, but is not limited to, a nucleic acid, polyamine, polyol, polypeptide (or polyamide), or polysaccharide.

The biopolymer may be a polypeptide. The polypeptide may be any polypeptide having a biological activity of interest. The term "polypeptide" is not meant herein to refer to a specific length of the encoded product and, therefore, encompasses peptides, oligopeptides, and proteins. Polypeptides further include naturally occurring allelic and engineered variations of the above-mentioned polypeptides and hybrid polypeptides. The polypeptide may native or may be heterologous to the host cell. The polypeptide may be a collagen or gelatin, or a variant or hybrid thereof. The polypeptide may be an antibody or parts thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, ceramidases, epoxide hydrolase, aminopeptidase, acylases, aldolase, hydroxylase, aminopeptidase, lipase. The polypeptide may be an enzyme secreted extracellularly. Such enzymes may belong to the groups of oxidoreductase, transferase, hydrolase, lyase, isomerase, ligase, catalase, cellulase, chitinase, cutinase, deoxyribonuclease, dextranase, esterase. The enzyme may be a carbohydrase, e.g. cellulases such as endoglucanases, β-glucanases, cellobiohydrolases or β-glucosidases, hemicellulases or pectinolytic enzymes such as xylanases, xylosidases, mannanases, galactanases, galactosidases, pectin methyl esterases, pectin lyases, pectate lyases, endo polygalacturonases, exopolygalacturonases rhamnogalacturonases, arabanases, arabinofuranosidases, arabinoxylan hydrolases, galacturonases, lyases, or amylolytic enzymes; hydrolase, isomerase, or ligase, phosphatases such as phytases, esterases such as lipases, proteolytic enzymes, oxidoreductases such as oxidases, transferases, or isomerases. The enzyme may be a phytase. The enzyme may be an aminopeptidase, asparaginase, amylase, carbohydrase, carboxypeptidase, endo-protease, metallo-protease, serine-protease catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, protein deaminase, invertase, laccase, lipase, mannosidase, mutanase, oxidase, pectinolytic enzyme, peroxidase, phospholipase, polyphenoloxidase, ribonuclease, transglutaminase, or glucose oxidase, hexose oxidase, monooxygenase.

In the methods of the present invention, a polypeptide can also be a fused or hybrid polypeptide to which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide.

Techniques for producing fusion polypeptides are known in the art, and include, ligating the coding sequences encoding the polypeptides so that they are in frame and expression of the fused polypeptide is under control of the same promoter (s) and terminator. The hybrid polypeptides may comprise a combination of partial or complete polypeptide sequences obtained from at least two different polypeptides wherein one or more may be heterologous to the host cell.

The biopolymer may be a polysaccharide. The polysaccharide may be any polysaccharide, including, but not limited to, a mucopolysaccharide (e.g., heparin and hyaluronic acid) and nitrogen-containing polysaccharide (e.g., chitin). In a more preferred option, the polysaccharide is hyaluronic acid.

The polynucleotide of interest according to the invention may encode an enzyme involved in the synthesis of a primary or secondary metabolite, such as organic acids, carotenoids, (beta-lactam) antibiotics, and vitamins. Such metabolite may be considered as a biological compound according to the present invention.

The term "metabolite" encompasses both primary and secondary metabolites; the metabolite may be any metabolite. Preferred metabolites are citric acid, gluconic acid and succinic acid.

The metabolite may be encoded by one or more genes, such as in a biosynthetic or metabolic pathway. Primary metabolites are products of primary or general metabolism of a cell, which are concerned with energy metabolism, growth, and structure. Secondary metabolites are products of secondary metabolism (see, for example, R. B. Herbert, The Biosynthesis of Secondary Metabolites, Chapman and Hall, New York, 1981).

The primary metabolite may be, but is not limited to, an amino acid, fatty acid, nucleoside, nucleotide, sugar, triglyceride, or vitamin.

The secondary metabolite may be, but is not limited to, an alkaloid, coumarin, flavonoid, polyketide, quinine, steroid, peptide, or terpene. The secondary metabolite may be an antibiotic, antifeedant, attractant, bacteriocide, fungicide, hormone, insecticide, or rodenticide. Preferred antibiotics are cephalosporins and beta-lactams.

The biological compound may also be the product of a selectable marker. A selectable marker is a product of a polynucleotide of interest which product provides for biocide or viral resistance, resistance to heavy metals, prototrophy to auxotrophs, and the like. Selectable markers include, but are not limited to, amdS (acetamidase), argB (ornithinecarbamoyltransferase), bar (phosphinothricinacetyltransferase), hygB (hygromycin phosphotransferase), niaD (nitratereductase), pyrG (orotidine-5'-phosphate decarboxylase), sC (sulfate adenyltransferase), trpC (anthranilate synthase), ble (phleomycin resistance protein), as well as equivalents thereof.

According to the invention, the compound of interest in the methods according to the invention is preferably a polypeptide as described herein.

Preferably, the polypeptide in the methods according to the invention is an enzyme as described herein.

According to the invention, the compound of interest in the methods according to the invention is preferably a metabolite.

According to another aspect of the invention, the adapted DNA domain of the at least two substantially homologous DNA domains of the host cell has the lowest frequency of multiplication through gene conversion and/or amplification. Different substantially homologous DNA domains revealed to have different frequencies of multiplication i.e. gene conversion frequencies. The advantage of adapting a targeting DNA domain of a substantially homologous DNA domain with the lowest frequency of multiplication is that a genetically stable host is obtained with a low frequency of recombination in a substantially homologous DNA domain.

The sequence information as provided herein should not be so narrowly construed as to require inclusion of erroneously identified bases. The specific sequences disclosed herein can be readily used to isolate the complete gene from the respective host cells which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a nucleic acid sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

The invention described and claimed herein is not to be limited in scope by the specific embodiments herein enclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In case of conflict, the present disclosure including definitions will be taken as a guide.

EXAMPLES

Strains

WT 1: This *Aspergillus niger* strain is used as a wild-type strain. This strain is deposited at the CBS Institute under the deposit number CBS 513.88.

WT 2: This *A. niger* mutant strain is derived from *A. niger* CBS 513.88 by classical strain improvement by a method as essentially as described in WO98/46772. After NTG- or UV-mutagenesis of spores of WT 1, a selection was performed for improved glucoamylase production of the mutant strains in shake flask. Several improved *A. niger* strains were identified, of which a good one produced a 3-4 fold increased glucoamylase activity levels. This mutant strain is deposited at the CBS Institute under the deposit number CBS 124.903. From shake flask and genetic analyses it was concluded that the *A. niger* CBS 124.903 strain has a 3-4 fold increased glucoamylase production accompanied by an increased (3) glaA gene copy number due to amplified glaA loci (amplicons).

GBA 300: This *A. niger* strain is a WT 2 strain comprising three modifications of the glaA amplicon. Construction of the GBA 300 strain was performed according to the methods described in WO98/46772; in this patent application it is extensively described how to delete three glaA specific DNA sequences from an *A. niger* genome containing amplicons, resulting in an amdS-negative strain with three truncated glaA amplicons. The procedure resulted in a MARKER-GENE FREE ΔglaA recombinant *A. niger* WT 2 strain, possessing finally no foreign DNA sequences at all. The three truncated glaA amplicons are designated as BamHI truncated amplicon, SalI truncated amplicon and BglII truncated amplicon.

*A. niger* Shake Flask Fermentations

*A. niger* strains were precultured in 20 ml preculture medium as described in the Examples: "*Aspergillus niger* shake flask fermentations" section of WO99/32617. After overnight growth, 10 ml of this culture was transferred to fermentation medium 1 (FM1) with 7% glucose as described in WO99/32617. This FM1 contains per liter: 25 g Caseinhydrolysate, 12.5 g Yeast extract, 1 g $KH_2PO_4$, 2 g $K_2SO_4$, 0.5 g $MgSO_4.7H_2O$, 0.03 g $ZnCl_2$, 0.02 g $CaCl_2$, 0.01 g $MnSO_4.4H_2O$, 0.3 g $FeSO_4.7H_2O$, 10 ml Pen-Strep (5000 IU/ml Pen-5 mg/ml Strep), adjusted to pH 5.6 with 4 N $H_2SO_4$. Fermentation is performed in 500 ml flasks with baffle with 100 ml fermentation broth at 34° C. and 170 rpm for the number of days indicated.

Fermentation medium 2 (FM2) is used for PLA2 fermentations and contains per liter: 82.5 g Glucose. $1H_2O$, 25 g Maldex 15 (Boom Meppel, Netherlands), 2 g Citric acid, 4.5 g $NaH_2PO_4.1H_2O$, 9 g $KH_2PO_4$, 15 g $(NH_4)_2SO_4$, 0.02 g $ZnCl_2$, 0.1 g $MnSO_4.1H_2O$, 0.015 g $CuSO_4.5H_2O$, 0.015 g $CoCl_2.6H_2O$, 1 g $MgSO_4.7H_2O$, 0.1 g $CaCl_2.2H_2O$, 0.3 g $FeSO_4.7H_2O$, 30 g MES (2-[N-Morpholino]ethanesulfonic acid), pH=6.

*A. niger* Agar Media for Toxin Measurements

Strains were cultured on the following media to test for the production of ochratoxin A (OTA) and fumonisin B2 (FB2): Czapek yeast autolysate agar (CYA) and yeast extract sucrose agar (YES) as essentially described by Frisvad and Filtenborg, 1989 (Terverticillate Penicillia: chemotaxonomy and mycotoxin production, Mycologia 81:837-861) and Frisvad and Thrane, 1993 (Liquid column chromatography of mycotoxinsm In: Betina (ed): Chromatography of mycotoxins. Techniques and applications. J. of Chromatography Library 54: 253-372 Elsevier, Amsterdam). Petri dishes were incubated for 7 days in darkness at 24° C., after which agar plugs were taken from single colonies for extraction. Extraction was done with 84% CH3CN-water and placement in an ultrasonication bath for 1 hour, after which the solvent was filtrated through a 0.45 µm PTFE filter.

Quantification was done by spiking samples with an internal standard solution to defined amounts of FB2 and OTA. LC-MS/MS was performed as described by Mogensen et al. 2010 (Production of fumonisin B2 and B4 by *Aspergillus niger* in raisins and grapes, J of Agricultural and Food Chemistry 58: 954-958) and reviewed in Nielsen et al. 2009 (Review of secondary metabolites and mycotoxins from the *Aspergillus niger* group, Anal Bioanal Chem 395: 1225-1242).

Example 1

Construction of *Aspergillus niger* GBA 301 (ΔglaA, ΔpepA)

This *A. niger* strain is a GBA 300 strain comprising a deletion of the pepA gene encoding the major extracellular aspartic protease PepA. The GBA 301 strain is constructed by using the "MARKER-GENE FREE" approach as described in EP 0 635 574. The method described in this patent is used to delete pepA specific DNA sequences in the genome of GBA 300, as described by van den Hombergh et al. (van den Hombergh J P, Sollewijn Gelpke M D, van de Vondervoort P J, Buxton F P, Visser J. (1997)—Disruption of three acid proteases in *Aspergillus niger*—effects on protease spectrum, intracellular proteolysis, and degradation of target proteins—Eur J Biochem. 247(2): 605-13). The procedure resulted in a MARKER-GENE FREE GBA 301 strain, with the pepA gene inactivated in the GBA 300 strain background.

Example 2

Construction of *Aspergillus niger* GBA 302 (ΔglaA, ΔpepA, ΔhdfA)

Figure 1:
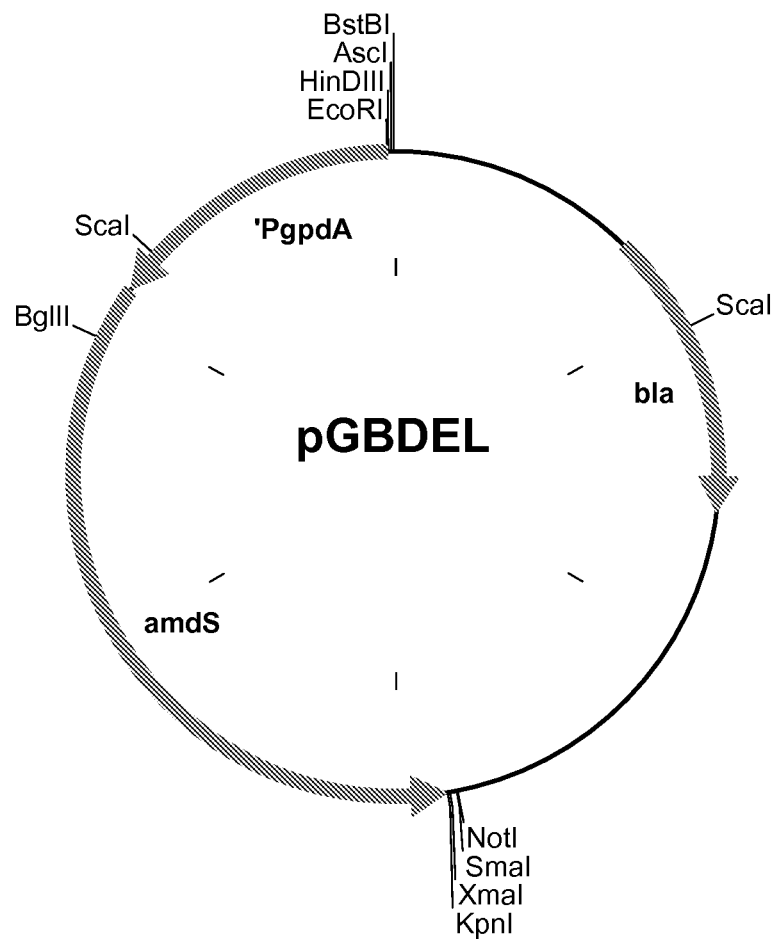
FIG. 1 depicts a physical map of replacement vector pGB-DEL. Indicated are the multiple cloning sites for cloning flanking regions relative to the amdS marker.

A gene replacement vector for hdfA were designed according to known principles and constructed according to routine cloning procedures. In essence, these vectors comprise approximately 1-2 kb flanking regions of the hdfA ORF for homologous recombination at the predestined genomic loci. In addition, they contain the *A. nidulans* bi-directional amdS selection marker, in-between direct repeats. The general design of deletion vectors was previously described in EP635574B and WO 98/46772 and use of general cloning vector pGBDEL (FIG. 1) for constructing deletion vectors was described in WO06/040312.

Figure 2:
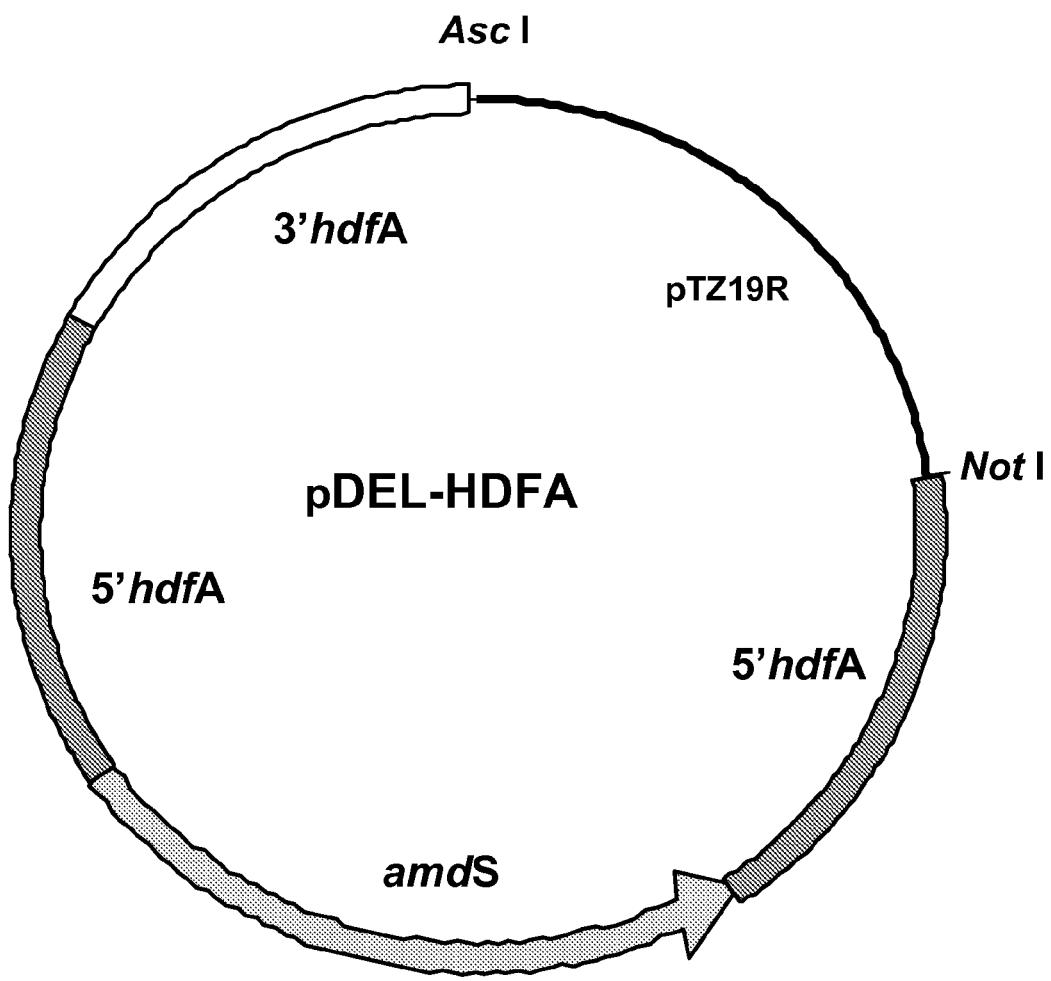
FIG. 2 depicts a physical map of replacement vector pDEL-HDFA for use to inactivate the hdfA gene in *Aspergillus niger* (*A. niger*). The replacement vector comprises the hdfA flanking regions, the amdS marker and *E. coli* DNA. The *E. coli* DNA can be removed by digestion with restriction enzymes AscI and NotI, prior to transformation of the *A. niger* strains.
Figure 3:
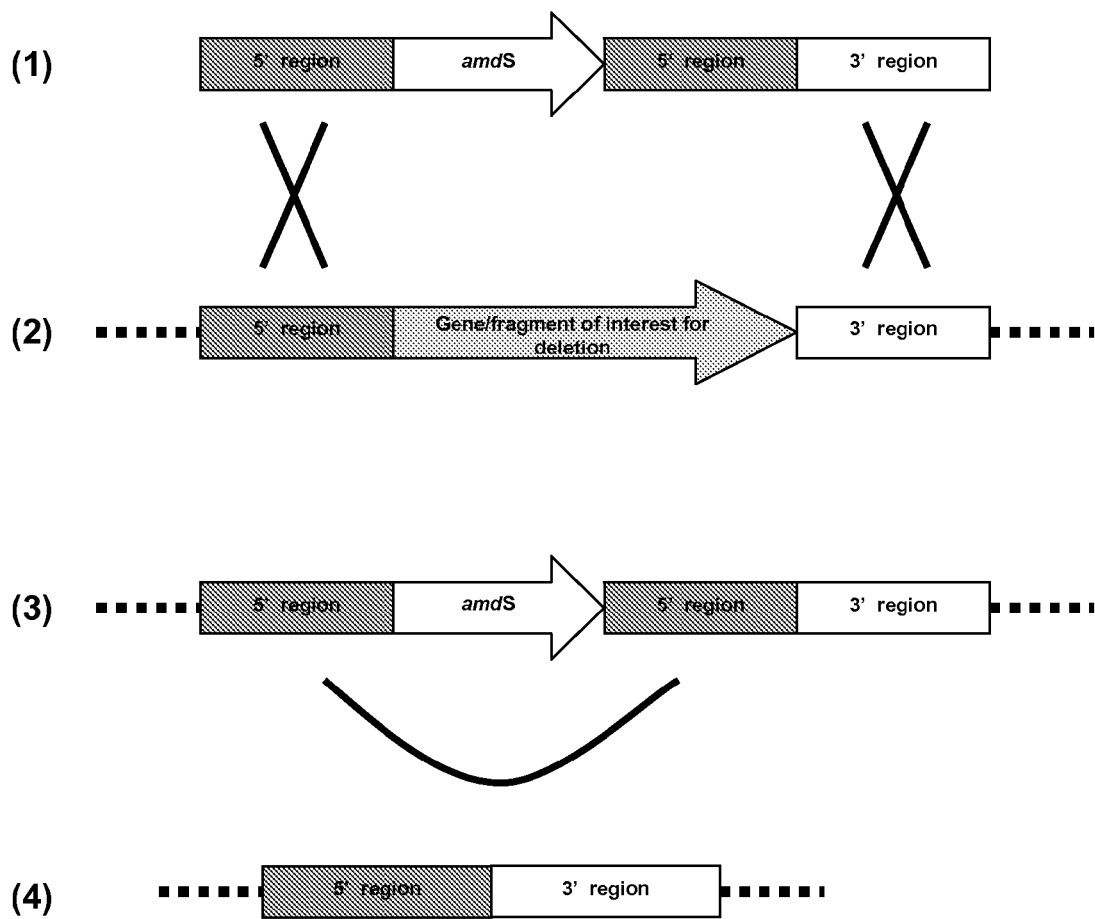
FIG. 3 depicts the strategy used to delete a gene or gene fragment from a host strain. The DNA construct used comprises the amdS selection marker flanked by homologous regions (5' and 3') of the gene to be deleted (1). This construct integrates through double homologous recombination (X) at the corresponding genomic locus (2) and replaces the genomic gene copy (3). Subsequently, recombination over the direct repeats (U) removes the amdS marker, resulting in precise excision of the gene or gene fragment to be deleted (4).

Vector pDEL-HDFA (FIG. 2) comprises approximately 1 kb flanking regions of the hdfA ORF for homologous recombination. All nucleotide sequences for *A. niger* genes and their genomic context can be derived for example from NCBI www.ncbi.nlm.nih.gov/) or EMBL www.ebi.ac.uk/embl/). Linear DNA of deletion vector pDEL-HDFA was isolated and used to transform *Aspergillus niger* GBA 301 using a method as earlier described in detail in W005/095624 to delete the hdfA gene. The method applied for gene deletion in all examples herein used linear DNA, which integrates into the genome at the homologous locus of the flanking sequences by a double cross-over, thus substituting the gene to be deleted by the amdS gene. Subsequently, the amdS marker was removed by plating on fluoro-acetamide media, to select marker-gene-free strains. The general procedure for gene disruption is depicted in FIG. 3. Strain GBA 302 was selected as a representative strain with the hdfA gene inactivated in the GBA 301 strain background.

Example 3

Construction of *Aspergillus niger* GBA 303 (ΔglaA, ΔpepA, ΔhdfA, Adapted BamHI Amplicon)

In this example, the ΔglaA amplicons with the highest frequency of gene conversion will be adapted, resulting in a unique locus for targeted integration allowing the use of a smart integration strategy. The adapted amplicon allows the flanking control sequences, such as the glucoamylase promoter and terminator in this example, to be used as targeting regions, as well.

Example 3.1

Identification of Amplicon with Highest Frequency of Gene Conversion

Figure 4:
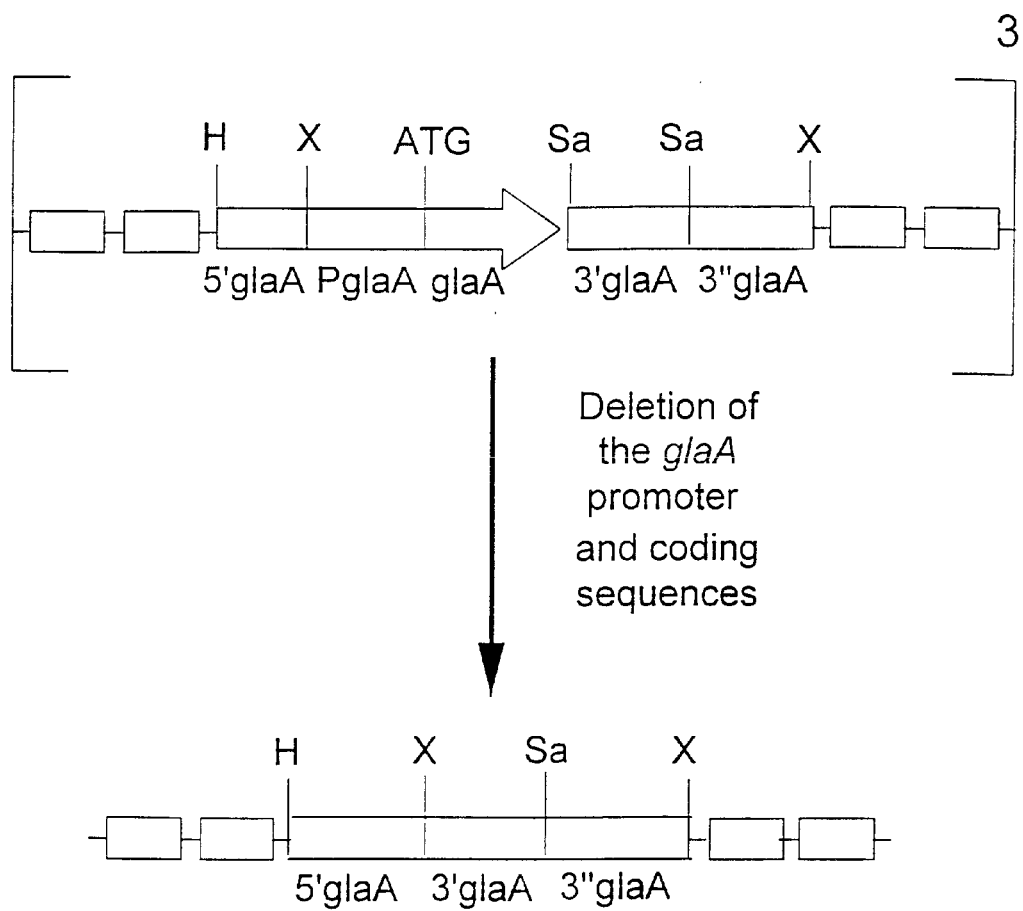
FIG. 4 depicts physical maps of the glaA (glucoamylase) loci in parental *A. niger* strain CBS 124.903 and the three truncated "X-marked" ΔglaA loci in recombinant strain GBA 300 ("X" stands for a BamHI, SalI or BglII restriction site).
Figure 5:
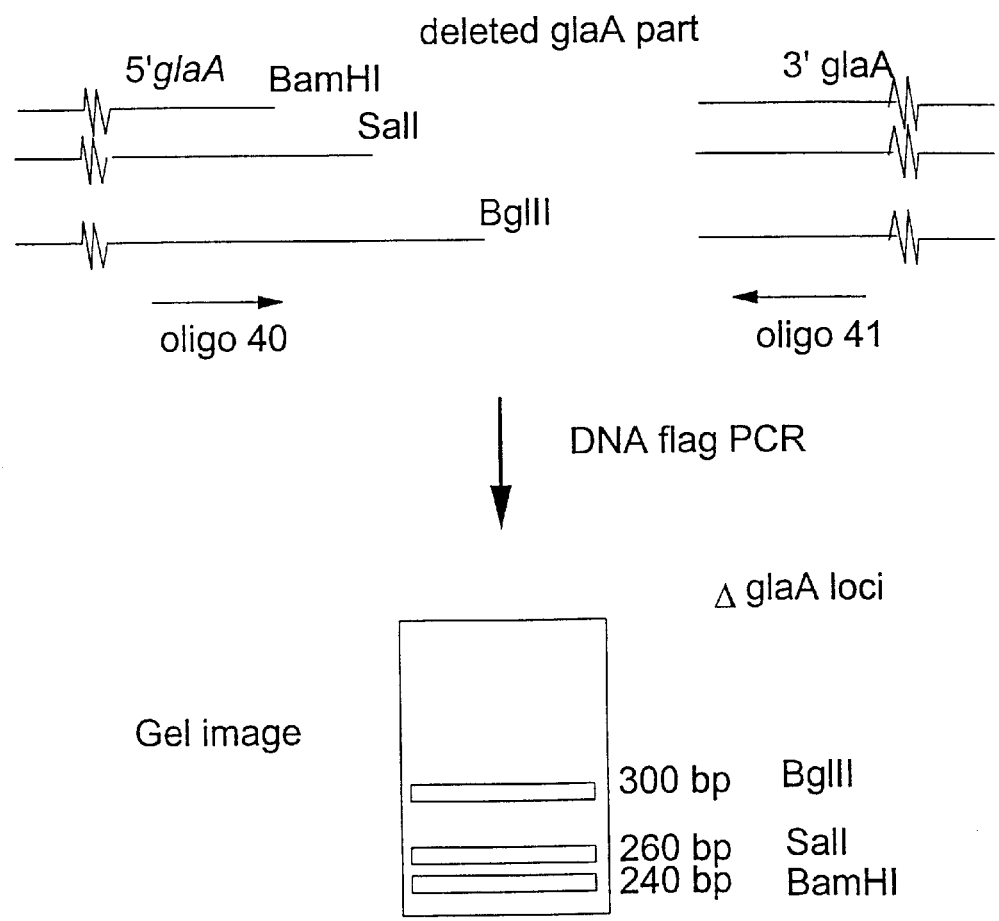
FIG. 5 depicts a schematic view of the three ΔglaA loci in the glaA DNA amplicons of *A. niger* CBS 124.903 derived recombinant strain GBA 300, each locus marked by a different restriction site (BamHI, SalI or BglII). The glaA loci each differ in length by approximately 20 to 60 bp, to be able to visualize the different truncated glaA loci by the PCR-based DNA-flag test.

Strain GBA 301 contains three modified ΔglaA loci in the genome. For all three loci, approximately 4.3 kb glaA sequences (2 kb glaA promoter and entire glaA coding sequence) have been deleted (As in FIG. 4—from WO98/46772). Since three different deletion vectors were used, each ΔglaA locus is slightly different, features which can be used to visualize each truncated ΔglaA locus by a PCR test (FIG. 5—from WO98/46772). This incorporated difference also can be used to follow gene conversion events between the truncated glaA amplicons. The three truncated glaA amplicons are designated as BamHI truncated amplicon, SalI truncated amplicon and BglII truncated amplicon and showing a band with a size of 240, 260 and 300 bp, respectively in the so-called "DNA-flag" test (FIG. 5—from WO98/46772).

From strain GBA 301, multiple phytase producing strains were produced, containing multiple phytase expression cassettes (by cotransforming pGBAAS-1 and pGBTOPFYT-1) all targeted to one of the three truncated glaA amplicons of GBA 301 (essentially as described in WO98/46772—example 1.4). The resulting strains each possess phytase cassettes in one of the three truncated glaA amplicons and are called BAM-PHY, SAL-PHY and BGL-PHY, according to the phytase cassette integration site.

Convertants with an increased phytase cassette copy number were identified for the three different strains BAM-PHY, SAL-PHY and BGL-PHY (essentially as described in WO98/46772—example 1.5). For the convertants with increased phytase copy number, the frequencies and genotypes of specific amplicons of the phytase-containing glaA amplicon were determined using the "DNA-flag" test. By analysing thousands of individual progenies of the respective strains by the "DNA-flag" test, gene conversion can be detected by deletion of a specific truncated glaA amplicon (for example SalI) paralleled by amplification of another specific truncated glaA amplicon (for example BamHI).

The results of PCR-scoring and typing of hundreds of individual progenies for the three different strains can be found in Table 1. In addition, a similar approach was followed for some isolated strains after a single gene conversion event, which contained 2 amplicons of the same type. These results of PCR-scoring hundreds of individual progenies for the three types of strains can be found in Table 2. For the three different strains, the phytase cassettes located in the BamHI amplicon can be multiplied at the highest frequency by gene conversion, both for a first and a second gene conversion event.

TABLE 1

Strains with increased copy number as a result of gene conversion as determined by the "DNA-flag" test.

| Strain | Genotype | Frequency | Genotype | Frequency |
|---|---|---|---|---|
| BAM-PHY | BamHI$^{2+}$/SalI$^+$/BglII$^-$ | 0.8% | BamHI$^{2+}$/SalI$^-$/BglII$^+$ | 0.5% |
| SAL-PHY | SalI$^{2+}$/BamHI$^+$/BglII$^-$ | 0.2% | SalI$^{2+}$/BamHI$^-$/BglII$^+$ | 0.2% |
| BGL-PHY | BglII$^{2+}$/SalI$^+$/BamHI$^-$ | 0% | BglII$^{2+}$/SalI$^-$/BamHI$^+$ | 0.1% |

TABLE 2

Strains with increased copy number as a result of a second gene conversion or amplification event as determined by the "DNA-flag" test.

| Strain | Genotype | Frequency |
|---|---|---|
| BamHI$^{2+}$/SalI$^+$/BglII$^-$ or BamHI$^{2+}$/SalI$^-$/BglII$^+$ | BamHI$^{3+}$ | 0.2% |
| SalI$^{2+}$/BamHI$^+$/BglII$^-$ or SalI$^{2+}$/BamHI$^-$/BglII$^+$ | SalI$^{3+}$ | 0.1% |
| BglII$^{2+}$/SalI$^+$/BamHI$^-$ or BglII$^{2+}$/SalI$^-$/BamHI$^+$ | BglII$^{3+}$ | 0% |

Example 3.2

Adaptation of BamHI Amplicon, which has the Highest Frequency of Gene Conversion In this part of the example, it is described how the previously removed glucoamylase promoter PglaA (upon threefold modification of the glaA loci in CBS 124.903 resulting in strain GBA300) is re-introduced at a single locus in the genome but at a different position in the amplicons to be adapted, resulting in a unique and improved locus for targeted integration.

Figure 6:
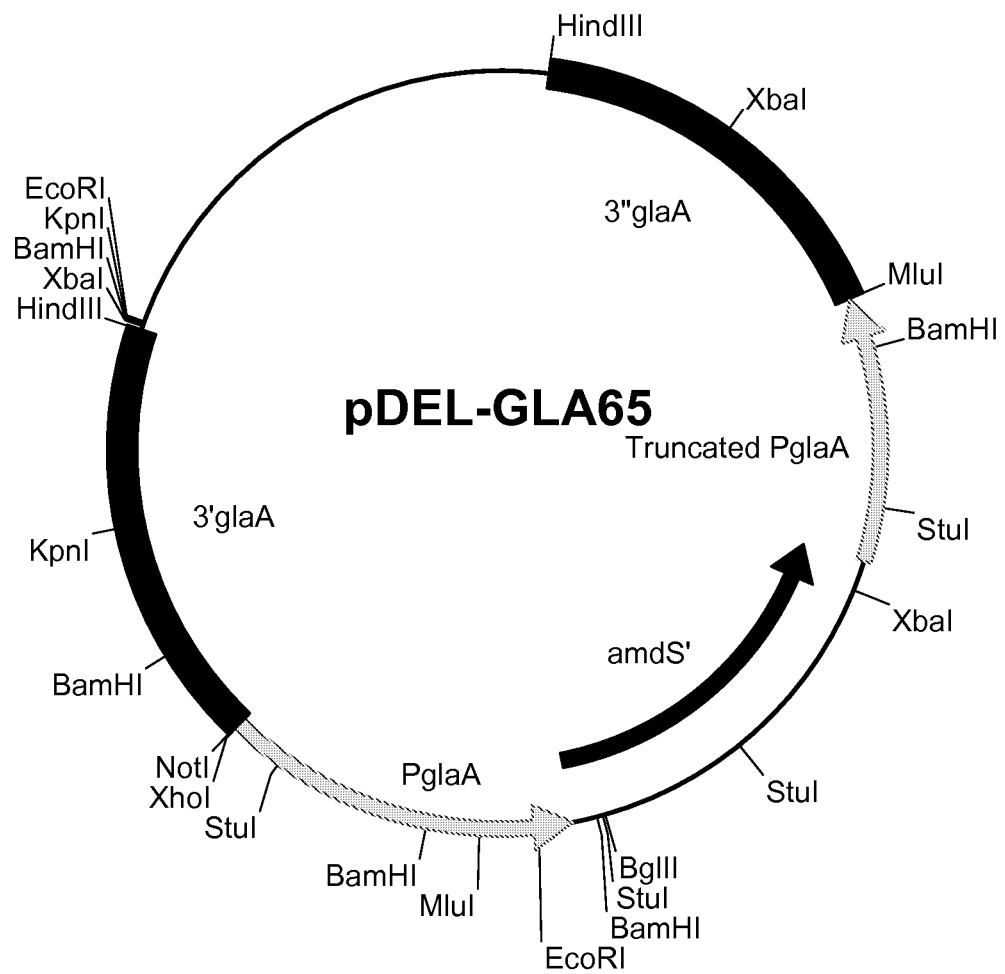
FIG. 6 depicts a physical map of vector pGBGLA-65 for use to adapt a substantially homologous DNA domain. Basically, this vector contains an amdS selection marker in between two $P_{glaA}$ fragments and the 3'glaA and 3"glaA region. The 3'glaA and 3"glaA region are used for targeting and integration into the corresponding genomic region of the ΔglaA loci. The two $P_{glaA}$ fragments are used for excision of the amdS selection marker upon counterselection as in FIG. 3. One PglaA fragment is a truncated $P_{glaA}$ promoter fragment (missing the last 600 bp of the $P_{glaA}$ promoter 3' of the MluI site), which remains present in the genome after amdS counterselection.

To be able to adapt an amplicon, a gene replacement type of vector for the ΔglaA loci was designed according to known principles and constructed according to routine cloning procedures. For this purpose, the vector pGBGLA-65 was constructed (FIG. 6). Basically, this vector contains an amdS selection marker in between two $P_{glaA}$ fragments and the 3'glaA and 3"glaA region. The 3'glaA and 3"glaA region are used for targeting and integration into the identical genomic region of the ΔglaA loci. The two $P_{glaA}$ fragments are used for looping out the amdS selection marker upon counterselection (FIG. 3). One PglaA fragment is a truncated $P_{glaA}$ promoter fragment (missing the last 600 bp of the $P_{glaA}$ promoter 3' of the MluI site), which remains present in the genome after amdS counterselection.

Figure 7:
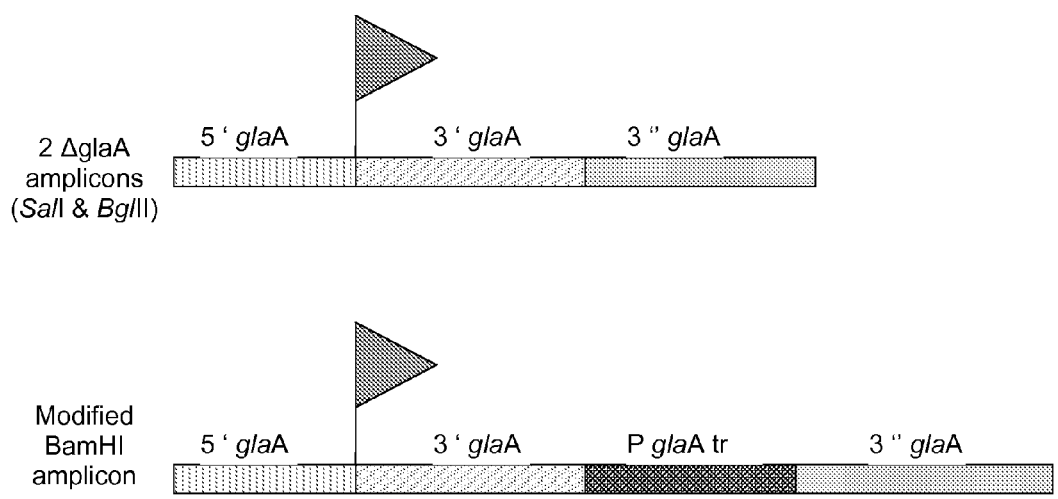
FIG. 7 depicts physical maps of the three ΔglaA loci in the glaA DNA amplicons in a strain with an adapted BamHI amplicon. The BamHI amplicon was adapted by introduction of a truncated homologous glucoamylase promoter fragment in between the homologous 3' glaA and 3" glaA loci of the genomic glaA locus.

To be able to adapt the BamHI amplicon in the genome, vector pDEL-GLA65 (FIG. 6) was digested with HindIII and gel-purified to remove the *E. coli* backbone. Linear DNA of deletion vector pDEL-GLA65 was used to transform *Aspergillus niger* GBA 302 using a method as earlier described in detail in WO05/095624. Linear DNA of pDEL-GLA65 can integrate into the amplicons at the 3' glaA and 3" glaA sequences by a double cross-over. A number of colonies were purified and analysed via PCR for presence of the three glaA-loci and integration of the cassette at the BamHI amplicon (target PCR). The targeting frequency for the BamHI amplicon was estimated at 20-30%. In total 7 strains were selected for fluoracetamide counterselection. The fluoracetamide resistant colonies were transferred to PDA and tested by "flag"-PCR. A strain was selected as a representative strain with an adapted BamHI locus, with the amdS marker correctly deleted via recombination over the PglaA repeats of the integrated pDEL-GLA65 cassette (FIG. 7). The selected strain was designated GBA 303, which represents the GBA 300 strain background with all 3 ΔglaA loci, with the pepA and the hdfA gene inactivated and the BamHI amplicon adapted. Since the entire glaA amplicons are large in size (>80 kb) and although the BamHI amplicon has been adapted (2-6 kb), still fragments with rather substantial homologous DNA domains remain present in the genome.

The sequence of the genomic region comprising a 3'-fragment and 3"-fragment of a ΔglaA amplicon (FIG. 7) can be found under SEQ ID NO: 1. The sequence of the genomic region comprising a 3'-fragment, a truncated $P_{glaA}$ promoter fragment and a 3"-fragment of the adapted BamHI amplicon can be found under SEQ ID NO: 2.

Example 3.3

Construction of Novel Integration Vectors

In EPA 0635574A1, WO98/46772 and WO99/32617 the integration and expression vectors pGBAAS-1 (pGBGLA-50 in EP0635574) and pGBTOP-8, used in targeted strain construction, and especially targeted strain construction using a single cross-over have been described. Adjustment of these integration vectors is necessary to allow specific targeting to the adapted BamHI amplicon of GBA 302 type of strains.

Figure 8:
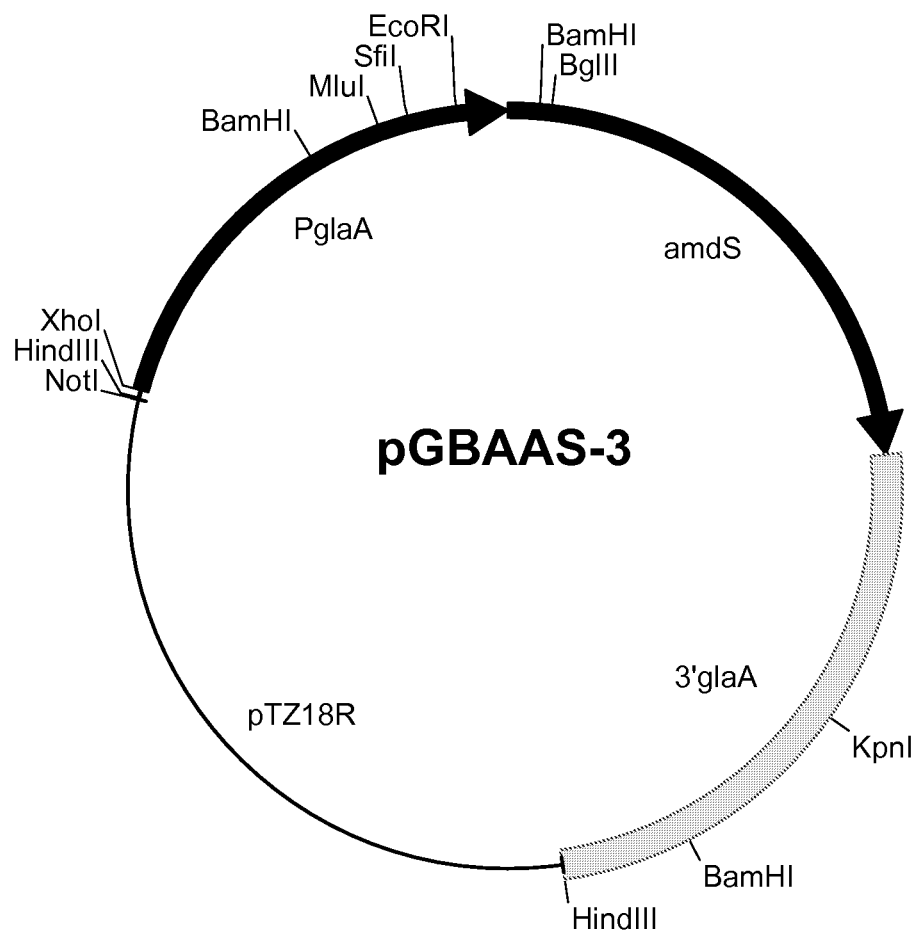
FIG. 8 depicts a physical map of a novel acetamidase selection marker and adapted BamHI amplicon targeting vector pGBAAS-3. The glaA promoter functions as targeting region and as promoter for the amdS gene
Figure 9:
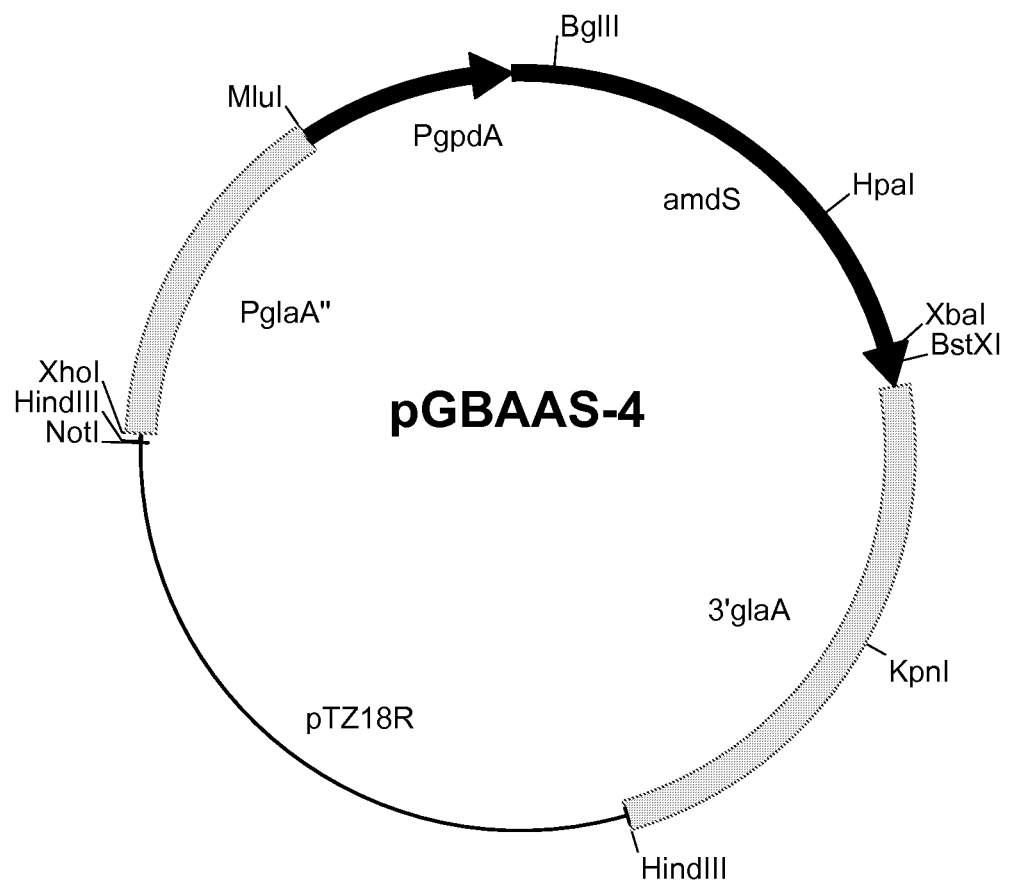
FIG. 9 depicts a physical map of a novel acetamidase selection marker and adapted BamHI amplicon targeting vector pGBAAS-4. The (truncated) glaA promoter functions as targeting region and the gpdA promoter drives the expression of the amdS gene

Of the pGBAAS-1 vector, containing the amdS marker and used in co-transformation, two different variants have been constructed for targeted integration into the adapted BamHI amplicon. A vector called pGBAAS-3 (FIG. 8) was constructed, which has the amdS marker gene expressed under control of the glucoamylase promoter $P_{glaA}$. The $P_{glaA}$ promoter has a function in driving the expression of the amdS marker gene. In addition, the $P_{glaA}$ promoter and the 3' glaA fragment function as targeting sequences, specifically for the adapted BamHI ΔglaA amplicon (FIG. 21). A second vector, called pGBAAS-4 (FIG. 9), was constructed, which contains the amdS marker cassette of pGBAAS-1 (amdS under control of the gpdA promoter). Here, a truncated $P_{glaA}$ promoter fragment and the 3' glaA fragment have a function in targeting to the adapted BamHI ΔglaA amplicon (FIG. 21).

Figure 10:
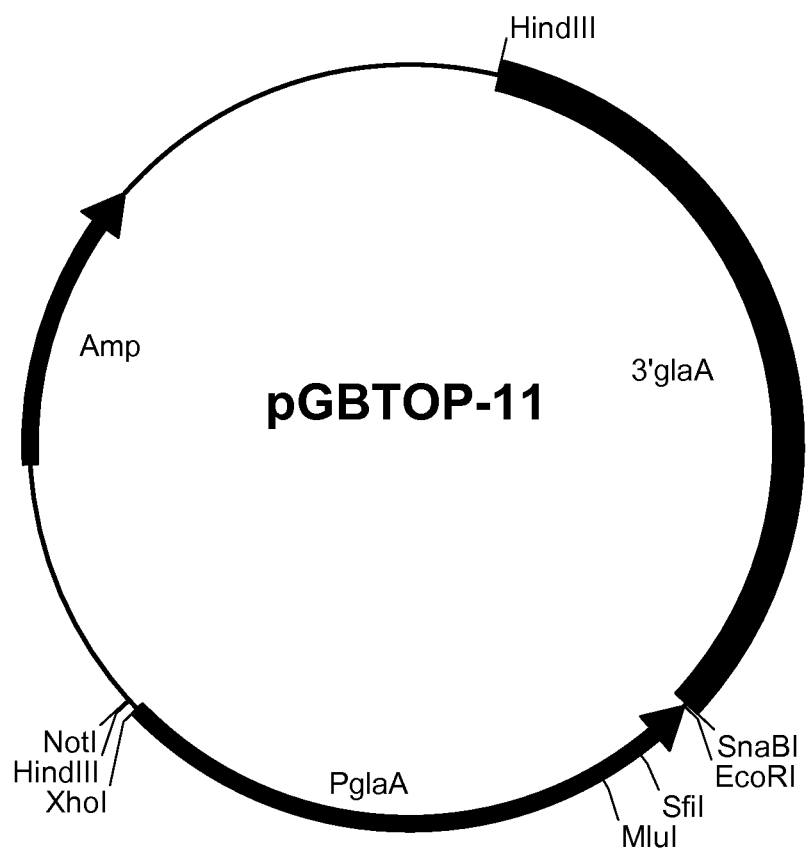
FIG. 10 depicts a physical map of a novel expression and adapted BamHI amplicon targeting vector pGBTOP-11. The HinDIII restriction enzyme can be used to linearize the vector and remove the *E. coli* part
Figure 11:
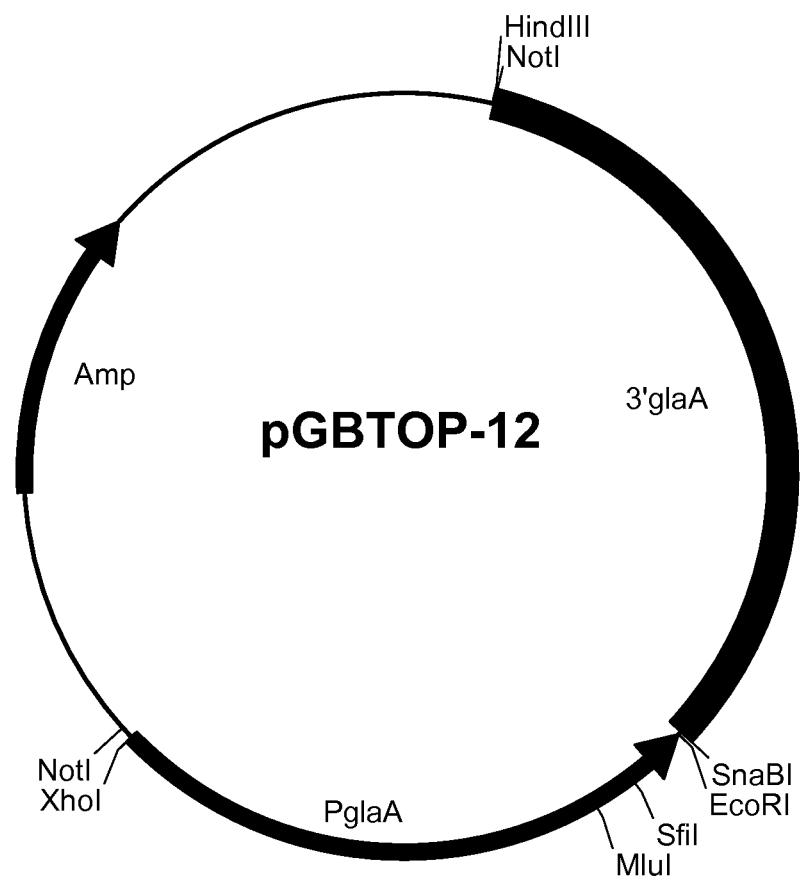
FIG. 11 depicts a physical map of a novel expression and adapted BamHI amplicon targeting vector pGBTOP-12. The NotI restriction enzyme can be used to linearize the vector and remove the *E. coli* part

For the pGBTOP type of vectors, two novel integration and expression vectors have been constructed to allow targeting to the adapted BamHI ΔglaA amplicon. The pGBTOP-11 (FIG. 10) and pGBTOP-12 (FIG. 11) vectors basically are a pGBTOP-8 vector with the 3" glaA fragment removed and with additional modification of restriction sites for *E. coli* vector removal, respectively. Here, the $P_{glaA}$ promoter and the 3' glaA terminator fragment have a double function: besides their role as promoter and terminator for expressing a gene of interest also a role in targeting to the adapted BamHI ΔglaA amplicon (FIG. 21).

Example 4

Construction of *Aspergillus niger* GBA 304 (ΔglaA, ΔpepA, ΔhdfA, Adapted BamHI Amplicon, ΔamyBII)

Figure 12:
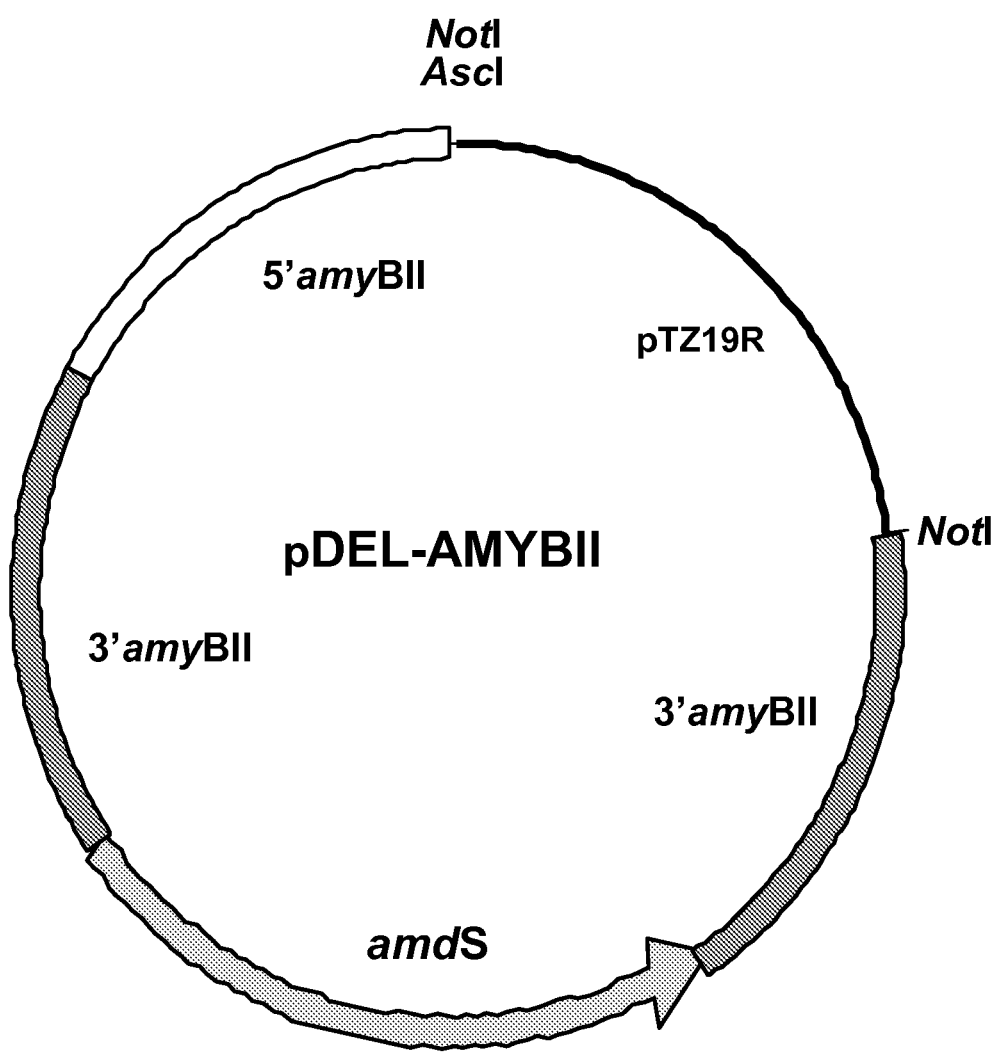
FIG. 12 depicts a physical map of replacement vector pDEL-AMYBII. Indicated are the 5' amyBII flanking region, the 3' amyBII flanking regions relative to the amdS marker. The sequence of the 3'-sequences of amyBII overlap at least a few hundred bp. The *E. coli* DNA can be removed by digestion with restriction enzyme NotI, prior to transformation of the host strain.

Gene-flanking regions of the amyBII ORF, encoding alpha-amylase, were cloned essentially as described in Example 2, resulting in vector pDEL-AMYBII (FIG. 12). Linear DNA of deletion vector pDEL-AMYBII was isolated and used to transform *Aspergillus niger* GBA 303 using a method as earlier described in WO05/095624 to delete the amyBII gene. A transformant was selected with the amyBII ORF removed upon integration of pDEL-AMYBII in the genome at the homologous amyBII locus by a double cross-over event. Subsequently, the amdS marker was removed by plating on fluoro-acetamide media, to select marker-gene-free strains. Strain GBA 304 was selected as a representative strain with the amyBII gene inactivated in the GBA 303 strain background.

Example 5

Construction of *Aspergillus niger* GBA 305 (ΔglaA, ΔpepA, ΔhdfA, Adapted BamHI Amplicon, ΔamyBII, ΔamyBI)

Gene-flanking regions of the amyBI ORF, encoding alpha-amylase, were cloned essentially as described in Example 2, resulting in vector pDEL-AMYBI (a representative picture for the layout of pDEL-AMYBI can be found in FIG. 12). Linear DNA of deletion vector pDEL-AMYBI was isolated and used to transform *Aspergillus niger* GBA 304 using a method as earlier described in WO05/095624 to delete the amyBI gene. A transformant was selected with the amyBI ORF removed upon integration of pDEL-AMYBI in the genome at the homologous amyBI locus by a double cross-over event. Subsequently, the amdS marker was removed by plating on fluoro-acetamide media, to select marker-gene-free strains. Strain GBA 305 was selected as a representative strain with the amyBI gene inactivated in the GBA 304 strain background.

Example 6

Construction of *Aspergillus niger* GBA 306 (ΔglaA, ΔpepA, ΔhdfA, Adapted BamHI Amplicon, ΔamyBII, ΔamyBI, ΔamyA)

Gene-flanking regions of the amyA ORF, encoding acid stable alpha-amylase, were cloned essentially as described in Example 2, resulting in vector pDEL-AMYA (a representative picture for the layout of pDEL-AMYA can be found in FIG. 12). Linear DNA of deletion vector pDEL-AMYA was isolated and used to transform *Aspergillus niger* GBA 305 using a method as earlier described in WO05/095624 to delete the amyA gene. A transformant was selected with the amyA ORF removed upon integration of pDEL-AMYA in the genome at the homologous amyA locus by a double cross-over event. Subsequently, the amdS marker was removed by plating on fluoro-acetamide media, to select marker-gene-free strains. Strain GBA 306 was selected as a representative strain with the amyA gene inactivated in the GBA 305 strain background.

Example 7

Construction of *Aspergillus niger* GBA 307 (ΔglaA, ΔpepA, ΔhdfA, Adapted BamHI Amplicon, ΔamyBII, ΔamyBI, ΔamyA, ΔoahA)

This *A. niger* oxalate deficient strain can be obtained by deletion of the oahA gene, encoding oxaloacetate hydrolase, which is described in detail in EP1157100 and U.S. Pat. No. 6,936,438. Strain GBA 307 was selected as a representative strain with the oahA gene inactivated in the GBA 306 strain background.

Alternatively, a mutant strain can be derived from *A. niger* GBA 306 by classical strain improvement as described in WO04/070022 and EP1590444. In these documents, it is extensively described how to screen for an oxalate deficient *A. niger* strain and were isolated according to the methods of Examples 1 and 2 of EP1590444.

Example 8

Construction of *Aspergillus niger* GBA 308 (ΔglaA, ΔpepA, ΔhdfA, Adapted BamHI Amplicon, ΔamyBII, ΔamyBI, ΔamyA, ΔoahA, ΔfumB)

In the genome sequence of CBS 513.88, a putative fumonisin gene cluster was identified on the basis of homology to a gene cluster in *Gibberella moniliformis*, encoding the mycotoxin fumonisin (Pel et al., "Genome sequencing and analysis of the versatile cell factory *Aspergillus niger* CBS 513.88". Nat Biotechnol. 2007 February; 25 (2):221-231).

| Gene ID | Description |
| --- | --- |
| An01g08620 | Strong similarity to fatty acid omega-hydrolase (P450foxy) CYP505 - *Fusarium oxysporum* |
| An01g06830 | Similarity to 3-ketosphinganine reductase Tsc10 - *Saccharomyces cerevisiae* |
| An01g06840 | Strong similarity to acid-CoA ligase Fat2 - *Saccharomyces cerevisiae* |
| An01g06850 | Strong similarity to 4-hydroxybutyrate dehydrogenase - *Alcaligenes eutropus* |
| An01g06860 | Strong similarity to hypothetical protein Fum9p - *Gibberella moniliformis* |
| An01g06870 | Strong similarity to hypothetical protein Fum8p - *Gibberella moniliformis* |
| An01g06880 | Similarity to dihydroflavonol 4-reductase BAA12723.1 - *Rosa* hybrid cultivar |
| An01g06890 | Similarity to peptide synthase pesA - *Metarhizium anisopliae* |
| An01g06900 | Weak similarity to transcription regulator of maltose utilization amyR - *Aspergillus oryzae* |
| An01g06910 | Strong similarity to cytochrome P450 CYP94A5 - *Nicotiane tabacum* |
| An01g06920 | Strong similarity to multidrug resistance protein ABCC2 - *Homo sapiens* |
| An01g06930 - fumB | Strong similarity to polyketide synthase FUM5 - *Gibberella moniliformis* |
| An01g06940 | Strong similarity to hypothetical transmembrane transport protein SCC30.17c - *Streptomyces coelicolor* |
| An01g06950 | Strong similarity to polyketide synthase FUM5 - *Gibberella moniliformis* |

Figure 13:
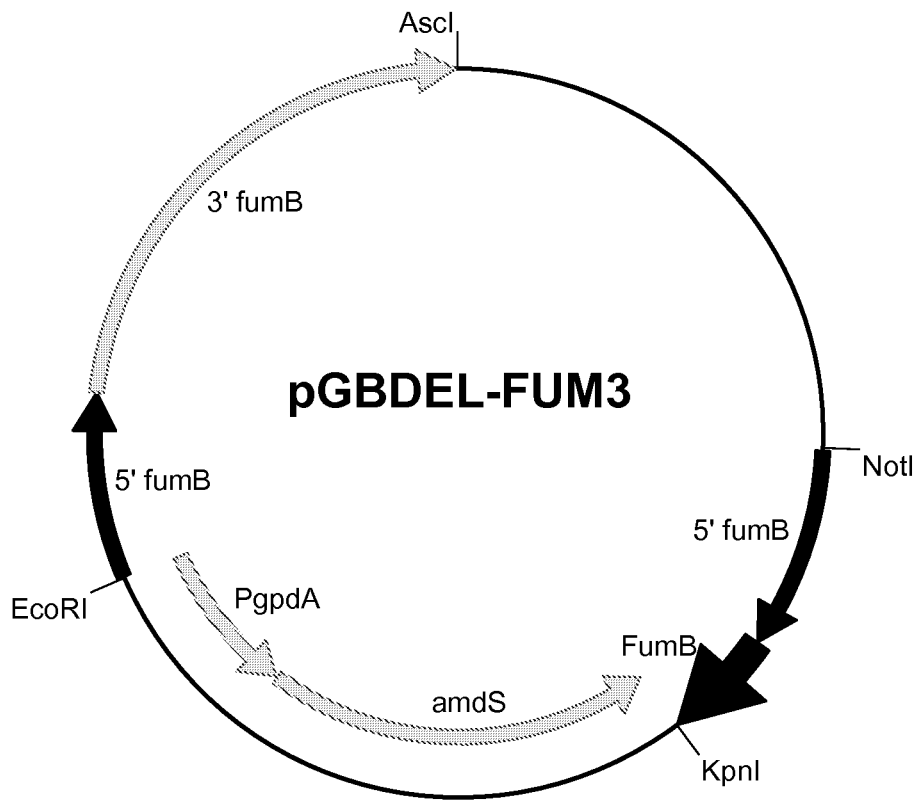
FIG. 13 depicts a physical map of replacement vector pGB-DEL-FUM3. Indicated are the 5' fumB region with part of the fumB coding sequence and the 3' fumB flanking regions relative to the amdS marker. The sequence of the 5'-sequences of fumB overlap at least a few hundred bp. The *E. coli* DNA can be removed by digestion with restriction enzyme AscI and NotI, prior to transformation of the host strain.

The gene An01g06930 encodes a polyketide synthase (PKS) possibly involved in fumonisin production. Gene-flanking regions, with on the promoter side also a small part of the coding sequence of the putative fumB gene (An01g06930), were cloned as essentially described in Example 2 and more detailed in WO06/040312, in vector pGBDEL (FIG. 1), resulting in vector pGBDEL-FUM3 (FIG. 13). Linear DNA of deletion vector pGBDEL-FUM3 was isolated and used to transform *Aspergillus niger* GBA 307 as earlier described in WO06/040312 to delete the fumB gene. A transformant was selected with the fumB ORF removed upon integration of pGBDEL-FUM3 in the genome at the homologous An01g06930 locus by a double cross-over event, resulting in the removal of approximately 8 kb of genome sequence. Subsequently, the amdS marker was removed by plating on fluoro-acetamide media, to select marker-gene-free strains. Strain GBA 308 was selected as a representative strain with the fumB gene inactivated in the GBA 307 strain background.

Strain WT1 and GBA 308 were grown on CYA and YES agar media and fumonisin production was measured. The results of the FB2 measurements are indicated in the Table below.

| Strain | FB2 on CYA (ng/cm2) | FB2 on YES (ng/cm2) |
|---|---|---|
| WT 1 | 772 | 218 |
| GBA 308 | 0 | 0 |

From these results, it is clear that disruption of the PKS-encoding fumB gene results in strains with impaired fumonisin production. A fumonisin-negative strain background has a clear benefit for commercial protein production.

In addition it was shown that strains with disruption of a large gene cluster comprising genes An01g06820 until An01g06930 (having approximately 38 kb of genome sequence removed) shows an identical phenotype, i.e. being negative in fumonisin production in the test as detailed above (data not shown).

Example 9

Construction of *Aspergillus niger* GBA 309 (ΔglaA, ΔpepA, ΔhdfA, Adapted BamHI Amplicon, ΔamyBII, ΔamyBI, ΔamyA, ΔoahA, ΔfumB, Δoch)

In the genome sequence of CBS 513.88, a putative ochratoxin gene cluster was identified on the basis of a PKS fragment of *A. ochraceus* involved in ochratoxin production (Pel et al., "Genome sequencing and analysis of the versatile cell factory *Aspergillus niger* CBS 513.88". Nat Biotechnol. 2007 February; 25 (2):221-231).

| Gene ID | Description |
|---|---|
| An15g07860 | Strong similarity to hypothetical short chain dehydrogenase SPCC736.13 - *Schizosaccharomyces pombe* |
| An15g07870 | Strong similarity to alcohol dehydrogenase adhT - *Bacillus stereothermophilus* |
| An15g07880 | Strong similarity to hypothetical hydrolase A - *Amycolatopsis orientalis* |
| An15g07890 | Similarity to protein c-fos - *Xenopus laevis* |
| An15g07900 | Strong similarity to cytochrome P450 - *Myrothecium roridum* |
| An15g07910 - ochB | Strong similarity to cyclic peptide AM-toxin synthase AMT - *Alternaria alternaria* |
| An15g07920 - ochA; | Strong similarity to PKS of *A. ochraceus* fragment involved in ochratoxin biosynthesis |
| An15g07930 | Strong similarity to nitric oxide synthase - *Manduca sexta* [truncated ORF] |

This PKS-like gene is annotated as An15g07920 (called ochA). Additionally, the gene An15g07910 (called ochB) could represent a potential peptide synthase involved in ochratoxin production. Disruption of the peptide synthase and/or PKS-encoding genes could lead to strains impaired in ochratoxin production.

Figure 14:
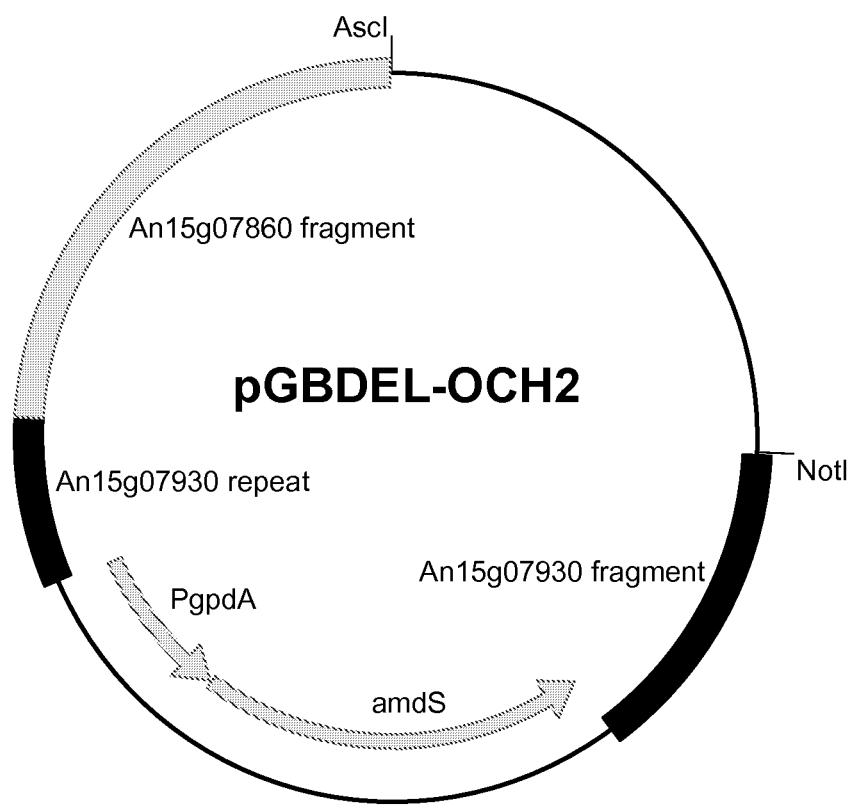
FIG. 14 depicts a physical map of replacement vector pGB-DEL-OCH2. Indicated are part of the An15g07860 gene sequence and part of the An15g07930 gene sequence as flanking regions relative to the amdS marker. The sequence of the An15g07930 gene overlap at least a few hundred by to allow counter selection by homologous recombination. The *E. coli* DNA can be removed by digestion with restriction enzyme AscI and NotI, prior to transformation of the host strain.

To be able to disrupt the full ochratoxin gene cluster using targeting sequences for double cross-over, a gene sequence fragment of the An15g07860 ORF on one side and a gene sequence fragment of the An15g07930 ORF on the other side were cloned as essentially described in Example 2 and more detailed in WO06/040312, resulting in vector pGBDEL-OCH2 (FIG. 14). Linear DNA of deletion vector pGBDEL-OCH2 was isolated and used to transform *Aspergillus niger* GBA 308 as earlier described in WO06/040312 to delete the putative ochratoxin gene cluster. A transformant was selected with the och ORF's removed upon integration of pGBDEL-OCH2 in the genome at the homologous loci by a double cross-over event. Subsequently, the amdS marker was removed by plating on fluoro-acetamide media, to select marker-gene-free strains. Strain GBA 309 was selected as a representative strain with the ochratoxin genomic gene cluster (between gene An15g07860 and An15g07930; genotypically indicated as Δoch) removed in the GBA 308 strain background.

Strain WT1 and GBA 309 were grown on CYA and YES agar media and ochrotoxin A production was measured. The results of the OTA measurements are indicated in the Table below.

| Strain | OTA on CYA (ng/cm2) | OTA on YES (ng/cm2) |
|---|---|---|
| WT 1 | 0 | 178 |
| GBA 309 | 0 | 0 |

From these results, it is clear that disruption of the ochratoxin gene cluster comprising a putative peptide synthase and PKS involved in OTA biosynthesis results in strains with impaired ochratoxin A production. A ochratoxin A-negative and a possible combination with a fumonisin-negative strain background has a clear benefit for commercial protein production.

Example 10

Construction of *Aspergillus niger* GBA 310 (ΔglaA, ΔpepA, ΔhdfA, Adapted BamHI Amplicon, ΔamyBII, ΔamyBI, ΔamyA, ΔoahA, ΔfumB, Δoch, ΔprtT)

Figure 15:
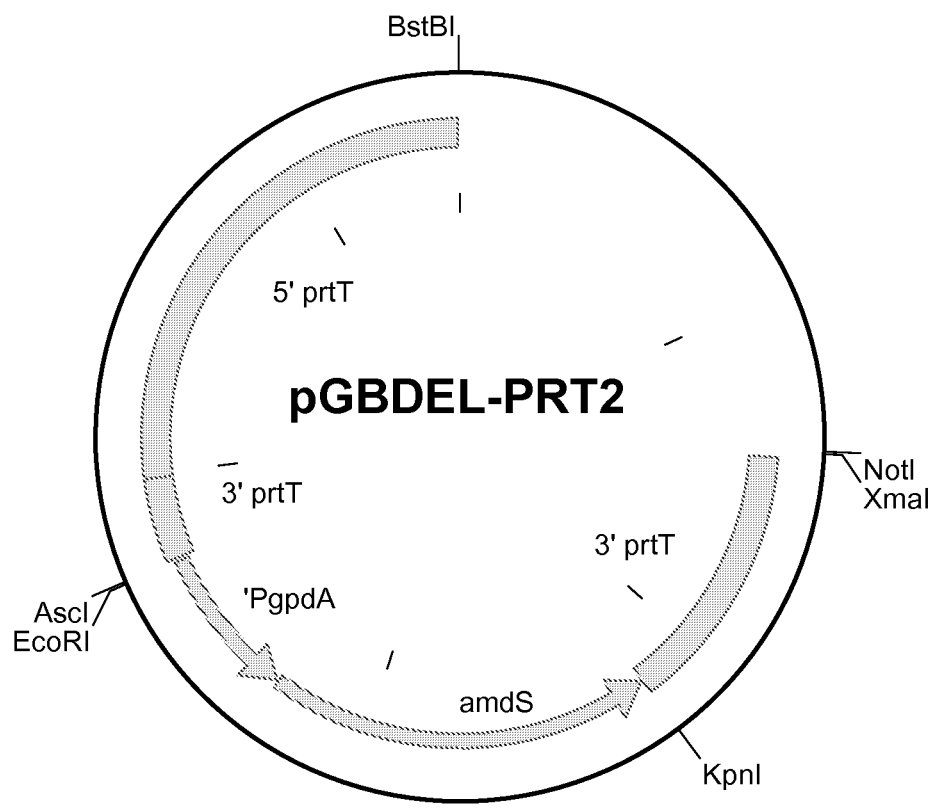
FIG. 15 depicts a physical map of replacement vector pGB-DEL-PRT2. Indicated are the 5' prtT flanking region, the 3' prtT flanking regions relative to the amdS marker. The sequence of the prtT 3' sequences overlap at least a few hundred bp. The *E. coli* DNA can removed by digestion with restriction enzyme BstBI and XmaI, prior to transformation of the host strain.

Gene-flanking regions of the prtT ORF, encoding a protease regulator, were cloned as essentially described in Example 2 and more detailed in WO06/040312, resulting in vector pGBDEL-PRT2 (FIG. 15). Linear DNA of deletion vector pGBDEL-PRT2 was isolated and used to transform *Aspergillus niger* GBA 309 as earlier described in WO06/040312 to delete the prtT gene. A transformant was selected with the prtT ORF removed upon integration of pGBDEL-PRT2 in the genome at the homologous prtT locus by a double cross-over event. Subsequently, the amdS marker was removed by plating on fluoro-acetamide media, to select marker-gene-free strains. Strain GBA 310 was selected as a representative strain with the prtT gene inactivated in the GBA 309 strain background.

Example 11

Construction of *Aspergillus niger* GBA 311 (ΔglaA, ΔpepA, ΔhdfA, Adapted BamHI Amplicon, ΔamyBII, ΔamyBI, ΔamyA, ΔoahA, ΔfumB, Δoch, ΔprtT, Sec61 S376W Mutation)

In this example, the introduction of a modified sec61 gene, called sec61* encoding a Sec61* protein in which Serine 376 is replaced by tryptophan, is described. To do so, gene-flankings and sec61* coding sequence, encoding a modified Sec61 translocation channel, were cloned as essentially described in detail in WO2005123763, resulting in vector pGBDEL-SEC61* (FIG. 16). Linear DNA of deletion vector pGBDEL-SEC61* was isolated and used to transform *Aspergillus niger* GBA 310 as earlier described in WO2005123763 to modify the Sec61 gene. A transformant was selected with a modified Sec61* ORF upon integration of pGBDEL-SEC61* in the genome at the homologous Sec61 locus by a double cross-over event. Subsequently, the amdS marker was removed by plating on fluoro-acetamide media, to select marker-genefree strains. Strain GBA 311 was selected as a representative strain with the Sec61 gene modified in the GBA 310 strain background.

Example 12

Improved Enzyme Production and Production Strain Building Using Adapted *Aspergillus niger* Strains and Plasmids Porcine phospholipase A2 (PLA2) protein (Roberts I. N., Jeenes D. J., MacKenzie D. A., Wilkinson A. P., Sumner I. G. and Archer D. B. (1992) "Heterologous gene expression in *Aspergillus niger*: a glucoamylase-porcine pancreatic phospholipase $A_2$ fusion protein is secreted and processed to yield mature enzyme" Gene 122: 155-161) was selected as a model protein for enzyme expression in the *A. niger* CBS 513.88 & GBA-strain lineage. The fragment for overexpression of PLA2 was made as a fusion of proPLA2 with a native glucoamylase A gene of *A. niger* and was prepared in principle as described by Roberts et al. (1992). This glaA-pla2 fusion gene was cloned into pGBTOP-8 and pGBTOP-12, resulting in pGBTOPPLA-2a (FIG. 17) and pGBTOPPLA-2b (FIG. 18), respectively.

Additionally, alpha-amylase of *A. niger* was used as a second model protein for enzyme expression in the *A. niger* CBS 513.88 & GBA-strain lineage. The amyB coding sequence used for overexpression comprised a single-codon and codon-pair optimized coding sequence for the alpha-amylase encoding amyB gene (as described in detail in WO2008/000632). The translational initiation sequence of the glucoamylase glaA promoter has been modified into 5'-CACCGTCAAA ATG-3' in the amyB expression constructs generated (as also detailed in WO2006/077258). In addition, an optimal translational termination sequence was used, and therefore the wild-type 5'-TGA-3' translational termination sequence was replaced by 5'-TAAA-3' (as detailed in WO2006/077258) in all expression constructs. An EcoRI-SnaBI fragment, comprising an optimized amyB cDNA sequence was synthesized completely, subcloned, sequence verified by sequence analysis. The amyB fragment was cloned into pGBTOP-8 and pGBTOP-12, resulting in pGBTOPFUA-2 (FIG. 19) and pGBTOPFUA-3 (FIG. 20), respectively.

Example 12.1

Improved Targeting of Adapted Expression Vectors to ΔglaA Loci in *A. niger* Strains The constructed integration vectors (Example 3.3 and 12) can be divided into two types: The integration vectors that can be used to target to the non-adapted ΔglaA loci to the 3' glaA and 3"glaA sequences, and which are vectors pGBTOPPLA-2a, pGBTOPFUA-2 and pGBAAS-1. Additionally, novel integration vectors have been constructed that can be used to target specifically to the adapted BamHI ΔglaA amplicon (an adapted ΔglaA locus) to a truncated $P_{glaA}$ promoter fragment and the 3' glaA fragment. The vectors that can be used to target to the adapted BamHI amplicon are pGBTOPPLA-2b, pGBTOPFUA-3, pGBAAS-3 and pGBAAS-4.

The two PLA2 expression vectors (pGBTOPPLA-2a and pGBTOPPLA-2b) were introduced by co-transformation with pGBBAAS-1 and pGBAAS-4 in *A. niger* GBA 301 (ΔglaA, ΔpepA), GBA 302 (ΔglaA, ΔpepA, ΔhdfA) and GBA 303 (ΔglaA, ΔpepA, ΔhdfA, adapted BamHI amplicon) according the scheme below (Table 3). Transformation and subsequent selection of transformants was carried out as described in WO98/46772 and WO99/32617. In principle, linear DNA of all four vectors was isolated and used to co-transform the three *A. niger* strains. Integration of both linearized plasmids occurs via a single cross-over event at one of the ΔglaA loci. Transformants were selected on acetamide media and colony purified according standard procedures. Hundred transformants possessing both the amdS marker gene and the PLA2 expression cassette were identified by PCR using amdS and PLA2-specific primers for all three strains. On the identified co-transformants, targeting PCR tests were performed (as detailed in Example 1.4 of WO98/46772) to determine the percentage of strains with either the amdS and/or PLA2 cassettes integrated in a ΔglaA locus.

Additionally, amdS marker-gene free strains were selected of identified ΔglaA targeted co-transformants by plating on fluoro-acetamide media. A PCR-based DNA 'flag-test' was performed to detect a potential loss of an amplicon in the amdS-free progeny. As explained in Example 1.4.f of WO98/46772, this is an indication for a simultaneous loss of the amdS marker and the entire glaA amplicon through recombination and as such an indication the location of the original cassette(s). This test was used to determine the targeting frequency to the BamHI amplicon in all three strains. Data are shown in Table 3.

TABLE 3

Targeting frequencies of positive co-transformants, containing a PLA2 expression cassette and an amdS marker-gene.

| Plasmids | Strain | Targeting to ΔglaA loci * (BamHI, SalI, BglII) | Targeting to BamHI ΔglaA locus ** |
|---|---|---|---|
| pGBTOPPLA-2 pGBBAAS-1 | GBA 301 | 15% | 4% |
| pGBTOPPLA-2 pGBBAAS-1 | GBA 302 | 87% | 25% |
| pGBTOPPLA-3 pGBBAAS-4 | GBA 303 | 91% | 88% |

* As identified by targeting PCR test
** As identified by DNA flag-PCR test of marker-gene free progenies As can be concluded from Table 3, the use of adapted expression vectors in combination with a adapted targeting DNA domain (the adapted BamHI amplicon) gives a clear advantage in targeted strain building, resulting in a more focussed and efficient strain construction.

Example 12.2

Improved Co-Transformation Using Adapted Constructs and *A. niger* Strains

The FUA expression vector pGBTOPFUA-3 was introduced by co-transformation with pGBAAS-3 and pGBAAS-4 in *A. niger* GBA 307 (ΔglaA, ΔpepA, ΔhdfA, adapted BamHI amplicon, ΔamyBII, ΔamyBI, ΔamyA, ΔoahA), with pGBTOPFUA-2 and pGBAAS as reference set, according the scheme below (Table 4). Transformation and subsequent selection of transformants was carried out as described in WO98/46772 and WO99/32617. In principle, linear DNA of the five vectors was isolated and used to co-transform the *A. niger* GBA 307 strain. Integration of both linearized plasmids occurs via a single cross-over event at the adapted BamHI ΔglaA amplicon or ΔglaA amplicons, respectively. Transformants were selected on acetamide media and colony purified according standard procedures.

The co-transformation percentages (principally as detailed in Example 1.4 of WO98/46772) were determined for 50 transformants of each of the plasmid combinations by PCR using amdS and amyB-specific (codon-pair optimized amyB coding sequence) primers. Data are shown in Table 4.

TABLE 4

Co-transformation frequencies of a FUA expression cassette and an amdS marker-gene cassette.

| Co-transforming plasmids | Strain | Co-transformation % * |
| --- | --- | --- |
| pGBTOPFUA-2 & pGBAAS-1 | GBA 307 | 42% |
| pGBTOPFUA-3 & pGBAAS-4 | GBA 307 | 48% |
| pGBTOPFUA-3 & pGBAAS-3 | GBA 307 | 94% |

* As identified by PCR test

With the previously known pGBAAS-1 and its variant for improved targeting pGBAAS-4, typical co-transformation frequencies are obtained (normally between 25-75%). Surprisingly, as can be concluded from Table 4, the use of the pGBBAAS-3 variant (amdS gene under control of glaA promoter) in combination with an adapted targeting construct (such as pGBTOPFUA-3) gives a very high co-transformation frequency. The use of pGBAAS-3, increases co-transformation frequencies dramatically, avoiding the need for selection of co-transformants before further strain manipulations in targeted strain building, and thus resulting in a more efficient strain construction.

Shake-flask analysis in FM1 of these transformants indicated a similar FUA expression level per gene copy for the different constructs expressed in GBA 307.

Example 12.3

Improved Strain Building in Adapted *A. niger* Strains

One way of constructing recombinant industrial *A. niger* production strains is to integrate expression cassettes in one of the ΔglaA loci and subsequently multiplying the ΔglaA locus with integrated expression cassettes through gene conversion or amplification.

Expression cassettes can be improved through several methods as detailed for example in WO 2005/100573, WO2006/077258, WO 2006/092396 or WO2008/000632. The use of gene conversion or amplification in strain building has been described in more detail in for example WO1998/46772. In the previous examples it has been shown how co-transformation and/or targeting to a specific locus can be improved by strain and plasmid adaptation. In this example, the use of gene conversion or amplification in strain construction using novel GBA types of strains will be demonstrated.

The *A. niger* GBA 311 (Example 11) strain was co-transformed with 2 combinations of expression vectors (i.e. pGB-TOPPLA-2a & pGBBAAS-1 mix; pGBTOPPLA-2b & pGB-BAAS-3 mix). Transformation and subsequent selection of transformants was carried out as described in WO98/46772 and WO99/32617. In principle, linear DNA of all vectors used was isolated and used to co-transform the GBA 311 *A. niger* strain. Integration of both linearized plasmids occurs via a single cross-over event at a ΔglaA locus (See example 12.1 for details in targeting sequences). Transformants were selected on acetamide media and colony purified according standard procedures. Hundred transformants possessing both the amdS marker gene and the PLA2 expression cassette were identified by PCR using amdS and PLA2-specific primers. On the identified co-transformants, targeting PCR tests were performed (as detailed in Example 1.4 of WO98/46772) to determine the percentage of strains with either the amdS and/or PLA2 cassettes integrated in a ΔglaA locus. In addition, colonies were diagnosed for PLA2-copy number using PCR. Copy numbers for suspected high-copy strains were determined more accurately using Southern analysis (WO98/46772). For the mix of pGBTOPPLA-2 & pGBBAAS-1, additional transformants were screened and purified to isolate a transformant with a higher copy number of PLA2 expression cassettes. After screening 600 individual transformants, a 6-copy BglII-targeted transformant was isolated. Resulting data are shown in Table 5.

TABLE 5

Co-transformation frequencies and copy number determination of PLA-2 transformants in the GBA 311 strain background.

| Plasmids | Strain | # of strains tested | Targeting to ΔglaA locus * | Highest copy number of pla expression cassettes |
| --- | --- | --- | --- | --- |
| pGBTOPPLA-2 pGBBAAS-1 | GBA 311 | 100 | 11% (SalI, BglII) | 3 copies (6 copies after screening 600 colonies) |
| pGBTOPPLA-3 pGBBAAS-3 | GBA 311 | 100 | 93% (BamHI) | 7 copies |

* As identified by targeting PCR test
** As identified by Southern analysis (WO98/46772)

For the two high-copy strains, i.e. the 6-copy BglII-targeted strain and the 7-copy BamHI-targeted strain in the GBA300 background, convertants with an increased PLA2-copy number were isolated (for experimental details see Example 3.1 herein and WO98/46772). Upon screening of 500 individual progenies of both strains, 2 strains with multiplied PLA-2 copy numbers as a result of gene conversion were identified for the BamHI-targeted strain and none for the BglII-targeted strain. The two convertants contained 13 and 14 PLA-2 copies, respectively. This example and data clearly indicate that adaptation of a genomic targeting DNA domain (that for example has enhanced gene conversion or amplification frequencies) has great impact on strain construction by facilitating and speeding up the process of defined and controlled construction of a multi copy (production) strain. Shake-flask analysis in FM2 of these transformants indicated a similar PLA2 expression level per gene copy for the different constructs expressed in GBA 311.

The invention claimed is:

1. A recombinant host cell for the production of a compound of interest, said recombinant host cell comprising at least two substantially homologous DNA domains comprising flanking regions of at least 100 base pairs and overall homology of the flanking regions of at least 60%, wherein said at least two substantially homologous DNA domains are suitable for integration of one or more copies of a polynucleotide of interest wherein at least one of the at least two substantially homologous DNA domains is adapted to have enhanced integration preference for the polynucleotide of interest compared to the substantially homologous DNA domain it originates from, and wherein the substantially homologous DNA domain where the adapted substantially homologous DNA domain originates from has a gene conversion frequency that is at least 10% higher than one of the other of the at least two substantially homologous DNA domains, and wherein the recombinant host cell is deficient in glaA and at least one component selected from the group consisting of amyA, amyBI, amyBII, oahA, a toxin associated polynucleotide, and a fungal transcriptional activator of protease (prtT) as compared to a parent cell that the recombinant host cell originates from when cultivated under comparable conditions.

2. The recombinant host cell of claim 1, wherein the recombinant host cell is deficient in amyA.

3. The recombinant host cell of claim 1, wherein the recombinant host cell is deficient in amyBI.

4. The recombinant host cell of claim 1, wherein the recombinant host cell is deficient in amyBII.

5. The recombinant host cell of claim 1, wherein the recombinant host cell is deficient in oahA.

6. The recombinant host cell of claim 5, wherein the recombinant host cell is further deficient in at least one of the components selected from the group consisting of amyA, amyBI, amyBII, a toxin associated polynucleotide, and prtT.

7. The recombinant host cell of claim 5, wherein the recombinant host cell is further deficient in a toxin associated polynucleotide and at least one of the components selected from the group consisting of amyA, amyBI, amyBII, and prtT.

8. The recombinant host cell of claim 5, wherein the recombinant host cell is further deficient in amyA, amyBI, amyBII, and at least one component selected from the group consisting of a toxin associated polynucleotide and prtT.

9. The recombinant host cell of claim 1, wherein the recombinant host cell is deficient in a toxin associated polynucleotide.

10. The recombinant host cell of claim 9, wherein said toxin associated polynucleotide encodes a fungal toxin.

11. The recombinant host cell of claim 10, wherein said fungal toxin is selected from the group consisting of fumonisin and ochratoxin.

12. The recombinant host cell according to claim 9, wherein the recombinant host cell has a deficiency of fumonisin, ochratoxin, and at least one additional toxin or toxin intermediate compound compared to the parent cell from which the recombinant host cell originates when cultivated under comparable conditions.

13. The recombinant host cell of claim 1, wherein the recombinant host cell is deficient in prtT.

14. The recombinant host cell of claim 1, wherein the recombinant host cell has at least 5% deficiency of glaA, amyA, amyBI, amyBII, oahA, a toxin associated polynucleotide, or prtT as compared to the parent cell that the recombinant host cell originates from when cultivated under comparable conditions.

15. The recombinant host cell of claim 1, wherein the recombinant host cell has 100% deficiency of glaA, amyA, amyBI, amyBII, oahA, a toxin associated polynucleotide or prtT as compared to the parent cell that the recombinant host cell originates from when cultivated under comparable conditions.

16. The recombinant host cell of claim 1, wherein the recombinant host cell:
   a) comprises a modification of Sec61; and/or
   b) is deficient in a non-homologous recombination component; and/or
   c) is deficient in pepA; and/or
   d) is selection marker free; and/or
   e) is a recombinant filamentous fungal cell.

17. The recombinant host cell according to claim 16, wherein said non-homologous recombination component is ku70, hdfA or a homologue thereof or ku80, hdfB or homologue thereof.

18. The recombinant host cell of claim 16, wherein said filamentous fungus is *Aspergillus, Chrysosporium, Penicillium, Talaromyces, Fusarium or Trichoderma*.

19. The recombinant host cell of claim 18, wherein said filamentous fungus is *Aspergillus niger, Aspergillus awamori, Aspergillus foetidus, Aspergillus sojae, Aspergillus fumigatus, Talaromyces emersonii, Aspergillus oryzae, Chrysosporium lucknowense, Fusarium oxysporum, Trichoderma reesei or Penicillium chrysogenum*.

20. Method for the production of a compound of interest, comprising:
   (a) cultivating a host cell according to claim 1 under conditions conducive to the production of said compound; and
   (b) recovering the compound of interest from the cultivation medium.

21. The method according to claim 20, wherein the compound of interest is a polypeptide.

22. The method according to claim 21, wherein the polypeptide is an enzyme.

23. The method according to claim 20, wherein the compound of interest is a metabolite.

* * * * *

SEQUENCE LISTING

<160> NUMBER OF SEQ ID NOS: 3

<210> SEQ ID NO 1
<211> LENGTH: 4500
<212> TYPE: DNA
<213> ORGANISM: Artificial Sequence
<220> FEATURE:

```
<223> OTHER INFORMATION: Truncated glaA amplicon
<220> FEATURE:
<221> NAME/KEY: misc_feature
<222> LOCATION: (1)..(2349)
<223> OTHER INFORMATION: 3'-glaA fragment
<220> FEATURE:
<221> NAME/KEY: misc_feature
<222> LOCATION: (2350)..(4500)
<223> OTHER INFORMATION: 3"-glaA fragment

<400> SEQUENCE: 1
tagacaatca atccatttcg ctatagttaa aggatgggga tgagggcaat tggttatatg      60
atcatgtatg tagtgggtgt gcataatagt agtgaaatgg aagccaagtc atgtgattgt     120
aatcgaccga cggaattgag gatatccgga aatacagaca ccgtgaaagc catggtcttt     180
ccttcgtgta aagaccaga cagacagtcc ctgatttacc cttgcacaaa gcactagaaa      240
attagcattc catccttctc tgcttgctct gctgatatca ctgtcattca atgcatagcc     300
atgagctcat cttagatcca agcacgtaat tccatagccg aggtccacag tggagcagca     360
acattcccca tcattgcttt ccccaggggc ctcccaacga ctaaatcaag agtatatctc     420
taccgtccaa tagatcgtct tcgcttcaaa atctttgaca attccaagag ggtccccatc     480
catcaaaccc agttcaataa tagccgagat gcatggtgga gtcaattagg cagtattgct     540
ggaatgtcgg ggccagttgg cccggtggtc attggccgcc tgtgatgcca tctgccacta     600
aatccgatca ttgatccacc gcccacgagg cgcgtctttg cttttttgcgc ggcgtccagg    660 ttcaactctc tctgcagctc cagtccaacg ctgactgact agtttaccta ctggtctgat     720
cggctccatc agagctatgg cgttatcccg tgccgttgct gcgcaatcgc tatcttgatc     780
gcaaccttga actcactctt gttttaatag tgatcttggt gacggagtgt cggtgagtga     840
caaccaacat cgtgcaaggg agattgatac ggaattgtcg ctcccatcat gatgttcttg     900
ccggctttgt tggccctatt cgtgggatgc gatgccctcg ctgtgcagca gcaggtactg     960
ctggatgagg agccatcggt ctctgcacgc aaacccaact tcctcttcat tctcacggat    1020
gatcaggatc tccggatgaa ttctccggcg tatatgccgt atacgcaggc gagaatcaag    1080
gaaaagggta ccgagttctt gaaccatttc gtcactaccg cgctttgctg tccgtcgcgc    1140
gtgagtcttt ggacgggaag acaggctcat aatactaatg tgacggatgt gaacccgcct    1200
tatggtatgg acactgcttc gatcggtctt gattcttcag cgtggttaca attgctaatg    1260
cggcataggc ggatacccca aattcgtcgc tcaaggcttc aacgaaaact tcctccccgt    1320
ttggctgcag tccgccggtt acaataccta ctacacgggg aagctgttca actcgcacag    1380
tgtcgctacc tataacgcgc cctttgtgaa cggtttcaat ggctccgact tcctcctcga    1440
cccccacaca tattcctact ggaatgcgac ataccagcga aaccatgagc tccgcggag     1500 ttacgaggga caatatacta cggatgtgat gaaggagaag gcatcgggat tgttggcaga    1560
tgcgctggac agtgacgcgc cattcttcct gacggtcgcg ccgatcgcac cgcacacgaa    1620
catcgatgtg gagggctga gcggtgcggg tggaccgaag atgacagagc cgctgcctgc     1680
accgagacat gcgcatttgt ttgctgatgc aaaggtgccg cggacgccta atttcaatcc    1740
ggacaaggtg tgtgatatcc tgacacagtg gtgggacgg gcactgacaa gagtaggatt     1800
ctggtgcggg gtggatccaa accatggaac tacagaacca gaccgtcatc gactacgaag    1860
accatcttta tcgccagcgt ctgcgcactt tgcaagccgt cgatgagatg gtggatgcgc    1920
tgatcacgca gctggaagaa agtgggcaga tcgacaatac ctacatcatt tacagtgctg    1980
ataacggcta ccacattggc catcaccgtc taccccccgg caagacaact ggctatgaag    2040
```

```
aggacattcg cgtaccattc tacattcgcg gacctggcat tcctgaggga aagagcgttg    2100
accgtgtaac cacgcacatt gacattgcac ctacactgtt cgagttggct ggggttccct    2160
tgcgagagga ctttgacggg actccgatgc ccgtgtcgac tagcaagaag acccagtcaa    2220
tcttgcatga gcatgtcaca gtcgaattct ggggtcacgc ggtgcttgag ggcgaatacg    2280
gctccatcgg tgagtaacct ctctcttact accacggaaa catcactgac gtaaccagga    2340
cccggcggct tatccatcat gggaaacaac acctacaaat ccgccagaat tctctcggaa    2400
gaatataacc tctactactc cgtctggtgc gacggtgacc acgagctgta cgatctctca    2460
gtaagtgcca accggttccc gccactatcg taaaaacaaa aaatctaaca acaccagacg    2520
gaccCctacc aaatgaacaa catctacacc caacaagaca acatccacct cctaagcaga    2580
cctctatcca gcgtgattga tcgtatcgac gctctccttc tggttctgaa atcctgcaag    2640
ggtaacacat gcatccagcc gtggcgggtc ctccaccccg acgggtccgt agagagcctc    2700
aaagatgcac tgcaggtgaa atacgattcc ttttacacca accagcccaa ggtgtcgtat    2760
tcagtatgtg aacccgggta catcattgag gctgaggggc ccaggtcgg attgcagtat     2820 agagatgggc tgagttggga ggcgtggact tgacgattcc gtcaagtatg agtatgggta    2880
cgaataatga gcgttattgc tatgtatttt tatagatagt ttatttatat atcatgacta    2940
aacttgagag ccatggaatc aatgaaatga catggcgagt gtagatcacg atagtcatag    3000
tagccgaagt gggcggatag ccaagaataa caccagaatc agataacagg aacatcacaa    3060
ccgatcacac catagataat atccaaagaa gtttaaatag ccgagacaaa gagaatagag    3120
acaagataca tggaacaaga aaggtacacc cggtagataa accctgggac gggcccgagt    3180
ccttacccat agatcaatcc cacgggaaca aaaccaaagt caacaaccac caccaccatt    3240
accacaaccg catcaataga accggtgaaa aatgacacca tcgaatcctt caccctaagt    3300
aaagccctgt acgttgcata tcgcttaagc acaaaagtag tagaatagat atgagcccgc    3360
acgcgcggcc aacgatccaa actagccctg acatcaaagc cagcggcgat tgcgccatca    3420
agcccccgtc tcacttcata gtggaattgc gggtcacctc actgattgac tgtctgtcta    3480
gacacactca cccacgcatg ctgtctgtgc ccagaacgtg gactttggct ctgccgagct    3540
agaggatcaa atataagtag attggatgta ggcccgtatt ttttttattt cgtgtgactc    3600
ggagatttta tgcgttgtgt tgttgggcgg aaaaagaaat atactttctt tttgttcttt    3660 tcttttttctc tctattgctt gccttggata tcccttgcat acggtcggtt gctgattgac    3720
taagggtgct gtcttgtgtc actgaactgc tgctcaacct ctgtctggta ttcctgttgt    3780
cgtgatggtg gggaaacagt tcgagttcga ggaccagagg gatggcatcg tgcctccctt    3840
ggaggaaaag aaggtcgtcg atgaggtcta taccgataat gatgttgcgt cggaggagat    3900
tgtcaaggac tgggatgata aggaggaggg caagctgcgg aggaagtgag tcgtcactgt    3960
tttcattcac tgccatatag gttcaagcat atactgactg gtatataggag tcgatatcat    4020 cctcatcccc attctcgctc tcgctttctt cggcctccag attgatcgcg gcaatatcag    4080
cgcagctctt acctccacta tcaccgaaga cctaggtgtc accacgaacc aaatcaatat    4140
tggaacccag ttgctttcgg ctggtattgt catcaccgag atcccgtcaa atattatact    4200
tcagcgcatc ggtccccagg tctggttgtc ggcacagctg atcgcttggg gtctggttgg    4260
cacattccag gcttttgtac agtcgtaccc ggcgtatctg gccacgaggt tgttgctggg    4320
gctgttggag ggagggttta ttcctggttt gtctggtcgt gcgccttggt ctatggtggt    4380
```

| | | |
|---|---|---|
| agcgctaaca atgggtttgg tacaggtgcc ctgtactatc tctcgacatg gtataaacgt | 4440 | |
| cctgagacga gtttccggac cactctgttc ttctatgggc agatgtttgc cggtgcgacc | 4500 | |

```
<210> SEQ ID NO 2
<211> LENGTH: 5973
<212> TYPE: DNA
<213> ORGANISM: Artificial Sequence
<220> FEATURE:
<223> OTHER INFORMATION: Adapted BamHI amplicon
<220> FEATURE:
<221> NAME/KEY: misc_feature
<222> LOCATION: (1)..(2353)
<223> OTHER INFORMATION: 3'-glaA fragment
<220> FEATURE:
<221> NAME/KEY: misc_feature
<222> LOCATION: (2354)..(3822)
<223> OTHER INFORMATION: Adapted PglaA fragment
<220> FEATURE:
<221> NAME/KEY: misc_feature
<222> LOCATION: (3823)..(5973)
<223> OTHER INFORMATION: 3"-glaA fragment
```

<400> SEQUENCE: 2

| | |
|---|---|
| tagacaatca atccatttcg ctatagttaa aggatgggga tgagggcaat tggttatatg | 60 |
| atcatgtatg tagtgggtgt gcataatagt agtgaaatgg aagccaagtc atgtgattgt | 120 |
| aatcgaccga cggaattgag gatatccgga aatacagaca ccgtgaaagc catggtcttt | 180 |
| ccttcgtgta aagaccaga cagacagtcc ctgatttacc cttgcacaaa gcactagaaa | 240 |
| attagcattc catccttctc tgcttgctct gctgatatca ctgtcattca atgcatagcc | 300 |
| atgagctcat cttagatcca agcacgtact tccatagccg aggtccacag tggagcagca | 360 |
| acattcccca tcattgcttt ccccaggggc ctcccaacga ctaaatcaag agtatatctc | 420 |
| taccgtccaa tagatcgtct tcgcttcaaa atctttgaca actccaagag ggtccccatc | 480 |
| catcaaaccc agttcaataa tagccgagat gcatggtgga gtcaattagg cagtattgct | 540 |
| ggaatgtcgg ggccagttgg cccggtggtc attggccgcc tgtgatgcca tctgccacta | 600 |
| aatccgatca ttgatccacc gcccacgagg cgcgtctttg cttttgcgc ggcgtccagg | 660 |
| ttcaactctc tctgcagctc cagtccaacg ctgactgact agtttaccta ctggtctgat | 720 |
| cggctccatc agagctatgg cgttatcccg tgccgttgct gcgcaatcgc tatcttgatc | 780 |
| gcaaccttga actcactctt gttttaatag tgatctggt gacggagtgt cggtgagtga | 840 |
| caaccaacat cgtgcaaggg agattgatac ggaattgtcg ctcccatcat gatgttcttg | 900 |
| ccggcttttgt tggccctatt cgtgggatgc gatgccctcg ctgtgcagca gcaggtactg | 960 |
| ctggatgagg agccatcggt ctctgcacgc aaacccaact tcctcttcat tctcacggat | 1020 |
| gatcaggatc tccggatcaa tactccggcg tatatgccgt atacgcaggc gagaatcaag | 1080 |
| gaaaagggta ccgagttctt gaaccatttc gtcactaccg cgctttgctg tccgtcgcgc | 1140 |
| gtgagtcttt ggacgggaag acaggctcat aatactaatg tgacggatgt gaacccgcct | 1200 |
| tatggtatgg acactgcttc gatcggtctt gattcttcag cgtggttaca attgctaatg | 1260 |
| cggcataggc ggatacccca aattcgtcgc tcaaggcttc aacgaaaact tcctccccgt | 1320 |
| ttggctgcag tccgccggtt acaataccta ctacacgggg aagctgttca actcgcacag | 1380 |
| tgtcgctacc tataacgcgc cctttgtgaa cggtttcaat ggctccgact tcctcctcga | 1440 |
| cccccacaca tattcctact ggaatgcgac ataccagcga aaccatgagc tccgcgggag | 1500 |
| ttacgaggga caatatacta cggatgtgat gaaggagaag gcatcgggat tgttggcaga | 1560 |
| tgcgctggac agtgacgcgc cattcttcct gacggtcgcg ccgatcgcac cgcacacgaa | 1620 |

```
catcgatgtg gaggggctga gcggtgcggg tggaccgaag atgacagagc cgctgcctgc    1680
accgagacat gcgcatttgt ttgctgatgc aaaggtgccg cggacgccta atttcaatcc    1740
ggacaaggtg tgtgatatcc tgacacagtg gtggggacgg gcactgacaa gagtaggatt    1800
ctggtgcggg gtggatccaa accatggaac tacagaacca gaccgtcatc gactacgaag    1860
accatcttta tcgccagcgt ctgcgcactt gcaagccgt cgatgagatg gtggatgcgc     1920
tgatcacgca gctggaagaa agtgggcaga tcgacaatac ctacatcatt tacagtgctg    1980
ataacggcta ccacattggc catcaccgtc taccccccgg caagacaact ggctatgaag    2040
aggacattcg cgtaccattc tacattgcg gacctggcat tcctgaggga aagagcgttg     2100
accgtgtaac cacgcacatt gacattgcac ctacactgtt cgagttggct ggggttccct    2160
tgcgagagga ctttgacggg actccgatgc ccgtgtcgac tagcaagaag acccagtcaa    2220
tcttgcatga gcatgtcaca gtcgaatagt ggggtcacgc ggtgcttgag ggcgaatacg    2280
gctccatcgg tgagtaacct ctctcttact accacggaaa catcactgac gtaaccagga    2340
cgcggccgct cgaggattgc ctgaacattg acattcggcg tccggccggg accaccgcgg    2400
actcgaagct gcctgtgctg gtctggatct ttggcgagg ctttgaactt ggttcaaagg     2460
cgatgtatga tggtacaacg atggtatcat cgtcgataga caagaacatg cctatcgtgt    2520
ttgtagcaat gaattatcgc gtgggaggtt tcggttcttt gcccggaaag gagatcctgg    2580
aggacgggtc cgcgaaccta gggctcctgg accaacgcct tgccctgcag tgggttgccg    2640
acaacatcga ggcctttggt ggagacccgg acaaggtgac gatttgggga gaatcagcag    2700
gagccatttc cgttttttgat cagatgatct tgtacgacgg aaacatcact tacaaggata    2760
agcccttgtt ccgggggggcc atcatggact ccggtagtgt tgttcccgca gaccccgtcg    2820
atgggtgcaa gggacagcaa gtatatgatg cggtagtgga atctgcaggc tgttcctctt    2880
ctaacgacac cctagcttgt ctgcgtgaac tagactacac cgacttcctc aatgcggcaa    2940
actccgtgcc aggcatttta agctaccatt ctgtggcgtt atcatatgtg cctcgaccgg    3000
acgggacggc gttgtcggca tcaccggacg ttttgggcaa agcagggaaa tatgctcggg    3060
tcccgttcat cgtgggcgac caagaggatg aggggaccett attcgccttg tttcagtcca    3120
acattacgac gatcgacgag gtggtcgact acctggcctc atacttcttc tatgacgcta    3180
gccgagagca gcttgaagaa ctagtggccc tgtacccaga caccaccacg tacgggtctc    3240
cgttcaggac aggcgcggcc aacaactggt atccgcaatt taagcgattg gccgccattc    3300
tcggcgactt ggtcttcacc attacccggc gggcattcct ctcgtatgca gaggaaatct    3360
cccctgatct tccgaactgg tcgtacctgg cgacctatga ctatggcacc ccagttctgg    3420
ggaccttcca cggaagtgac ctgctgcagg tgttctatgg gatcaagcca aactatgcag    3480
ctagttctag ccacacgtac tatctgagct ttgtgtatac gctggatccg aactccaacc    3540
ggggggagta cattgagtgg ccgcagtgga aggaatcgcg gcagttgatg aatttcggag    3600
cgaacgacgc cagtctcctt acggatgatt tccgcaacgg gacatatgag ttcatcctgc    3660
agaataccgc ggcgttccac atctgatgcc attggcggag gggtccggac ggtcaggaac    3720
ttagccttat gagatgaatg atggacgtgt ctggcctcga aaaggatat atggggatca     3780 tgatagtact agccatatta atgaagggca tataccacgc gtttatccat catgggaaac    3840
aacacctaca aatccgccac aatactctcg gaagaatata acctctacta ctccgtctgg    3900
tgcgacggtg accacgagct gtacgatctc tcagtaagtg ccaaccggtt cccgccacta    3960
```

```
tcgtaaaaac aaaaaatcta acaacaccag acggacccct accaaatgaa caacatctac    4020
acccaacaag acaacatcca cctcctaagc agacctctat ccagcgtgat tgatcgtatc    4080
gacgctctcc ttctggttct gaaatcctgc aagggtaaca catgcatcca gccgtggcgg    4140
gtcctccacc ccgacgggtc cgtagagagc ctcaaagatg cactgcaggt gaaatacgat    4200
tccttttaca ccaaccagcc caaggtgtcg tattcagtat gtgaacccgg gtacatcatt    4260
gaggctgagg ggccccaggt cggattgcag tatagagatg gctgagttg ggaggcgtgg    4320 acttgacgat tccgtcaagt atgagtatgg gtacgaataa tgagcgttat tgctatgtat    4380
ttttatagat agtttattta tatatcatga ctaaacttga gagccatgga atcaatgaaa    4440
tgacatggcg agtgtagatc acgatagtca tagtagccga agtgggcgga tagccaagaa    4500
taacaccaga atcagataac aggaacatca caaccgatca caccatagat aatatccaaa    4560
gaagtttaaa tagccgagac aaagagaata gagacaagat acatggaaca agaaaggtac    4620
acccggtaga taaaccctgg gacgggcccg agtccttacc catagatcaa tcccacggga    4680
acaaaaccaa agtcaacaac caccaccacc attaccacaa ccgcatcaat agaaccggtg    4740
aaaaatgaca ccatcgaatc cttcacccta agtaaagccc tgtacgttgc atatcgctta    4800
agcacaaaag tagtagaata gatatgagcc cgcacgcgcg gccaacgatc caaactagcc    4860
ctgacatcaa agccagcggc gattgcgcca tcaagccccc gtctcacttc atagtggaat    4920
tgcgggtcac ctcactgatt gactgtctgt ctagacacac tcacccacgc atgctgtctg    4980
tgcccagaac gtggactttg gctctgccga gctagaggat caaatataag tagattggat    5040
gtaggcccgt attttttta tttcgtgtga ctcggagatt ttatgcgttg tgttgttggg    5100
cggaaaaaga aatatacttt cttttttgttc ttttcttttt ctctctattg cttgccttgg    5160
atatcccttg catacggtcg gttgctgatt gactaagggt gctgtcttgt gtcactgaac    5220
tgctgctcaa cctctgtctg gtattcctgt tgtcgtgatg gtggggaaac agttcgagtt    5280
cgaggaccag agggatggca tcgtgcctcc cttggaggaa aagaaggtcg tcgatgaggt    5340
ctataccgat aatgatgttg cgtcggagga gattgtcaag gactgggatg ataaggagga    5400
gggcaagctg cggaggaagt gagtcgtcac tgttttcatt cactgccata taggttcaag    5460
catatactga ctggtatata ggatcgatat catcctcatc cccattctcg ctctcgcttt    5520
cttcggcctc cagattgatc gcggcaatat cagcgcagct cttacctcca ctatcaccga    5580
agacctaggt gtcaccacga accaaatcaa tattggaacc cagttgcttt cggctggtat    5640
tgtcatcacc gagatcccgt caaatattat acttcagcgc atcggtcccc aggtctggtt    5700
gtcggcacag ctgatcgctt ggggtctggt tggcacattc caggcttttg tacagtcgta    5760
cccggcgtat ctggccacga ggttgttgct ggggctgttg gagggagggt ttattcctgg    5820
tttgtctggt cgtgcgcctt ggtctatggt ggtagcgcta acaatgggtt tggtacaggt    5880
gccctgtact atctctcgac atggtataaa cgtcctgaga cgagtttccg gaccactctg    5940
ttcttctatg ggcagatgtt tgccggtgcg acc                                 5973
```

<210> SEQ ID NO 3
<211> LENGTH: 1469
<212> TYPE: DNA
<213> ORGANISM: Artificial Sequence
<220> FEATURE:
<223> OTHER INFORMATION: Adapted PglaA fragment
<220> FEATURE:
<221> NAME/KEY: misc_feature
<222> LOCATION: (1)..(1469)
<223> OTHER INFORMATION: Adapted PglaA fragment

```
<400> SEQUENCE: 3
ggattgcctg aacattgaca ttcggcgtcc ggccgggacc accgcggact cgaagctgcc      60
tgtgctggtc tggatctttg gcggaggctt tgaacttggt tcaaaggcga tgtatgatgg     120
tacaacgatg gtatcatcgt cgatagacaa gaacatgcct atcgtgtttg tagcaatgaa     180
ttatcgcgtg ggaggtttcg ggttcttgcc cggaaaggag atcctggagg acgggtccgc     240
gaacctaggg ctcctggacc aacgccttgc cctgcagtgg gttgccgaca acatcgaggc     300
ctttggtgga gacccggaca aggtgacgat ttggggagaa tcagcaggag ccatttccgt     360
ttttgatcag atgatcttgt acgacggaaa catcacttac aaggataagc ccttgttccg     420
gggggccatc atggactccg gtagtgttgt tcccgcagac cccgtcgatg gggtcaaggg     480
acagcaagta tatgatgcgg tagtggaatc tgcaggctgt tcctcttcta acgacaccct     540
agcttgtctg cgtgaactag actacaccga cttcctcaat gcggcaaact ccgtgccagg     600
cattttaagc taccattctg tggcgttatc atatgtgcct cgaccggacg ggacggcgtt     660
gtcggcatca ccggacgttt tgggcaaagc agggaaatat gctcgggtcc cgttcatcgt     720
gggcgaccaa gaggatgagg ggaccttatt cgccttgttt cagtccaaca ttacgacgat     780
cgacgaggtg gtcgactacc tggcctcata cttcttctat gacgctagcc gagagcagct     840
tgaagaacta gtggccctgt acccagacac caccacgtac gggtctccgt tcaggacagg     900
cgcggccaac aactggtatc cgcaatttaa gcgattggcc gccattctcg gcgacttggt     960
cttcaccatt acccggcggg cattcctctc gtatgcagag gaaatctccc ctgatcttcc    1020
gaactggtcg tacctggcga cctatgacta tggcaccccca gttctgggga ccttccacgg    1080
aagtgacctg ctgcaggtgt tctatgggat caagccaaac tatgcagcta gttctagcca    1140
cacgtactat ctgagctttg tgtatacgct ggatccgaac tccaaccggg gggagtacat    1200
tgagtggccg cagtggaagg aatcgcggca gttgatgaat ttcggagcga acgacgccag    1260
tctccttacg gatgatttcc gcaacgggac atatgagttc atcctgcaga ataccgcggc    1320
gttccacatc tgatgccatt ggcggagggg tccggacggt caggaactta gccttatgag    1380
atgaatgatg gacgtgtctg gcctcggaaa aggatatatg gggatcatga tagtactagc    1440
catattaatg aagggcatat accacgcgt                                      1469
```